United States Patent
Bürli et al.

(10) Patent No.: US 10,307,422 B2
(45) Date of Patent: *Jun. 4, 2019

(54) PYRAZOLOPYRIDAZINES AND METHODS FOR TREATING RETINAL-DEGENERATIVE DISEASES AND HEARING LOSS ASSOCIATED WITH USHER SYNDROME

(71) Applicant: USHER III INITIATIVE, INC., Chicago, IL (US)

(72) Inventors: Roland Werner Bürli, Bishop's Stortford (GB); William Rameshchandra Krishna Esmieu, Cambridge (GB); Christopher James Lock, Burwell (GB); Karine Fabienne Malagu, Saffron Walden (GB); Andrew Pate Owens, Huntingdon (GB); William E. Harte, Moorpark, CA (US)

(73) Assignee: USHER III INITIATIVE, INC., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/924,831

(22) Filed: Mar. 19, 2018

(65) Prior Publication Data

US 2018/0207159 A1    Jul. 26, 2018

Related U.S. Application Data

(60) Continuation of application No. 15/375,959, filed on Dec. 12, 2016, now Pat. No. 9,925,187, which is a continuation of application No. 14/980,347, filed on Dec. 28, 2015, now Pat. No. 9,549,910, which is a continuation of application No. 14/730,994, filed on Jun. 4, 2015, now Pat. No. 9,260,381, which is a division of application No. 13/791,205, filed on Mar. 8, 2013, now Pat. No. 9,079,909, which is a continuation of application No. PCT/US2012/034959, filed on Apr. 25, 2012.

(60) Provisional application No. 61/576,471, filed on Dec. 16, 2011, provisional application No. 61/537,908, filed on Sep. 22, 2011, provisional application No. 61/478,642, filed on Apr. 25, 2011.

(51) Int. Cl.
| | | |
|---|---|---|
| C07D 487/04 | (2006.01) | |
| A61K 31/5025 | (2006.01) | |
| A61K 31/40 | (2006.01) | |
| C07C 251/86 | (2006.01) | |
| C07D 519/00 | (2006.01) | |
| G01N 33/50 | (2006.01) | |
| G01N 33/68 | (2006.01) | |
| A61K 31/165 | (2006.01) | |
| A61K 31/167 | (2006.01) | |

(52) U.S. Cl.
CPC ........ *A61K 31/5025* (2013.01); *A61K 31/165* (2013.01); *A61K 31/167* (2013.01); *A61K 31/40* (2013.01); *C07C 251/86* (2013.01); *C07D 487/04* (2013.01); *C07D 519/00* (2013.01); *G01N 33/502* (2013.01); *G01N 33/6848* (2013.01); *G01N 33/6893* (2013.01); *C07C 2602/08* (2017.05); *G01N 2333/4703* (2013.01); *G01N 2400/40* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 7,390,808 B2 | 6/2008 | Green et al. | |
| 7,666,647 B2 | 2/2010 | ter Haar et al. | |
| 7,812,166 B2 | 10/2010 | Dai et al. | |
| 7,883,881 B2 | 2/2011 | ter Haar et al. | |
| 8,318,467 B2 | 11/2012 | ter Haar et al. | |
| 8,338,439 B2 | 12/2012 | Singh et al. | |
| 8,450,335 B2 | 5/2013 | Singh et al. | |
| 8,609,679 B2 | 12/2013 | Singh et al. | |
| 8,765,762 B2 | 7/2014 | Bürli et al. | |
| 8,785,391 B2 | 7/2014 | Johansson | |
| 9,079,909 B2 * | 7/2015 | Burli | A61K 31/40 |
| 9,212,181 B2 | 12/2015 | Singh et al. | |
| 9,227,976 B2 | 1/2016 | Bürli et al. | |
| 9,260,381 B2 | 2/2016 | Bürli et al. | |
| 9,371,332 B2 | 6/2016 | Bürli et al. | |
| 9,549,910 B2 | 1/2017 | Bürli et al. | |
| 9,783,545 B2 | 10/2017 | Bürli et al. | |
| 2008/0194562 A1 | 8/2008 | Wyatt et al. | |

(Continued)

FOREIGN PATENT DOCUMENTS

| | | |
|---|---|---|
| JP | 2008-527031 | 7/2008 |
| JP | 2011-503103 | 1/2011 |

(Continued)

OTHER PUBLICATIONS

Supplementary European Search Report for European Application No. 12777328.1, dated May 9, 2014, 5 pages.

(Continued)

*Primary Examiner* — Paul V Ward
(74) *Attorney, Agent, or Firm* — Cooley LLP

(57) ABSTRACT

Compounds, compositions and methods for the treatment of retinal degenerative diseases, such as retinitis pigmentosa, Leber's congenital Amaurosis, Syndromic retinal degenerations, age-related macular degeneration and Usher Syndrome, and hearing loss associated with Usher Syndrome are described herein.

2 Claims, 1 Drawing Sheet

(56) References Cited

U.S. PATENT DOCUMENTS

| | | |
|---|---|---|
| 2010/0029610 A1 | 2/2010 | Singh et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0165462 A1 | 6/2013 | Singh et al. |
| 2013/0252936 A1 | 9/2013 | Bürli et al. |
| 2014/0121197 A1 | 5/2014 | Bürli et al. |
| 2014/0121205 A1 | 5/2014 | Bürli et al. |
| 2014/0288005 A1 | 9/2014 | Johansson |
| 2014/0288093 A1 | 9/2014 | Krainc et al. |
| 2015/0265617 A1 | 9/2015 | Bürli et al. |
| 2015/0266812 A1 | 9/2015 | Bürli et al. |
| 2016/0158172 A1 | 6/2016 | Bürli et al. |
| 2016/0272647 A1 | 9/2016 | Bürli et al. |
| 2017/0143718 A1 | 5/2017 | Bürli et al. |

FOREIGN PATENT DOCUMENTS

| | | |
|---|---|---|
| WO | WO 2003/080616 | 10/2003 |
| WO | WO 2006/077401 | 7/2006 |
| WO | WO 2006/091246 | 8/2006 |
| WO | WO 2006/127396 | 11/2006 |
| WO | WO 2007/075911 | 7/2007 |
| WO | WO 2007/120827 | 10/2007 |
| WO | WO 2008/051757 | 5/2008 |
| WO | WO 2009/039420 | 3/2009 |
| WO | WO 2009/062118 | 5/2009 |
| WO | WO 2010/046013 | 4/2010 |
| WO | WO 2012/148994 | 11/2012 |
| WO | WO 2014/066835 | 5/2014 |
| WO | WO 2014/066836 | 5/2014 |
| WO | WO 2016/201266 | 12/2016 |

OTHER PUBLICATIONS

Office Action for U.S. Appl. No. 13/791,205, dated Aug. 6, 2014, 7 pages.
International Search Report and Written Opinion for International Application No. PCT/US2012/034959, dated Sep. 21, 2012, 10 pages.
Supplementary European Search Report for European Application No. 13849803.5, dated Mar. 21, 2016, 7 pages.
International Search Report and Written Opinion for International Application No. PCT/US2013/066938, dated Jan. 30, 2014, 6 pages.
Partial Supplementary European Search Report for European Application No. 13848995.0, dated Apr. 20, 2016, 6 pages.
Supplementary European Search Report for European Application No. 13848995.0, dated Aug. 12, 2016, 11 pages.
International Search Report and Written Opinion for International Application No. PCT/US2013/066939, dated Mar. 5, 2014, 8 pages.
Office Action for U.S. Appl. No. 13/791,744, dated Jun. 27, 2014, 9 pages.
Office Action for U.S. Appl. No. 14/731,535, dated Oct. 5, 2015, 6 pages.
Office Action for U.S. Appl. No. 15/141,949, dated Feb. 3, 2017, 6 pages.
International Search Report and Written Opinion for International Application No. PCT/US2016/036945, dated Sep. 7, 2016, 12 pages.
Alagramam, K. N. et al., "A small molecule mitigates hearing loss in a mouse model of Usher syndrome III," Nature Chemical Biology, Advance Online Publication,www.nature.com/naturechemicalbiology, DOI:10.1038/NCHEMBIO.2069, 13 pages, published online: Apr. 25, 2016.
Brana, M. F. et al., "Pyrazolo[3,4-c]pyridazines as Novel and Selective Inhibitors of Cyclin-Dependent Kinases," J. Med. Chem., 48(22):6843-6854 (2005).
Churcher, I., "Tau Therapeutic Strategies for the Treatment of Alzheimer's Disease," Current Topics in Medicinal Chemistry, 6(6):579-595 (2006).
El-Amraoui, A. et al., "Usher I Syndrome: unravelling the mechanisms that underlie the cohesion of the growing hair bundle in inner ear sensory cells," Journal of Cell Science, 118(20):4593-4603 (2005).
Geng, R. et al., "The mechanosensory structure of the hair cell requires clarin-1, a protein encoded by Usher syndrome III causative gene," J. Neurosci, Jul. 11, 2012;32(28):9485-9498. doi: 10.1523/JNEUROSCI.0311-12.2012.
Geng, R. et al., "Usher syndrome IIIA gene clarin-1 is essential for hair cell function and associated neural activation," Hum. Mol. Genet., Aug. 1, 2009;18(15):2748-60. doi: 10.1093/hmg/ddp210. Epub May 3, 2009.
Geng, R. et al., "Noddy, a Mouse Harboring a Missense Mutation in Protocadherin-15, Reveals the Impact of Disrupting a Critical Interaction Site between Tip-Link Cadherins in Inner Ear Hair Cells," The Journal of Neuroscience, Mar. 6, 2013, 33(10): 4395-4404; doi: 10.1523/JNEUROSCI.4514-12.2013.
Tian, G. et al., "Clarin-1, encoded by the Usher Syndrome III causative gene, forms a membranous microdomain: possible role of clarin-1 in organizing the actin cytoskeleton," The Journal of Biological Chemistry, 284(28):18980-18993 (2009).
Tian, G. et al., "Impairment of vision in a mouse model of Usher Syndrome Type III," Investigative Ophthalmology & Visual Science Mar. 2016, vol. 57, 866-875. doi:10.1167/iovs.15-16946.
Tretyakov, E. V. et al., "Investigations of the Richter reaction in a series of vicinal alkynylpyrazolediazonium salts," J. Chem. Soc., Perkin Trans., 1(24):3721-3726 (1999).
Tretyakov, E. V. et al., "New findings in the Richter reaction in series of vicinal alkynylpyrazolyldiazonium salts," Heterocyclic Communications, 4(6):519-524 (1998).
Vasilevsky, S. F. et al., "Cinnolines and pyrazolopyridazines. Novel synthetic and mechanistic aspects of the Richter reaction," Liebigs Ann., (5):775-779 (1995).

* cited by examiner

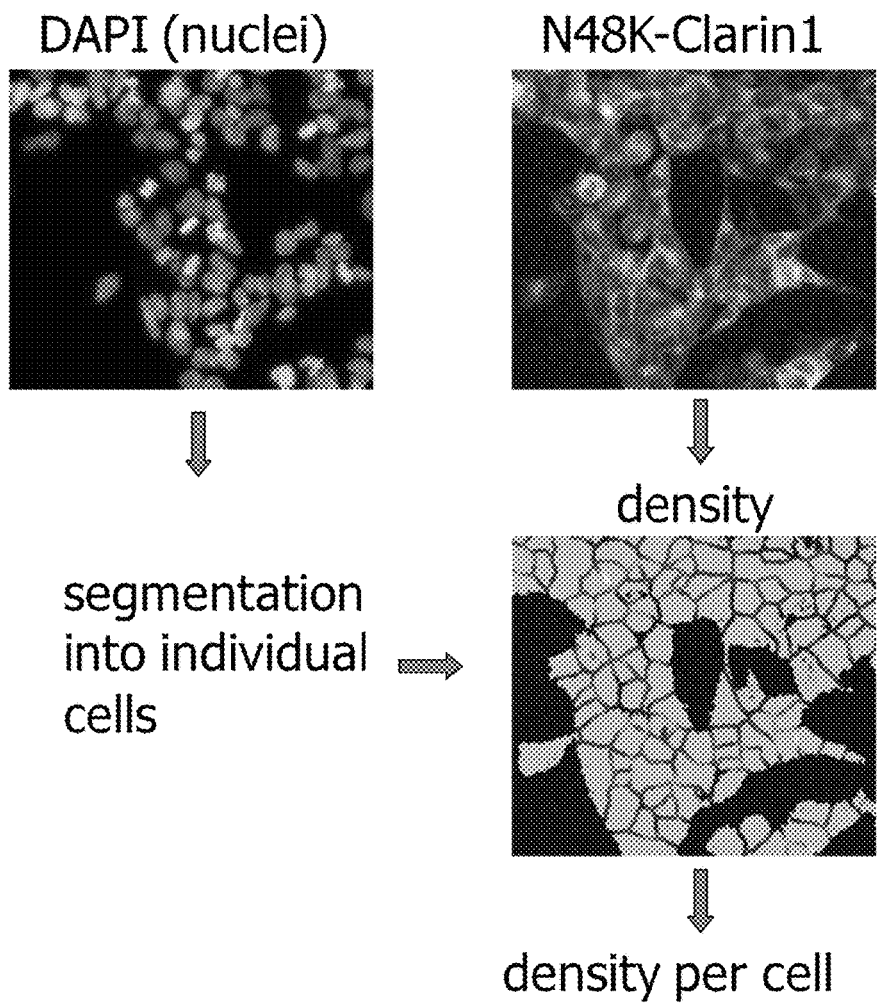
High content analysis. DAPI-stained nuclei are used to perform segmentation of the image into individual cells. The density observed in the N48K Clarin-1 channel (Cy3) is then calculated per cell and averaged over a field.

PYRAZOLOPYRIDAZINES AND METHODS FOR TREATING RETINAL-DEGENERATIVE DISEASES AND HEARING LOSS ASSOCIATED WITH USHER SYNDROME

This application is a continuation of U.S. application Ser. No. 15/375,959, filed Dec. 12, 2016, which is a continuation of U.S. application Ser. No. 14/980,347, filed Dec. 28, 2015, now U.S. Pat. No. 9,549,910, which is a continuation of U.S. application Ser. No. 14/730,994, filed Jun. 4, 2015, now U.S. Pat. No. 9,260,381, which is a division of U.S. application Ser. No. 13/791,205, filed Mar. 8, 2013, now U.S. Pat. No. 9,079,909, which is a continuation of International Patent Application No. PCT/US2012/34959, filed on Apr. 25, 2012, which claims the benefit of U.S. Provisional Application No. 61/478,642, filed Apr. 25, 2011, U.S. Provisional Application No. 61/537,908, filed Sep. 22, 2011, and U.S. Provisional Application No. 61/576,471, filed Dec. 16, 2011, the disclosure of each of which is hereby incorporated by reference herein in its entirety.

BACKGROUND OF THE INVENTION

Usher Syndrome, a rare genetic disorder and a leading cause of deafness and blindness, is associated with a mutation in any one of ten genes. Other names for the syndrome include Hallgren Syndrome, Usher-Hallgren Syndrome, RP-Dysacusis Syndrome, and Dystrophia Retinae Dysacusis Syndrome.

Usher Syndrome is characterized by deafness and gradual vision loss. The hearing loss is associated with inner ear defects, whereas the vision loss is associated with retinitis pigmentosa (RP), a degeneration of the retinal cells. Usually, the rod cells of the retina are affected first, leading to early night blindness and the gradual loss of peripheral vision. Some cases involve early degeneration of the cone cells of the macula, leading to a loss of central acuity. In some cases, the sufferer's foveal vision is spared, leading to "doughnut vision," in which central and peripheral vision remain intact, but interrupted by a ring of blindness.

Usher Syndrome has three clinical subtypes, denoted: I, II and III. Usher I subjects are born profoundly deaf, begin to lose vision within ten years and exhibit balance difficulties. They are slow to learn to walk as children, due to vestibular abnormalities. Usher II subjects suffer lesser hearing loss, do not suffer physical imbalance and begin to lose vision in adolescence. Much of their hearing can be preserved into middle age. Usher III subjects suffer gradual loss of hearing and vision and can suffer physical imbalance.

Usher Syndrome is a variable condition; the degree of severity is not tightly linked to subtype. For example, an Usher III subject might be asymptomatic in childhood, but develop profound hearing and vision loss by early to mid adulthood. Substantial visual impairment prior to age 50 is common in Usher III subjects. An Usher I subject, on the other hand, might be deaf from birth, but sustain good central vision into old age.

SUMMARY OF THE INVENTION

The invention provides compounds of Formula I:

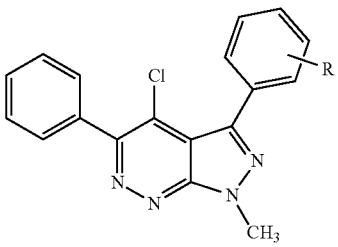

Formula I and pharmaceutically acceptable salts thereof, wherein R is fluoro, chloro, iodo, methyl, methoxy, cyano, trifluoromethyl, or —(CO)NH(CH$_3$).

The invention also provides compounds of Formula II:

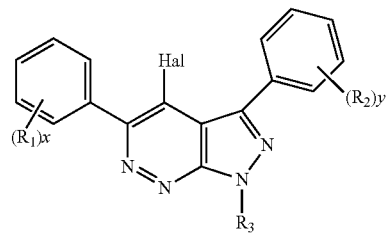

Formula II and pharmaceutically acceptable salts thereof, wherein Hal is —Cl, —F, —I, or —Br;

x is an integer ranging from 0 to 5;

each R$_1$ is independently —Cl, —F, —I, —Br, —C$_1$-C$_3$ alkyl, —O—C$_1$-C$_3$ alkyl, —CN, —CF$_3$, —C(O)NH(CH$_3$), or —CCCH$_2$OH;

y is an integer ranging from 0 to 5;

each R$_2$ is independently —Cl, —F, —Br, —C$_1$-C$_3$ alkyl, —O—C$_1$-C$_3$ alkyl, —CN, —CF$_3$, —C(O)NH(CH$_3$), or —CCCH$_2$OH;

R$_3$ is —H, —C$_1$-C$_6$ alkyl, —(C$_1$-C$_6$ alkylene)-OH, —(C$_1$-C$_6$ alkylene)-phenyl, —(C$_1$-C$_6$ alkylene)-O—(C$_1$-C$_6$ alkyl), —C$_2$-C$_6$ alkenyl, —(C$_1$-C$_6$ alkylene)-C(O)R$_4$, —(C$_1$-C$_6$ alkylene)-R$_5$

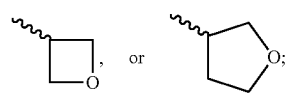

R$_4$ is —OH, —O—(C$_1$-C$_6$ alkyl), —NH$_2$, —NH(C$_1$-C$_6$ alkyl), —NH((C$_1$-C$_6$ alkylene)-OH), —NH((C$_1$-C$_6$ alkylene)N(C$_1$-C$_6$ alkyl)$_2$), —N(C$_1$-C$_6$ alkyl)((C$_1$-C$_6$ alkylene)-CN), —N(C$_1$-C$_6$ alkyl)((C$_1$-C$_6$ alkylene)N(C$_1$-C$_6$ alkyl)$_2$), —NH(C$_1$-C$_6$ alkylene)-O—(C$_1$-C$_6$ alkyl), a is an integer ranging from 0 to 10;
b is an integer ranging from 0 to 8;
c is an integer ranging from 0 to 6; and
$R_5$ is The invention additionally provides compounds of Formula III:

Formula III and pharmaceutically acceptable salts thereof,
wherein Hal is —Cl, —F, —I, or —Br;
x is an integer ranging from 0 to 5;
each $R_1$ is independently —Cl, —F, —I, —Br, —$C_1$-$C_3$ alkyl, —O—$C_1$-$C_3$ alkyl, —CN, —$CF_3$, —C(O)NH($CH_3$), or —CCCH$_2$OH;
$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$ alkyl), —$C_2$-$C_6$ alkenyl, —($C_1$-$C_6$ alkylene)-C(O)$R_4$, —($C_1$-$C_6$ alkylene)-$R_5$, or $R_4$ is —OH, —O—($C_1$-$C_6$ alkyl), —$NH_2$, —NH($C_1$-$C_6$ alkyl), —NH(($C_1$-$C_6$ alkylene)-OH), —NH(($C_1$-$C_6$ alkylene)N($C_1$-$C_6$ alkyl)$_2$), —N($C_1$-$C_6$ alkyl)(($C_1$-$C_6$ alkylene)-CN), —N($C_1$-$C_6$ alkyl)(($C_1$-$C_6$ alkylene)N($C_1$-$C_6$ alkyl)$_2$), —NH($C_1$-$C_6$ alkylene)-O—($C_1$-$C_6$ alkyl),

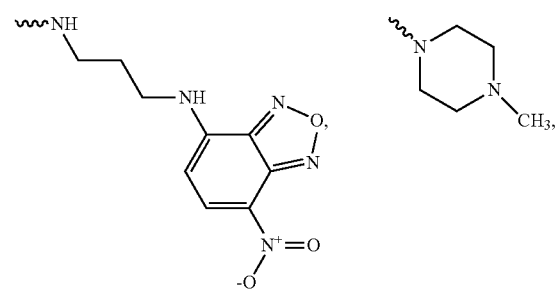
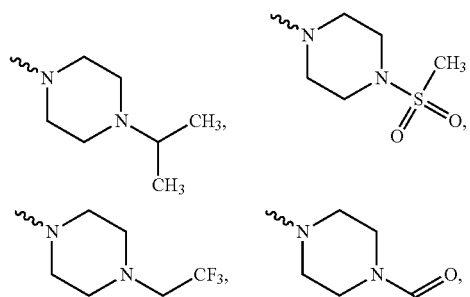
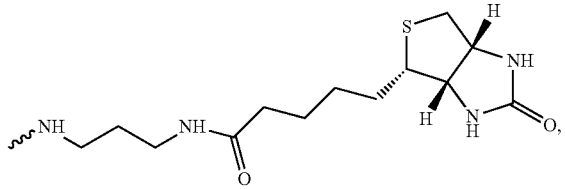
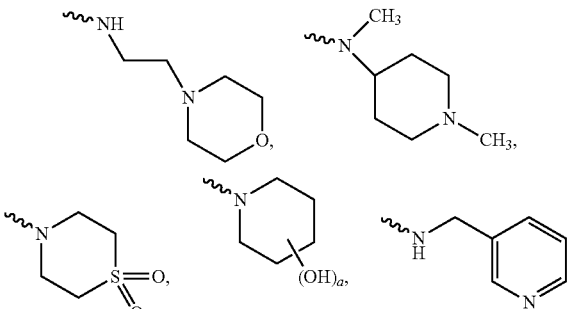
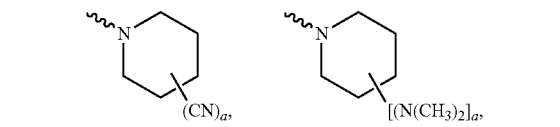
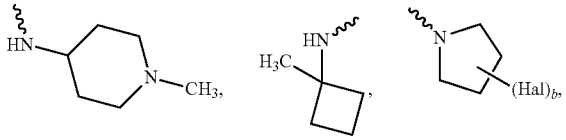
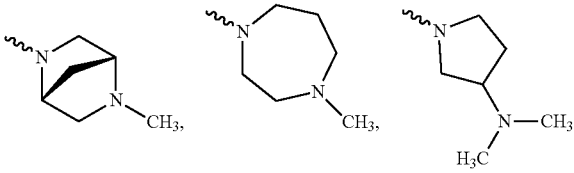
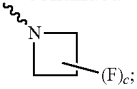
a is an integer ranging from 0 to 10;
b is an integer ranging from 0 to 8;
c is an integer ranging from 0 to 6;
$R_5$ is
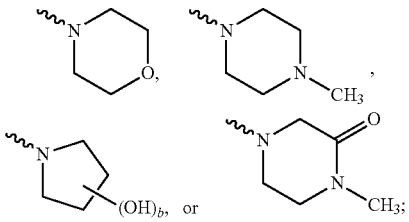
wherein each $R_6$ and $R_7$ is independently —H or —I, wherein at least one of $R_6$ and $R_7$ is —I,
and wherein when $R_3$ is —$C_1$-$C_3$ alkyl, $R_7$ is —H.
The invention further provides compounds having the following structures:
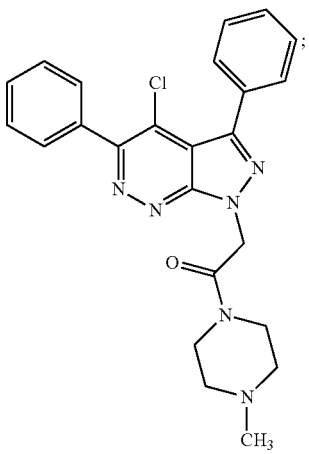
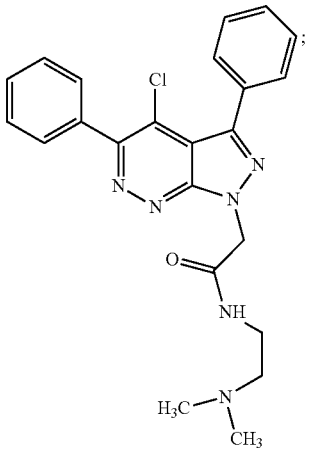

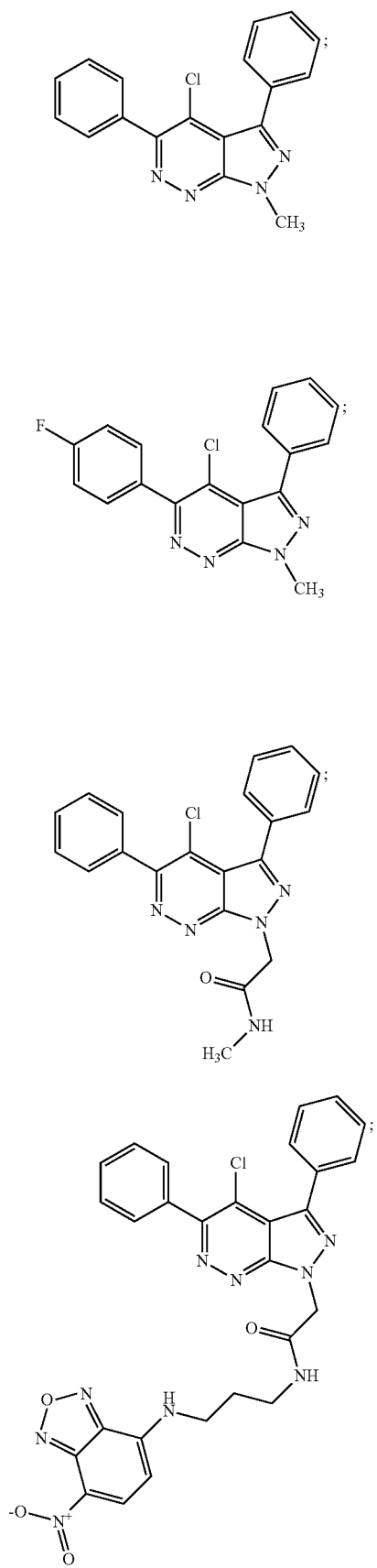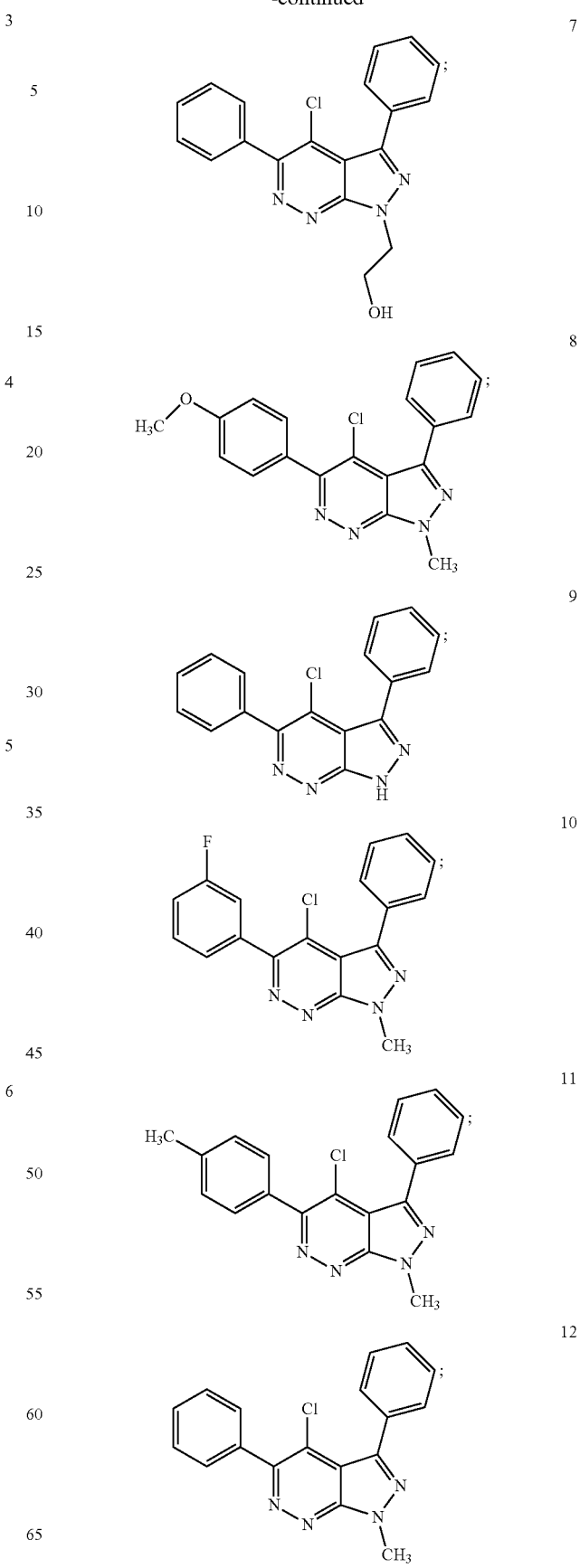

13
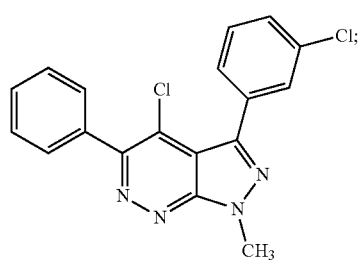
14
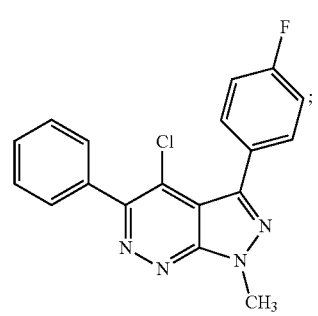
15
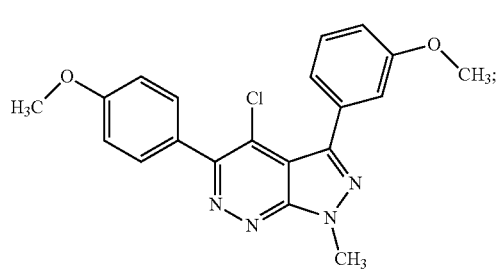
16
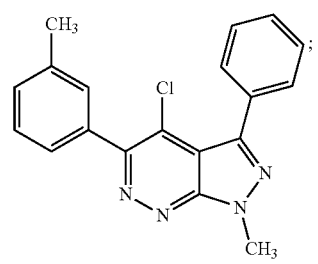
17
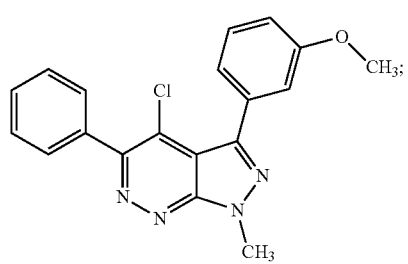
18
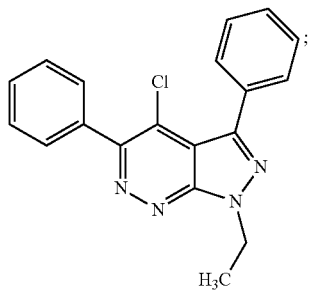
19
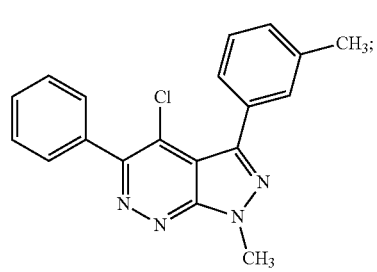
20
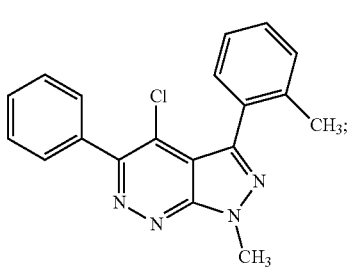
21
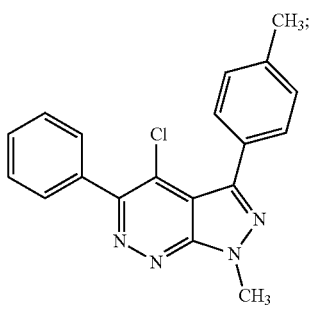
22
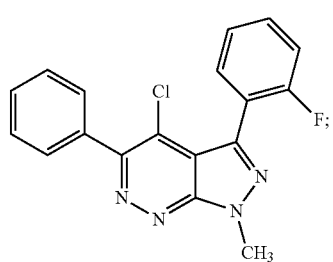

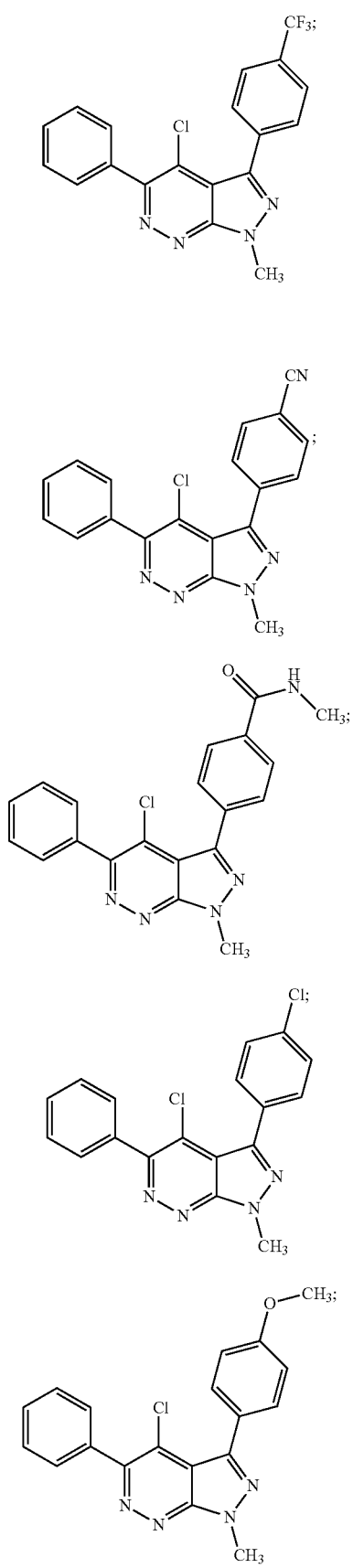
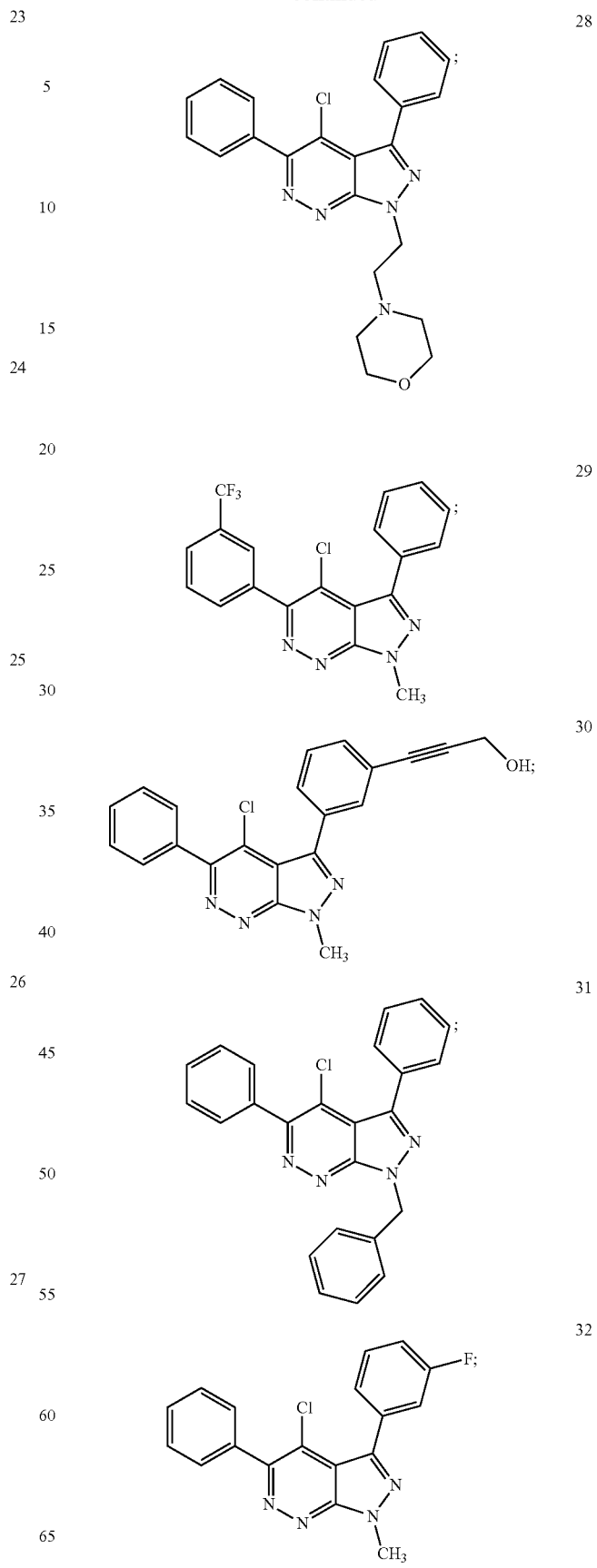

33
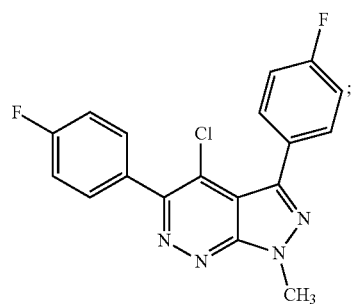
34
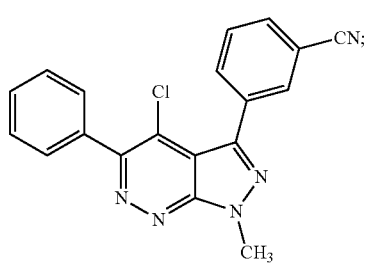
35
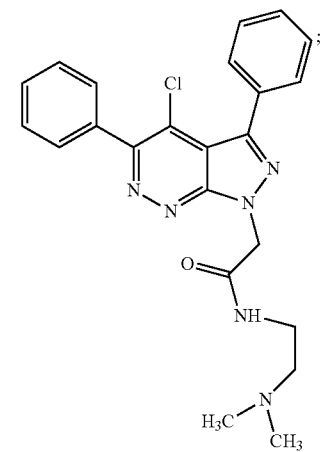
37
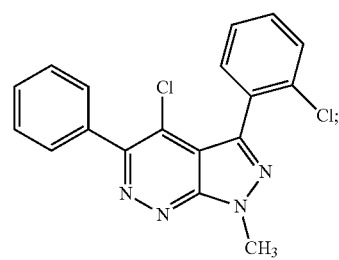
38
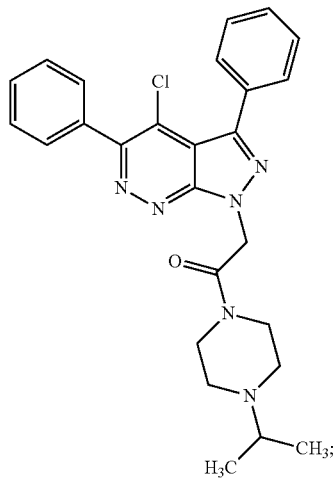
39
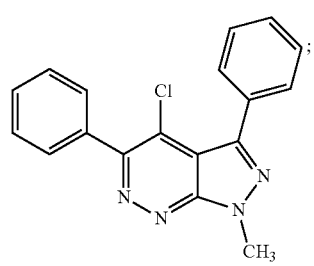
42
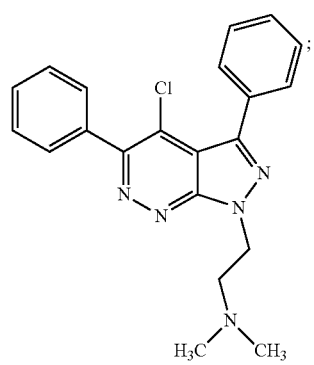
45
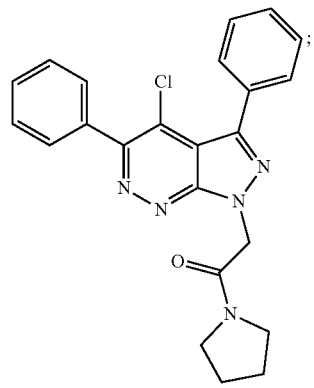

47
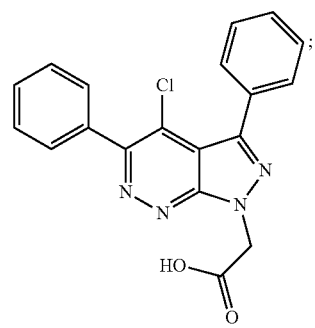
48
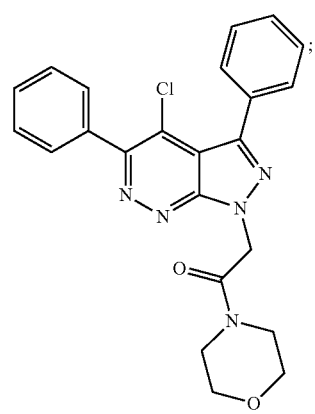
49
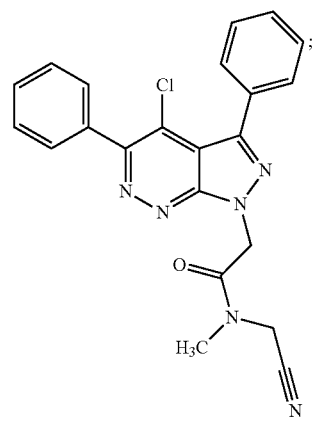
50
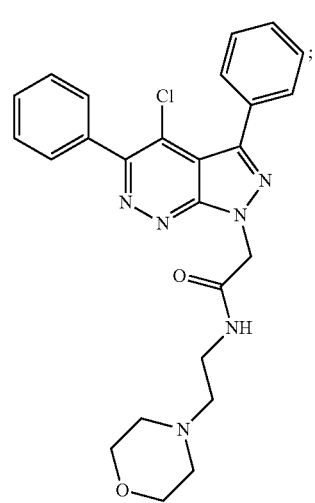
51
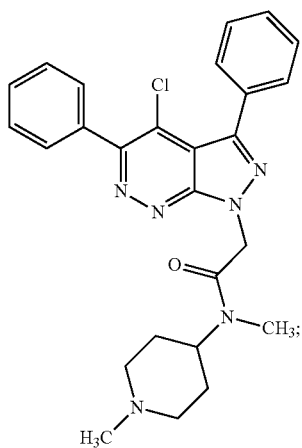
52
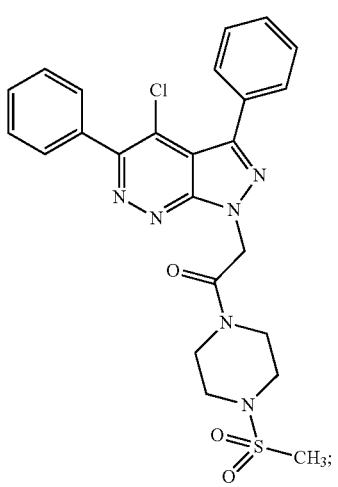
53
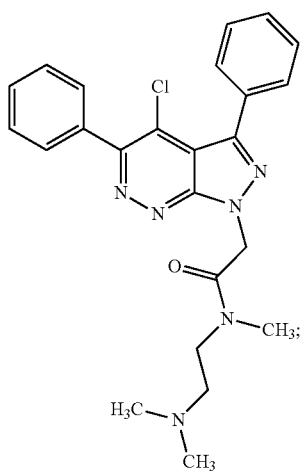

54
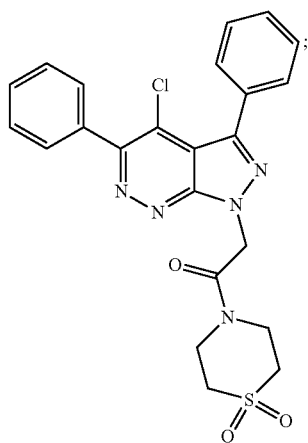
55
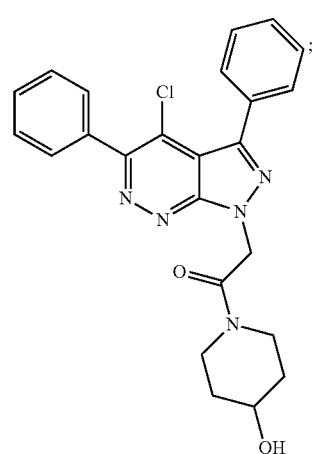
56
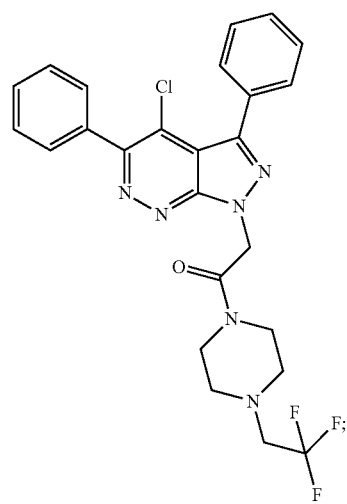
57
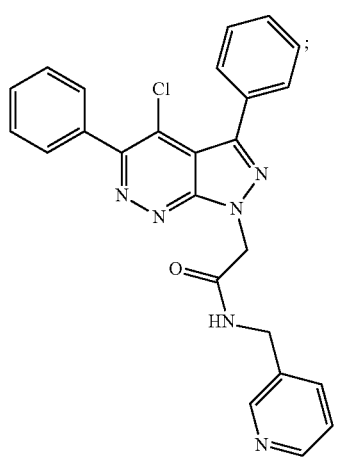
58
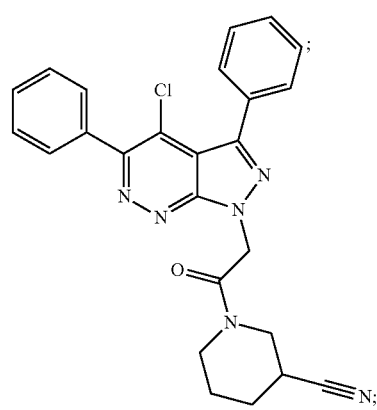
59
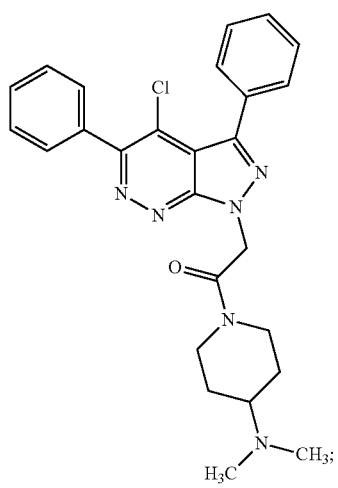

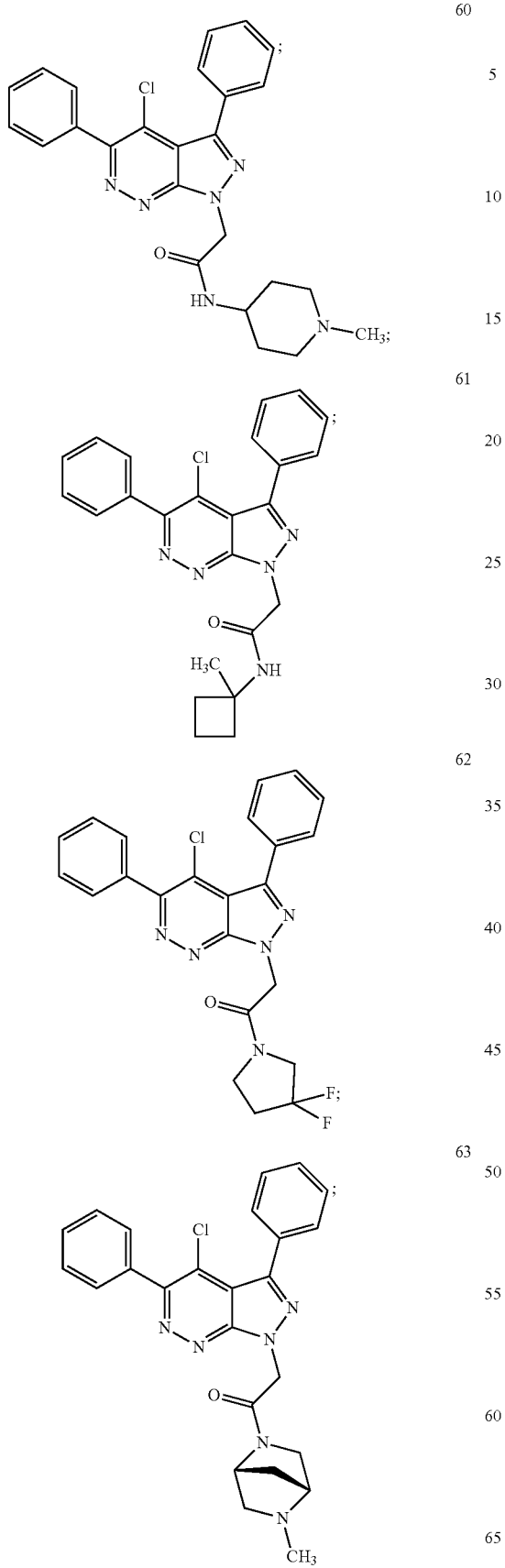
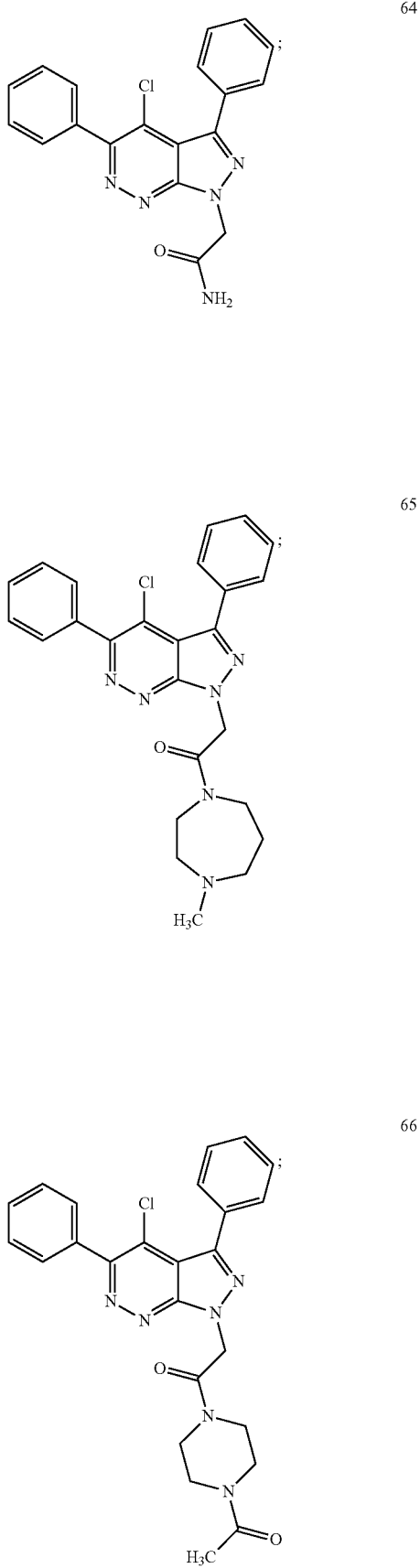

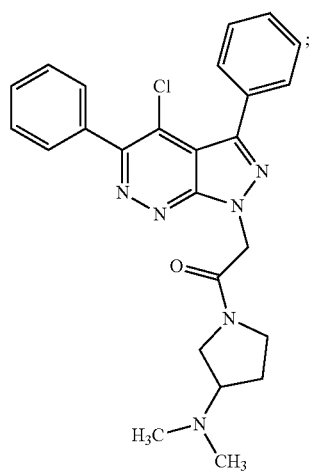
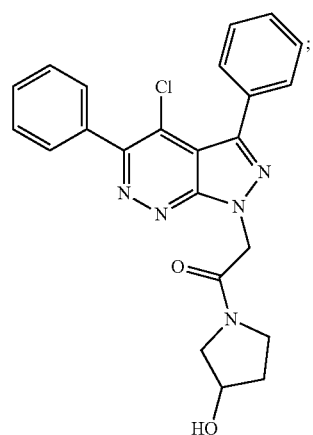
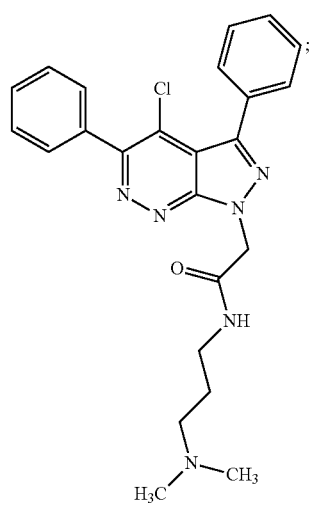
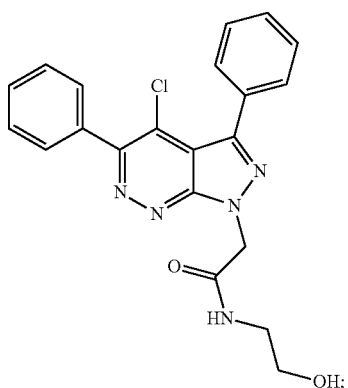
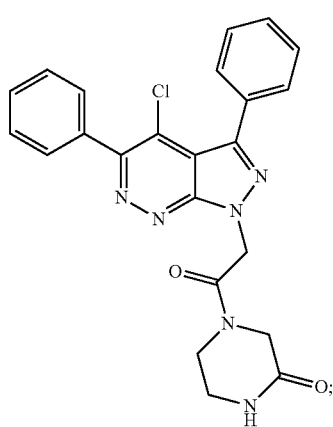
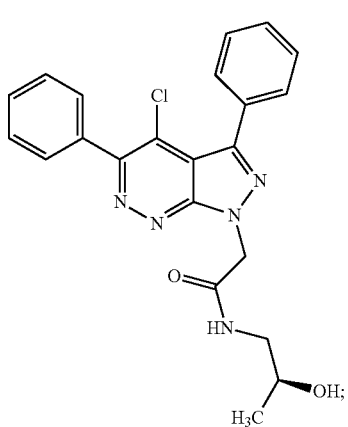

73
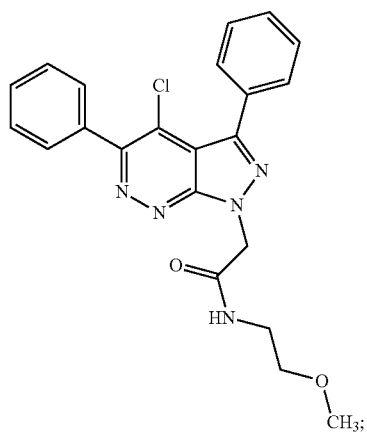
74
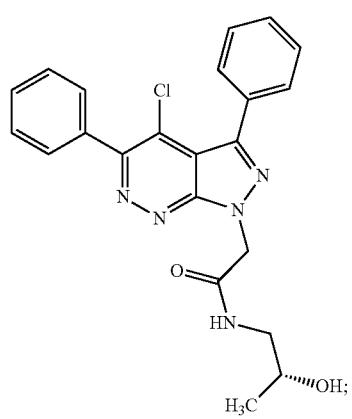
75
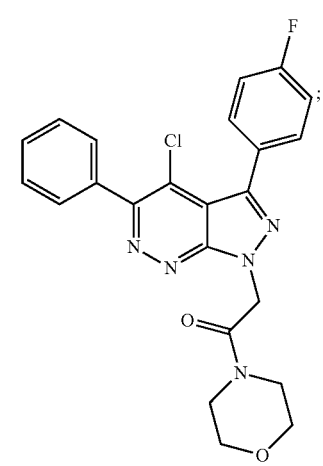
76
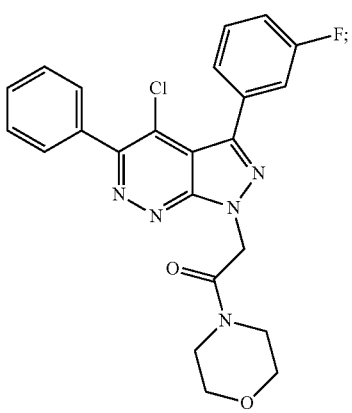
77
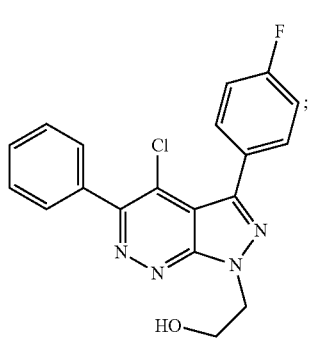
78
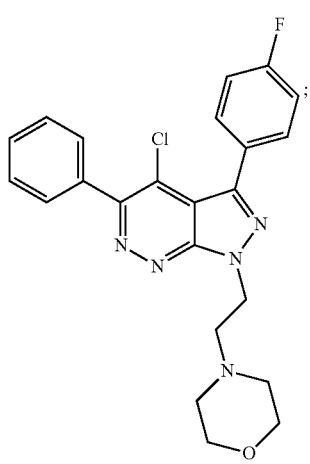
79
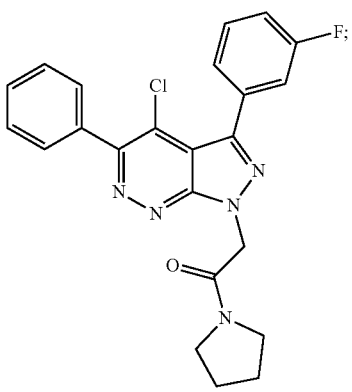

80
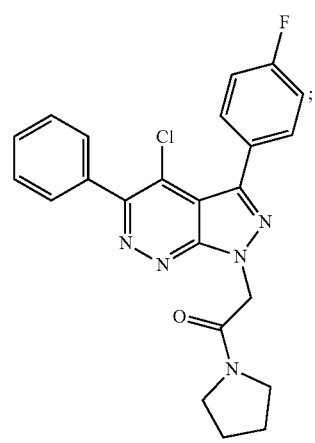
81
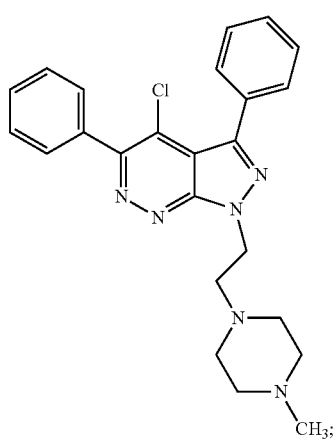
82
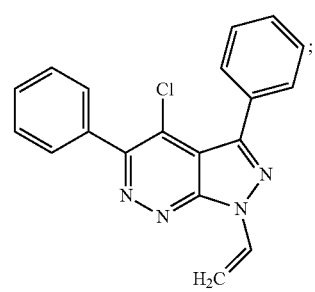
83
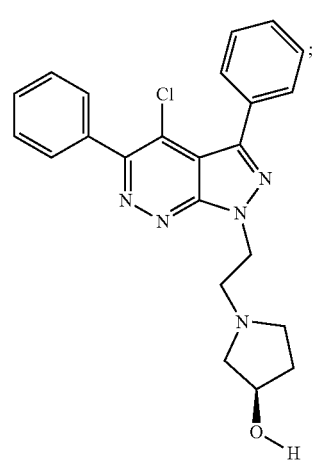
84
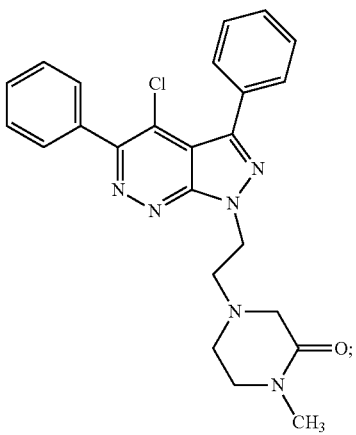
85
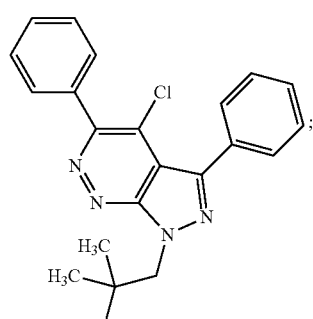
86
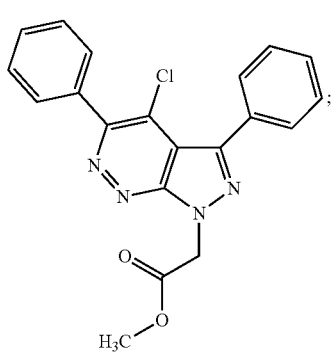
87
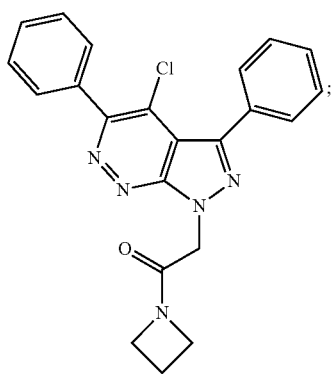

-continued
88
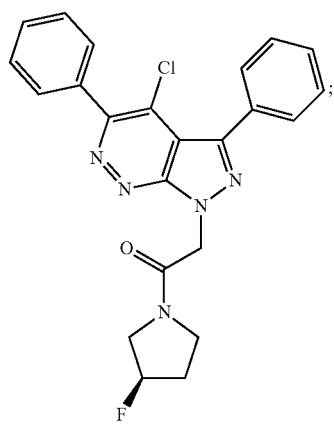
89
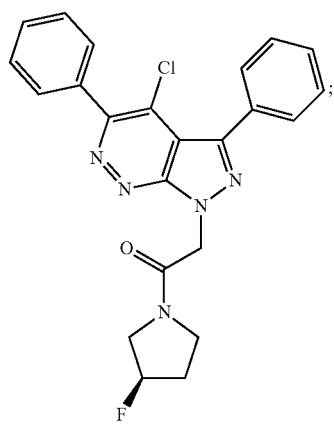
90
91
-continued
92
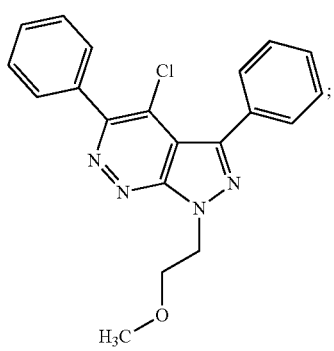
93
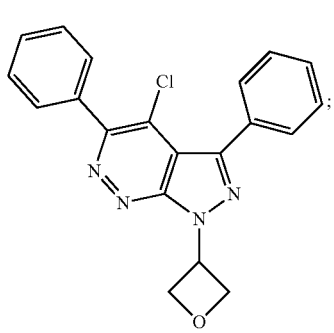
94
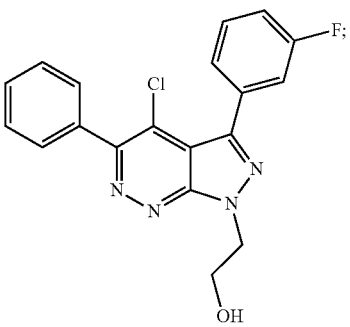
95
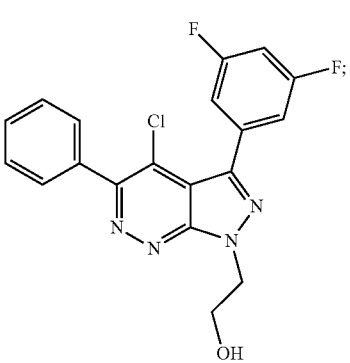

-continued

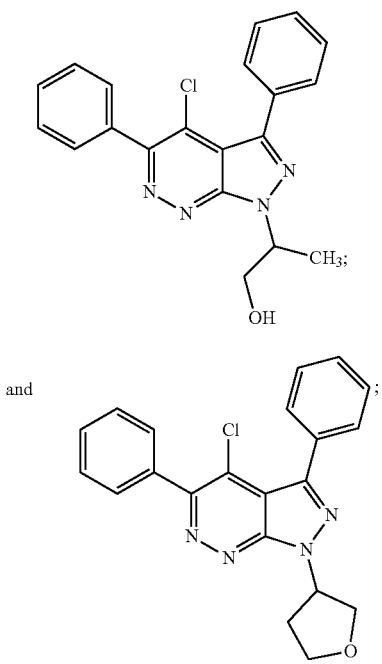

96 and

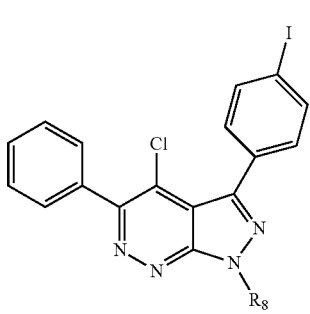

97 and pharmaceutically acceptable salts thereof.

Compounds 1-35, 37-39, 42, 45, and 47-97 are illustrative compounds of Formula II.

Each of the compounds of Formulas I, II, and III and above compounds 1-35, 37-39, 42, 45, and 47-97, or a pharmaceutically acceptable salt thereof, (a "Pyrazolopyridazine compound") is useful for treating a retinal degenerative disease or hearing loss associated with Usher Syndrome.

The invention further provides compositions comprising an effective amount of a Pyrazolopyridazine compound and a pharmaceutically acceptable carrier or vehicle. The compositions are useful for treating a retinal degenerative disease or hearing loss associated with Usher Syndrome.

The invention further provides methods for treating a retinal degenerative disease, comprising administering to a subject in need thereof an effective amount of a Pyrazolopyridazine compound.

The invention still further provides methods for treating hearing loss associated with Usher Syndrome, comprising administering to a subject in need thereof an effective amount of a Pyrazolopyridazine compound.

The invention still further provides compounds of Formula IV:

Formula IV

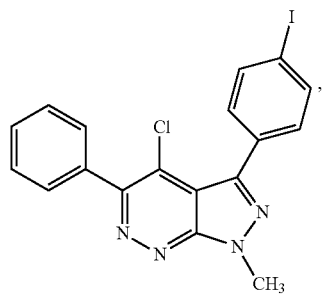 [SMILES: Cn1nc(-c2ccc(I)cc2)c2c(Cl)c(-c3ccccc3)nnc21]

and salts thereof,
wherein $R_5$ is —$C_1$-$C_3$ alkyl.

The invention still further provides Compound 43, an illustrative compound of Formula IV, which has the structure:

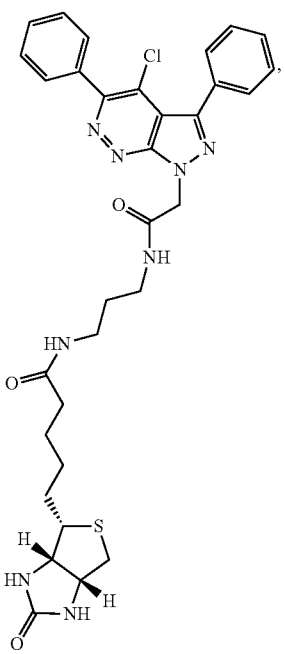 [SMILES: O=C(CCCC[C@@H]1SC[C@@H]2NC(=O)N[C@@H]21)NCCCNC(=O)Cn1nc(-c2ccccc2)c2c(Cl)c(-c3ccccc3)nnc21]

and salts thereof.

Compounds of Formula IV and salts thereof are useful as intermediates for synthesizing Pyrazolopyridazine compounds.

The invention still further provides Compound 44, which has the structure:

and salts thereof.

Compound 44 is useful as a probe for identifying proteins that bind to its bisphenyl pyrazolopyridazine moiety.

The invention still further provides Compound 46, which has the structure:

and pharmaceutically acceptable salts thereof.

Compound 46 or a pharmaceutically acceptable salt thereof is also useful for treating a retinal degenerative disease or hearing loss associated with Usher Syndrome.

The invention further provides compositions comprising an effective amount of Compound 46, or a pharmaceutically acceptable salt thereof, and a pharmaceutically acceptable carrier or vehicle. The compositions are useful for treating a retinal degenerative disease or hearing loss associated with Usher Syndrome.

The invention further provides methods for treating a retinal degenerative disease, comprising administering to a subject in need thereof an effective amount of Compound 46 or a pharmaceutically acceptable salt thereof.

The invention still further provides methods for treating hearing loss associated with Usher Syndrome comprising, administering to a subject in need thereof an effective amount of Compound 46 or a pharmaceutically acceptable salt thereof.

Each of the following is a "compound of the invention": a Pyrazolopyridazine compound; Compound 1-35, 37-39 or 42-97, or a salt thereof and a compound having the structure of Formula I, II, or III, or a salt thereof.

BRIEF DESCRIPTION OF THE FIGURE

FIG. 1 illustrates density of N48K Clarin-1 expression in cells.

DETAILED DESCRIPTION OF THE INVENTION

The invention provides compounds of the invention, compositions comprising a compound of the invention, and methods for treating a retinal degenerative disease or hearing loss associated with Usher Syndrome, comprising administering a Pyrazolopyridazine compound or Compound 46 or a pharmaceutically acceptable salt thereof.

Compounds of the Invention

The term "alkyl" refers to a straight or branched saturated hydrocarbon group. Illustrative alkyl groups include $-CH_3$, $-CH_2CH_3$, $-CH_2CH_2CH_3$, $-CH(CH_3)_2$, $-CH_2CH_2CH_2CH_3$, $-CH(CH_3)CH_2CH_3$, $-CH_2CH(CH_3)_2$, $-C(CH_3)_3$, $-CH_2CH_2CH_2CH_2CH_3$, $-CH(CH_3)CH_2CH_2CH_3$, $-CH_2CH_2CH(CH_3)_2$, $-CH_2C(CH_3)_3$, $-CH_2CH_2CH_2CH_2CH_3$, $-CH(CH_3)CH_2CH_2CH_3$, $-CH_2CH_2CH(CH_3)_2$ and $-CH(CH_3)C(CH_3)_3$ groups.

The term "alkylene" refers to an alkyl group bonded to another atom or group. Illustrative alkylene groups include $-CH_2-$, $-CH_2CH_2-$, $-CH_2CH_2CH_2-$, $-C(CH_3)_2-$, $-CH(CH_3)-$, $-CH_2CH_2CH_2-$, $-CH(CH_3)CH_2CH_2-$, $-CH_2C(CH_3)_2-$, $-C(CH_3)_2CH_2-$, $-CH_2CH_2CH_2CH_2-$, $-CH(CH_3)CH_2CH_2CH_2-$, $-CH_2CH_2C(CH_3)_2-$, $-CH_2CH(CH_3)CH_2CH_2-$, $-CH_2CH_2CH(CH_3)CH_2-$, $-CH_2CH_2CH_2CH_2CH_2-$, $-CH(CH_3)CH_2CH_2CH_2CH_2-$, $-CH_2CH_2CH_2C(CH_3)_2-$, $-CH_2CH(CH_3)CH_2CH_2CH_2-$, $-CH_2CH_2CH_2CH(CH_3)CH_2-$ and $-C(CH_3)_2C(CH_3)_2-$ groups.

The term "alkenyl" refers to a straight or branched hydrocarbon group having one or more double bonds. Illustrative alkenyl groups include $-CH=CH_2$, $-CH_2CH=CH_2$, cis $-CH=CHCH_3$, trans $-CH=CHCH_3$, $-C(CH_3)=CH_2$, cis $-CH=CHCH_2CH_3$, trans $-CH=CHCH_2CH_3$, cis $-CH_2CH=CHCH_3$, trans $-CH_2CH=CHCH_3$, $-CH_2CH_2CH=CH_2$, cis $-CH=CHCH_2CH_2CH_3$, trans $-CH=CHCH_2CH_2CH_3$, cis $-CH_2CH_2CH=CHCH_3$, trans $-CH_2CH_2CH=CHCH_3$, $-CH_2CH_2CH_2CH=CH_2$, $-CH_2CH=C(CH_3)_2$, cis $-CH=CHCH_2CH_2CH_2CH_3$, trans $-CH=CHCH_2CH_2CH_2CH_3$, cis $-CH_2CH_2CH_2CH=CHCH_3$, trans $-CH_2CH_2CH_2CH=CHCH_3$, $-CH_2CH_2CH_2CH_2CH=CH_2$, and $-CH_2CH_2CH=C(CH_3)_2$, groups.

The word "about" when immediately preceding a numerical value means a range of plus or minus 10% of that value, e.g., "about 100 mg" means 90 mg to 110 mg, "about 300 mg" means 270 mg to 330 mg, etc.

Abbreviations:
APCI Atmospheric Pressure Chemical Ionization
DAPI 4',6-diamidino-2-phenylindole
DIPEA diisopropylethylamine
DMEM Dulbecco's Modified Eagle Medium
DMF dimethylformamide
DMSO Dimethyl sulfoxide
EDAC 1-(3-dimethylaminopropyl)-3-ethylcarbodiimide hydrochloride
ESI Electrospray ionization
ESI-TOF Electrospray ionization-Time-of-flight
HATU 2-(7-Aza-1H-benzotriazole-1-yl)-1,1,3,3-tetramethyluronium hexafluorophosphate
HOPO 2-hydroxypyridine-N-oxide
HPLC High-performance liquid chromatography
LCMS Liquid chromatography-mass spectrometry
LDA lithium diisopropyl amide
m/z Mass-to-charge ratio
MALDI-TOF Matrix Assisted Laser Desorption Ionization-Time-of-flight
MS Mass spectrometry
PBS phosphate-buffered saline
Rt Retention time
SDS sodium dodecylsulfate
THF tetrahydrofuran Compounds of Formula I In one embodiment, the Pyrazolopyridazine compound is a compound of Formula I:

Formula I

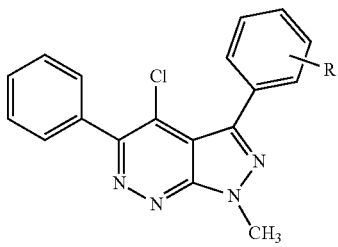

or a pharmaceutically acceptable salt thereof,
wherein R is fluoro, chloro, iodo, methyl, methoxy, cyano, trifluoromethyl, or —(CO)NH(CH$_3$). In one embodiment, R of Formula I is in the para position relative to the pyrazolopyridazino ring system. In one embodiment, R of Formula I is in the meta position relative to the pyrazolopyridazino ring system. In one embodiment, R of Formula I is in the ortho position relative to the pyrazolopyridazino ring system.

Compounds of Formula II

The invention also provides compounds of Formula II:

Formula II

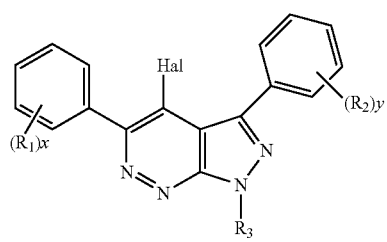

and pharmaceutically acceptable salts thereof,
wherein Hal is —Cl, —F, —I, or —Br;
x is an integer ranging from 0 to 5;
each $R_1$ is independently —Cl, —F, —I, —Br, —C$_1$-C$_3$ alkyl, —O—C$_1$-C$_3$ alkyl, —CN, —CF$_3$, —C(O)NH (CH$_3$), or —CCCH$_2$OH;
y is an integer ranging from 0 to 5;
each $R_2$ is independently —Cl, —F, —Br, —C$_1$-C$_3$ alkyl, —O—C$_1$-C$_3$ alkyl, —CN, —CF$_3$, —C(O)NH(CH$_3$), or —CCCH$_2$OH;
$R_3$ is —H, —C$_1$-C$_6$ alkyl, —(C$_1$-C$_6$ alkylene)-OH, —(C$_1$-C$_6$ alkylene)-phenyl, —(C$_1$-C$_6$ alkylene)-O—(C$_1$-C$_6$ alkyl), —C$_2$-C$_6$ alkenyl, —(C$_1$-C$_6$ alkylene)-C(O)R$_4$, —(C$_1$-C$_6$ alkylene)-R$_5$,

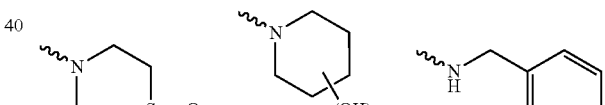

$R_4$ is —OH, —O—(C$_1$-C$_6$ alkyl), —NH$_2$, —NH(C$_1$-C$_6$ alkyl), —NH((C$_1$-C$_6$ alkylene)-OH), —NH((C$_1$-C$_6$ alkylene)N(C$_1$-C$_6$ alkyl)$_2$), —N(C$_1$-C$_6$ alkyl)((C$_1$-C$_6$ alkylene)-CN), —N(C$_1$-C$_6$ alkyl)((C$_1$-C$_6$ alkylene)N (C$_1$-C$_6$ alkyl)$_2$), —NH(C$_1$-C$_6$ alkylene)-O—(C$_1$-C$_6$ alkyl),

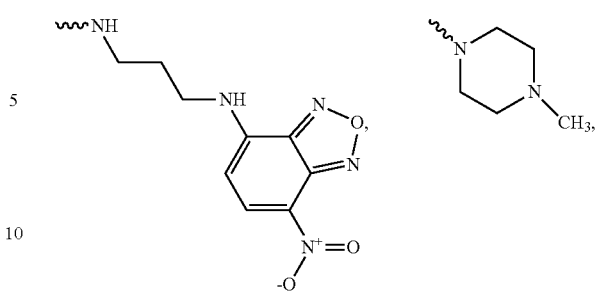

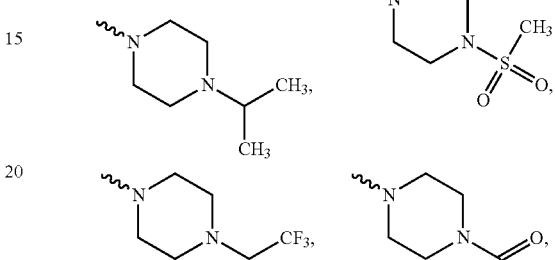

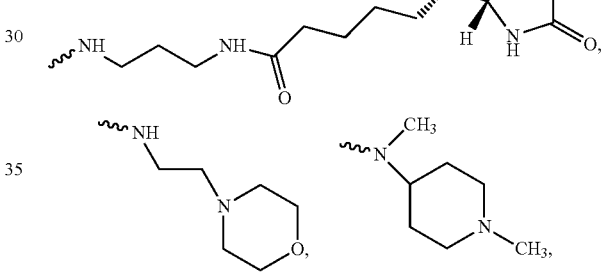

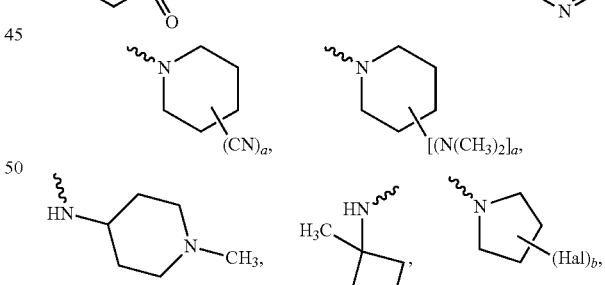

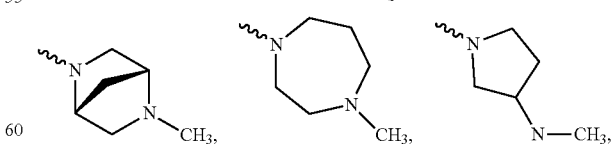

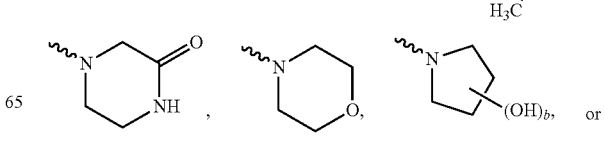

or

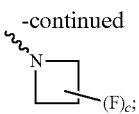

a is an integer ranging from 0 to 10;
b is an integer ranging from 0 to 8;
c is an integer ranging from 0 to 6; and
$R_5$ is

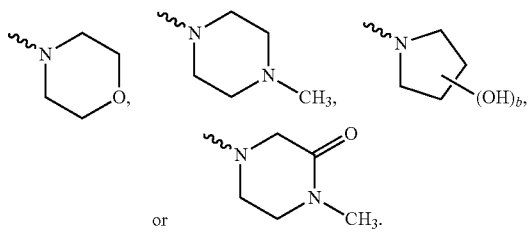

In certain embodiments, Hal is —Cl. In yet another embodiment, x and y are 0.

In certain embodiments, x and y are 0, x is 0 and y is 1, x is 1 and y is 2, x is 1 and y is 0, x is 1 and y is 1, x is 1 and y is 2, x is 2 and y is 0, x is 2 and y is 1, or x is 2 and y is 2.

In certain embodiments, Hal is —Cl and: x and y are 0, x is 0 and y is 1, x is 1 and y is 2, x is 1 and y is 0, x is 1 and y is 1, x is 1 and y is 2, x is 2 and y is 0, x is 2 and y is 1, or x is 2 and y is 2.

In particular embodiments, x is 1 and $R_1$ is in the ortho position relative to the pyrazolopyridazino ring system. In certain embodiments, x is 1 and $R_1$ is in the para position relative pyrazolopyridazino ring system. In further embodiments, x is 1 and $R_1$ is in the meta position relative pyrazolopyridazino ring system.

In particular embodiments, y is 1 and $R_2$ is in the ortho position relative pyrazolopyridazino ring system. In certain embodiments, y is 1 and $R_2$ is in the para position relative pyrazolopyridazino ring system. In further embodiments, y is 1 and $R_2$ is in the meta position relative pyrazolopyridazino ring system.

In particular embodiments, x is 2 and $R_1$ is in the ortho and meta position relative pyrazolopyridazino ring system. In certain embodiments, x is 2 and $R_1$ is in the ortho and para position relative pyrazolopyridazino ring system. In further embodiments, x is 2 and $R_1$ is in the para and meta position relative pyrazolopyridazino ring system.

In particular embodiments, y is 2 and $R_2$ is in the ortho and meta position relative pyrazolopyridazino ring system. In certain embodiments, y is 2 and $R_2$ is in the ortho and para position relative pyrazolopyridazino ring system. In further embodiments, y is 2 and $R_2$ is in the para and meta position relative pyrazolopyridazino ring system.

In yet other embodiments, $R_1$ is chloro. In certain embodiments, $R_1$ is fluoro. In certain embodiments, $R_1$ is iodo. In other embodiments, $R_1$ is —Br. In further embodiments, $R_1$ is —OCH$_3$. In other embodiments, $R_1$ is —CH$_3$. In yet other embodiments, $R_1$ is —C(O)N(H)CH$_3$. In certain embodiments, $R_1$ is —CF$_3$. In further embodiments, $R_1$ is —CN. In additional embodiments, $R_1$ is —C≡CCH$_2$OH.

In yet other embodiments, x is 1 or 2, and $R_1$ is —Cl, —F, —I, —Br, —OCH$_3$, —CH$_3$, —C(O)N(H)CH$_3$, —CF$_3$, —CN or —C≡CCH$_2$OH.

In yet other embodiments, Hal is —Cl, x is 1 or 2, and $R_1$ is —Cl, —F, —I, —Br, —OCH$_3$, —CH$_3$, —C(O)N(H)CH$_3$, —CF$_3$, —CN or —C≡CCH$_2$OH.

In yet other embodiments, $R_2$ is —Cl. In certain embodiments, $R_2$ is —F. In other embodiments, $R_2$ is —Br. In further embodiments, $R_2$ is —OCH$_3$. In other embodiments, $R_2$ is —CH$_3$. In yet other embodiments, $R_2$ is —C(O)N(H)CH$_3$. In certain embodiments, $R_2$ is —CF$_3$. In further embodiments, $R_2$ is —CN. In additional embodiments, $R_2$ is —C≡CCH$_2$OH.

In yet other embodiments, y is 1 or 2, and $R_2$ is —Cl, —F, —Br, —OCH$_3$, —CH$_3$, —C(O)N(H)CH$_3$, —CF$_3$, —CN or —C≡CCH$_2$OH.

In yet other embodiments, Hal is —Cl, y is 1 or 2, and $R_2$ is —Cl, —F, —Br, —OCH$_3$, —CH$_3$, —C(O)N(H)CH$_3$, —CF$_3$, —CN or —C≡CCH$_2$OH.

In particular embodiments, $R_3$ is —H. In certain embodiments, $R_3$ is —CH$_3$. In further embodiments, $R_3$ is —CH$_2$CH$_3$. In still further embodiments, $R_3$ is —CHCH$_2$. In other embodiments, $R_3$ is —CH$_2$CH$_2$OH. In particular embodiments, $R_3$ is —(CH$_2$)$_2$C$_6$H$_5$. In other embodiments, $R_3$ is —CH$_2$C(O)OH. In yet other embodiments, $R_3$ is —CH$_2$C(O)N(H)CH$_3$. In certain embodiments, $R_3$ is —CH$_2$C(O)N(H)((CH$_2$)$_2$N(CH$_3$)$_2$).

In yet other embodiments, $R_3$ is —CH$_2$C(O)N(H)((CH$_2$)$_3$N(CH$_3$)$_2$). In other embodiments, $R_3$ is —CH$_2$C(O)N(CH$_3$)CH$_2$CN. In particular embodiments, $R_3$ is —CH$_2$C(O)NH$_2$. In certain embodiments, $R_3$ is —CH$_2$C(O)N(H)((CH$_2$)$_2$OH). In other embodiments, $R_3$ is —CH$_2$C(O)N(H)((CH$_2$)$_2$OCH$_3$). In still further embodiments, $R_3$ is —CH$_2$C(CH$_3$)$_2$OH. In yet other embodiments, $R_3$ is —CH$_2$C(O)OCH$_3$. In further embodiments, $R_3$ is —CH$_2$CH(OH)CH$_3$. In still further embodiments, $R_3$ is —CH$_2$CH$_2$OH. In particular embodiments, $R_3$ is —CH(CH$_3$)CH$_2$OH.

In further embodiments, $R_3$ is —CH$_2$C(O)$R_4$ and $R_4$ is

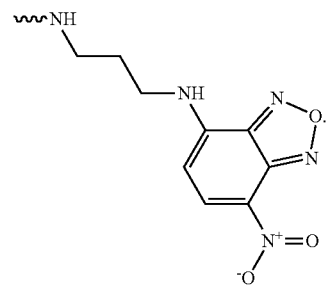

In other embodiments, $R_3$ is —CH$_2$C(O)$R_4$ and $R_4$ is

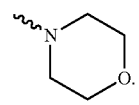

In particular embodiments, $R_3$ is —CH$_2$C(O)$R_4$ and $R_4$ is

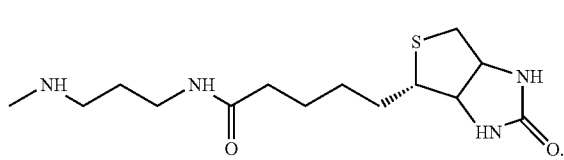 [SMILES: CNCCCNC(=O)CCCC[C@@H]1SCC2NC(=O)NC21]

In yet other embodiments, R$_3$ is —CH$_2$C(O)R$_4$ and R$_4$ is

In certain embodiments, R$_3$ is —CH$_2$C(O)R$_4$ and R$_4$ is

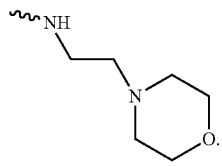

In other embodiments, R$_3$ is —CH$_2$C(O)R$_4$ and R$_4$ is

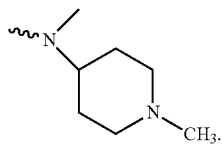

In particular embodiments, R$_3$ is —CH$_2$C(O)R$_4$ and R$_4$ is

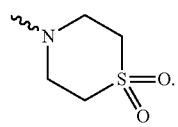

In yet other embodiments, R$_3$ is —CH$_2$C(O)R$_4$ and R$_4$ is

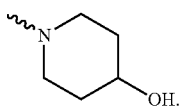

In certain embodiments, R$_3$ is —CH$_2$C(O)R$_4$ and R$_4$ is

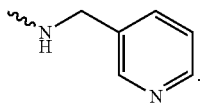

In other embodiments, R$_3$ is —CH$_2$C(O)R$_4$ and R$_4$ is

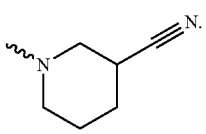

In particular embodiments, R$_3$ is —CH$_2$C(O)R$_4$ and R$_4$ is

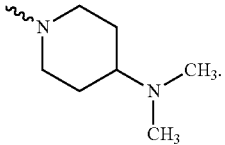

In yet other embodiments, R$_3$ is —CH$_2$C(O)R$_4$ and R$_4$ is

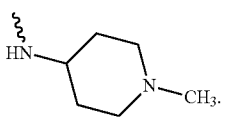

In certain embodiments, R$_3$ is —CH$_2$C(O)R$_4$ and R$_4$ is

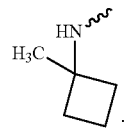

In other embodiments, R$_3$ is —CH$_2$C(O)R$_4$ and R$_4$ is

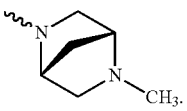

In particular embodiments, R$_3$ is —CH$_2$C(O)R$_4$ and R$_4$ is

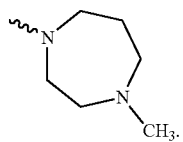

In yet other embodiments, R$_3$ is —CH$_2$C(O)R$_4$ and R$_4$ is

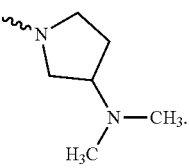

In certain embodiments, R$_3$ is —CH$_2$C(O)R$_4$ and R$_4$ is

In other embodiments, $R_3$ is —CH$_2$C(O)R$_4$ and R$_4$ is

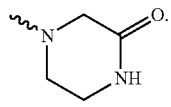

In particular embodiments, $R_3$ is —CH$_2$C(O)R$_4$ and R$_4$ is

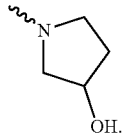

In yet other embodiments, $R_3$ is —CH$_2$C(O)R$_4$ and R$_4$ is

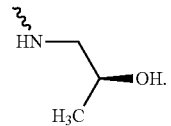

In certain embodiments, $R_3$ is —CH$_2$C(O)R$_4$ and R$_4$ is

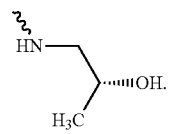

In other embodiments, $R_3$ is —CH$_2$C(O)R$_4$ and R$_4$ is

In particular embodiments, $R_3$ is —CH$_2$C(O)R$_4$ and R$_4$ is

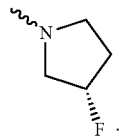

In yet other embodiments, $R_3$ is —CH$_2$C(O)R$_4$ and R$_4$ is

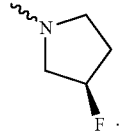

In certain embodiments, $R_3$ is —CH$_2$C(O)R$_4$ and R$_4$ is

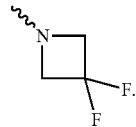

In other embodiments, $R_3$ is —CH$_2$C(O)R$_4$ and R$_4$ is

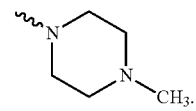

In further embodiments of the invention, $R_3$ is —CH$_2$C(O)R$_4$ and R$_4$ is

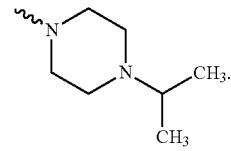

In certain embodiments of the invention, $R_3$ is —CH$_2$C(O)R$_4$ and R$_4$ is

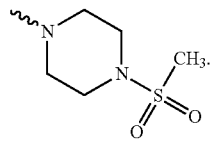

In other embodiments, $R_3$ is —CH$_2$C(O)R$_4$ and R$_4$ is

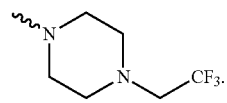

In further embodiments, $R_3$ is —CH$_2$C(O)R$_4$ and R$_4$ is

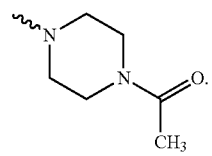

In further embodiments, $R_3$ is —CH$_2$C(O)R$_4$ and R$_4$ is

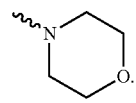

In particular embodiments, R$_3$ is —(CH$_2$)$_2$R$_5$ and R$_5$ is

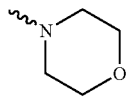

In yet other embodiments, R$_3$ is —(CH$_2$)$_2$R$_5$ and R$_5$ is

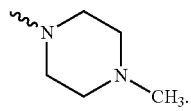

In certain embodiments, R$_3$ is —(CH$_2$)$_2$R$_5$ and R$_5$ is

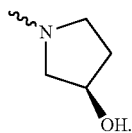

In other embodiments, invention, R$_3$ is —(CH$_2$)$_2$R$_5$ and R$_5$ is

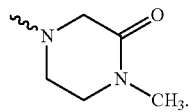

In some embodiments, a is an integer ranging from 0 to 5. In some embodiments, b is an integer ranging from 0 to 4. In some embodiments, c is an integer ranging from 0 to 6.

Compounds of Formula III

The invention additionally provides compounds of Formula III:

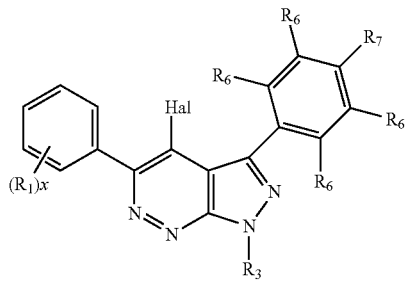

Formula III and pharmaceutically acceptable salts thereof,
wherein Hal is —Cl, —F, —I, or —Br;
x is an integer ranging from 0 to 5;
each R$_1$ is independently —Cl, —F, —I, —Br, —C$_1$-C$_3$ alkyl, —O—C$_1$-C$_3$ alkyl, —CN, —CF$_3$, —C(O)NH(CH$_3$), or —C≡CCH$_2$OH;
R$_3$ is —H, —C$_1$-C$_6$ alkyl, —(C$_1$-C$_6$ alkylene)-OH, —(C$_1$-C$_6$ alkylene)-phenyl, —(C$_1$-C$_6$ alkylene)-O—(C$_1$-C$_6$ alkyl), —C$_2$-C$_6$ alkenyl, —(C$_1$-C$_6$ alkylene)-C(O)R$_4$, —(C$_1$-C$_6$ alkylene)-R$_5$

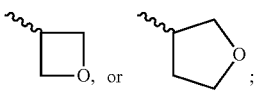

R$_4$ is —OH, —O—(C$_1$-C$_6$ alkyl), —NH$_2$, —NH(C$_1$-C$_6$ alkyl), —NH((C$_1$-C$_6$ alkylene)-OH), —NH((C$_1$-C$_6$ alkylene)N(C$_1$-C$_6$ alkyl)$_2$), —N(C$_1$-C$_6$ alkyl)((C$_1$-C$_6$ alkylene)-CN), —N(C$_1$-C$_6$ alkyl)((C$_1$-C$_6$ alkylene)N(C$_1$-C$_6$ alkyl)$_2$), —NH(C$_1$-C$_6$ alkylene)-O—(C$_1$-C$_6$ alkyl),

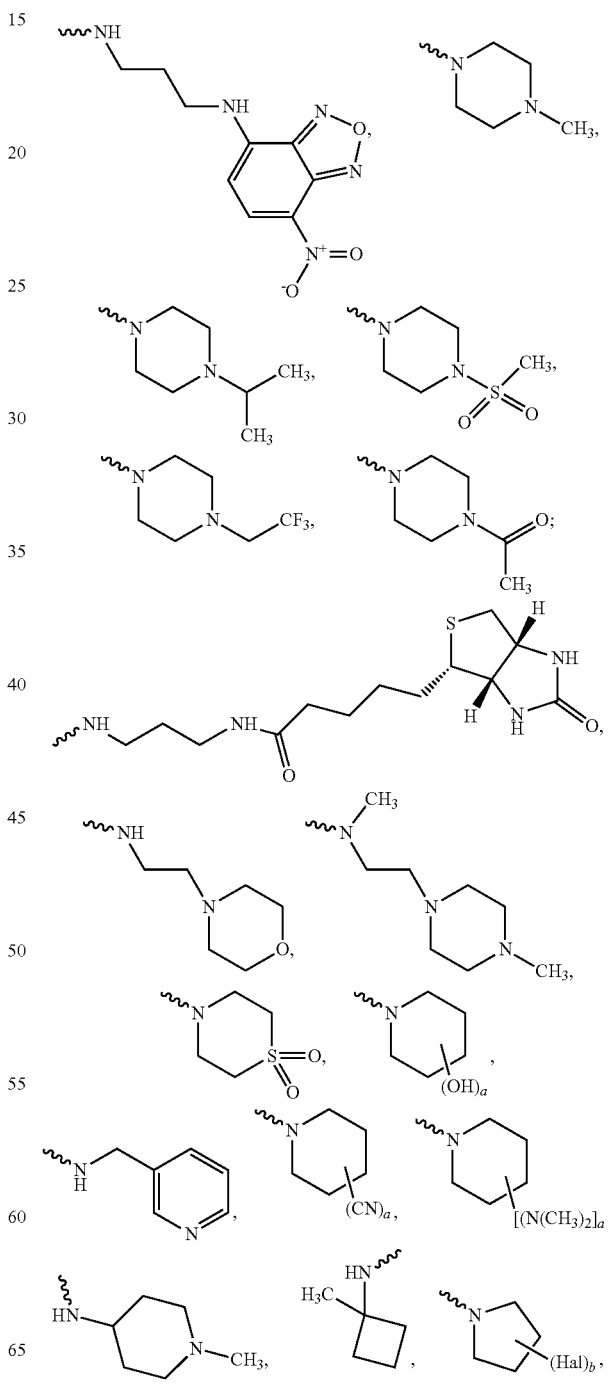

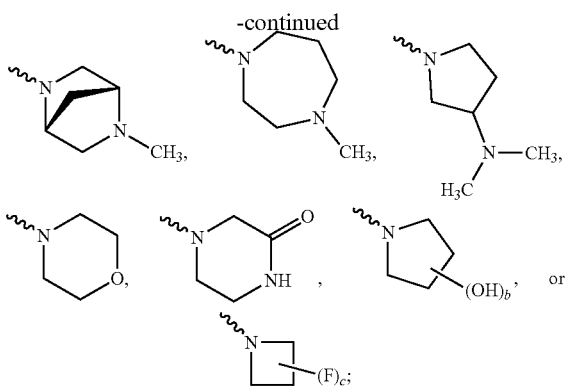

a is an integer ranging from 0 to 10;
b is an integer ranging from 0 to 8;
c is an integer ranging from 0 to 6;
$R_5$ is

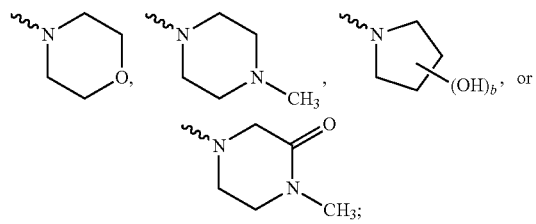

wherein each $R_6$ and $R_7$ is independently —H or —I, wherein at least one of $R_6$ and $R_7$ is —I,
and wherein when $R_3$ is —$C_1$-$C_3$ alkyl, $R_7$ is —H.

In certain embodiments, one $R_6$ in the ortho position relative to the pyrazolopyridazino ring system is iodo and the remaining $R_6$ and $R_7$ groups are hydrogen. In other embodiments, one $R_6$ in the para position relative to the pyrazolopyridazino ring system is iodo and the remaining $R_6$ and $R_7$ groups are hydrogen. In further embodiments, one $R_6$ in the ortho position relative to the pyrazolopyridazino ring system and one $R_6$ in the para position relative to the pyrazolopyridazino ring system are iodo and the remaining $R_6$ and $R_7$ groups are hydrogen. In further embodiments, the two $R_6$ groups in the ortho positions relative to the pyrazolopyridazino ring system and one $R_6$ in the para position relative to the pyrazolopyridazino ring system are iodo and the remaining $R_6$ and $R_7$ groups are hydrogen. In further embodiments, the two $R_6$ groups in the para positions relative to the pyrazolopyridazino ring system and one $R_6$ in the ortho position relative to the pyrazolopyridazino ring system are iodo and the remaining $R_6$ and $R_7$ are hydrogen. In certain embodiments, all $R_6$ groups are iodo and $R_7$ is hydrogen. In yet further embodiments, $R_7$ is is iodo and the $R_6$ groups are hydrogen.

In a particular embodiment, one $R_6$ in the para position relative to the pyrazolopyridazino ring system is iodo and $R_3$ is —$CH_3$.

In certain embodiments, Hal is —Cl. In yet another embodiment, x is 0. In another embodiment, x is1. In a certain embodiments, x is2.

In particular embodiments, x is 1 and $R_1$ is in the ortho position relative to the pyrazolopyridazino ring system. In certain embodiments, x is 1 and $R_1$ is in the para position relative pyrazolopyridazino ring system. In further embodiments, x is 1 and $R_1$ is in the meta position relative pyrazolopyridazino ring system.

In particular embodiments, x is 2 and $R_1$ is in the ortho and meta position relative pyrazolopyridazino ring system. In certain embodiments, x is 2 and $R_1$ is in the ortho and para position relative pyrazolopyridazino ring system. In further embodiments, x is 2 and $R_1$ is in the para and meta position relative pyrazolopyridazino ring system.

In yet other embodiments, $R_1$ is —Cl. In certain embodiments, $R_1$ is —F. In certain embodiments, $R_1$ is —I. In further embodiments, $R_1$ is —$OCH_3$. In other embodiments, $R_1$ is —$CH_3$. In yet other embodiments, $R_1$ is —C(O)N(H)$CH_3$. In certain embodiments, $R_1$ is —$CF_3$. In further embodiments, $R_1$ is —CN. In additional embodiments, $R_1$ is —C≡$CCH_2OH$.

In yet other embodiments, x is 1 or 2, and $R_1$ is —Cl, —F, —Br, —I, —$OCH_3$, —$CH_3$, —C(O)N(H)$CH_3$, —$CF_3$, —CN or —C≡$CCH_2OH$.

In yet other embodiments, Hal is —Cl, x is 1 or 2, and $R_1$ is —Cl, —F, —Br, —I, —$OCH_3$, —$CH_3$, —C(O)N(H)$CH_3$, —$CF_3$, —CN or —C≡$CCH_2OH$.

In particular embodiments, $R_3$ is —H. In certain embodiments, $R_3$ is —$CH_3$. In further embodiments, $R_3$ is —$CH_2CH_3$. In still further embodiments, $R_3$ is —$CHCH_2$. In other embodiments, $R_3$ is —$CH_2CH_2OH$. In particular embodiments, $R_3$ is —$(CH_2)_2C_6H_5$. In other embodiments, $R_3$ is —$CH_2C(O)OH$. In yet other embodiments, $R_3$ is —$CH_2C(O)N(H)CH_3$. In certain embodiments, $R_3$ is —$CH_2C(O)N(H)((CH_2)_2N(CH_3)_2)$. In yet other embodiments, $R_3$ is —$CH_2C(O)N(H)((CH_2)_3N(CH_3)_2)$. In other embodiments, $R_3$ is —$CH_2C(O)N(CH_3)CH_2CN$. In particular embodiments, $R_3$ is —$CH_2C(O)NH_2$. In certain embodiments, $R_3$ is —$CH_2C(O)N(H)((CH_2)_2OH)$. In other embodiments, $R_3$ is —$CH_2C(O)N(H)((CH_2)_2OCH_3)$. In still further embodiments, $R_3$ is —$CH_2C(CH_3)_2OH$. In yet other embodiments, $R_3$ is —$CH_2C(O)OCH_3$. In further embodiments, $R_3$ is —$CH_2CH(OH)CH_3$. In still further embodiments, $R_3$ is —$CH_2CH_2OH$. In particular embodiments, $R_3$ is —$CH(CH_3)CH_2OH$.

In further embodiments, $R_3$ is —$CH_2C(O)R_4$ and $R_4$ is

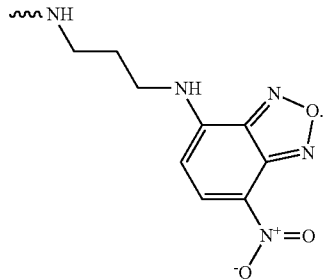

In other embodiments, $R_3$ is —$CH_2C(O)R_4$ and $R_4$ is

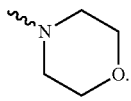

In particular embodiments, R₃ is —CH₂C(O)R₄ and R₄ is

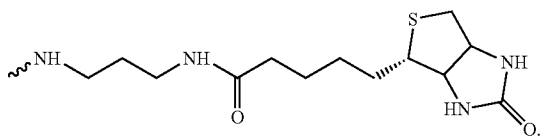

In yet other embodiments, R₃ is —CH₂C(O)R₄ and R₄ is

In certain embodiments, R₃ is —CH₂C(O)R₄ and R₄ is

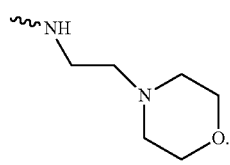

In other embodiments, R₃ is —CH₂C(O)R₄ and R₄ is

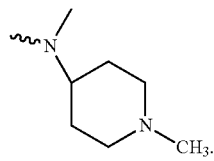

In particular embodiments, R₃ is —CH₂C(O)R₄ and R₄ is

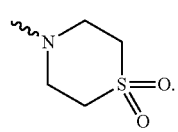

In yet other embodiments, R₃ is —CH₂C(O)R₄ and R₄ is

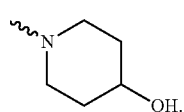

In certain embodiments, R₃ is —CH₂C(O)R₄ and R₄ is

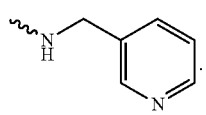

In other embodiments, R₃ is —CH₂C(O)R₄ and R₄ is

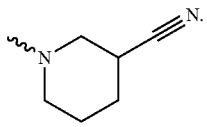

In particular embodiments, R₃ is —CH₂C(O)R₄ and R₄ is

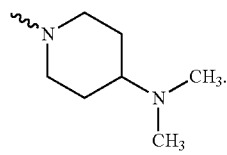

In yet other embodiments, R₃ is —CH₂C(O)R₄ and R₄ is

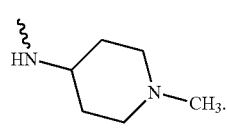

In certain embodiments, R₃ is —CH₂C(O)R₄ and R₄ is

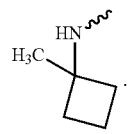

In other embodiments, R₃ is —CH₂C(O)R₄ and R₄ is

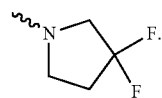

In particular embodiments, R₃ is —CH₂C(O)R₄ and R₄ is

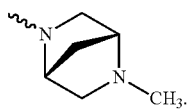

In yet other embodiments, R₃ is —CH₂C(O)R₄ and R₄ is

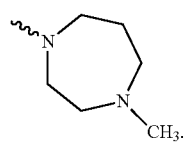

In certain embodiments, R₃ is —CH₂C(O)R₄ and R₄ is

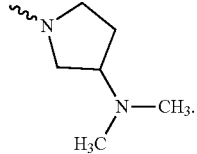

In other embodiments, R₃ is —CH₂C(O)R₄ and R₄ is

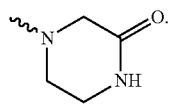

In particular embodiments, R₃ is —CH₂C(O)R₄ and R₄ is

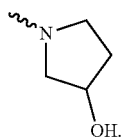

In yet other embodiments, R₃ is —CH₂C(O)R₄ and R₄ is

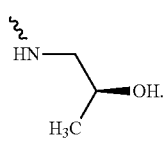

In certain embodiments, R₃ is —CH₂C(O)R₄ and R₄ is

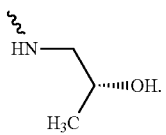

In other embodiments, R₃ is —CH₂C(O)R₄ and R₄ is

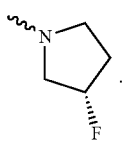

In particular embodiments, R₃ is —CH₂C(O)R₄ and R₄ is

In yet other embodiments, R₃ is —CH₂C(O)R₄ and R₄ is

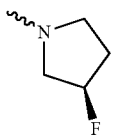

In certain embodiments, R₃ is —CH₂C(O)R₄ and R₄ is

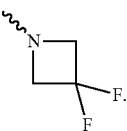

In other embodiments, R₃ is —CH₂C(O)R₄ and R₄ is

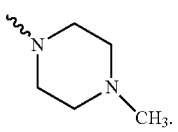

In further embodiments of the invention, R₃ is —CH₂C(O)R₄ and R₄ is

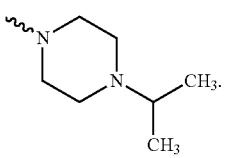

In certain embodiments of the invention, R₃ is —CH₂C(O)R₄ and R₄ is

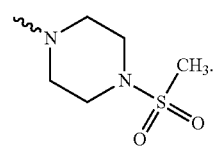

In other embodiments, R₃ is —CH₂C(O)R₄ and R₄ is

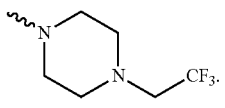

In further embodiments, R₃ is —CH₂C(O)R₄ and R₄ is

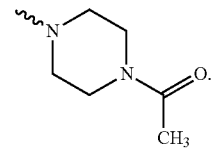

In further embodiments, $R_3$ is —$CH_2C(O)R_4$ and $R_4$ is

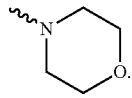

In particular embodiments, $R_3$ is —$(CH_2)_2R_5$ and $R_5$ is

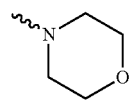

In yet other embodiments, $R_3$ is —$(CH_2)_2R_5$ and $R_5$ is

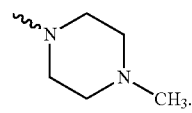

In certain embodiments, $R_3$ is —$(CH_2)_2R_5$ and $R_5$ is

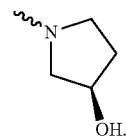

In other embodiments, invention, $R_3$ is —$(CH_2)_2R_5$ and $R_5$ is

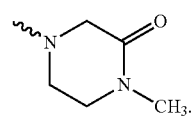

In some embodiments, a is an integer ranging from 0 to 5. In some embodiments, b is an integer ranging from 0 to 4. In some embodiments, c is an integer ranging from 0 to 6.

Illustrative Pyrazolopyridazine Compounds

Non-limiting examples of specific Pyrazolopyridazine compounds include:

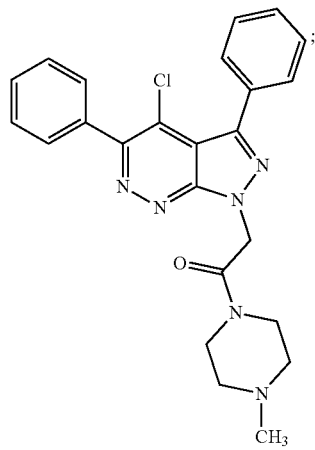

1

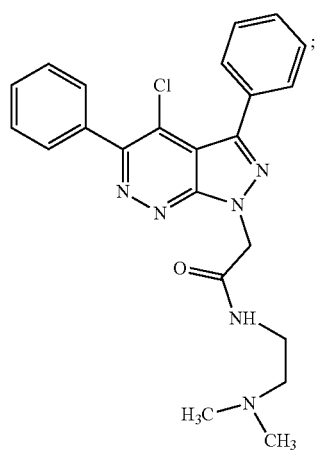

2

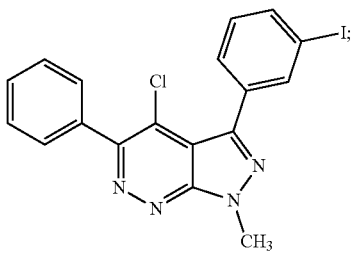

3

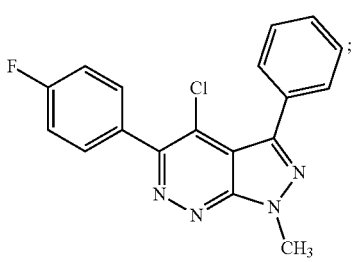

4

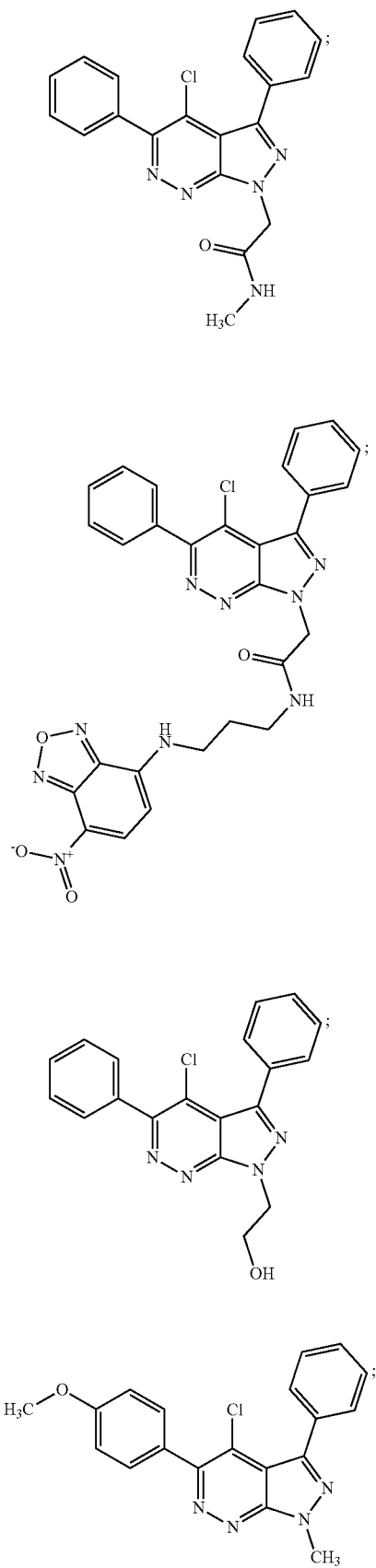
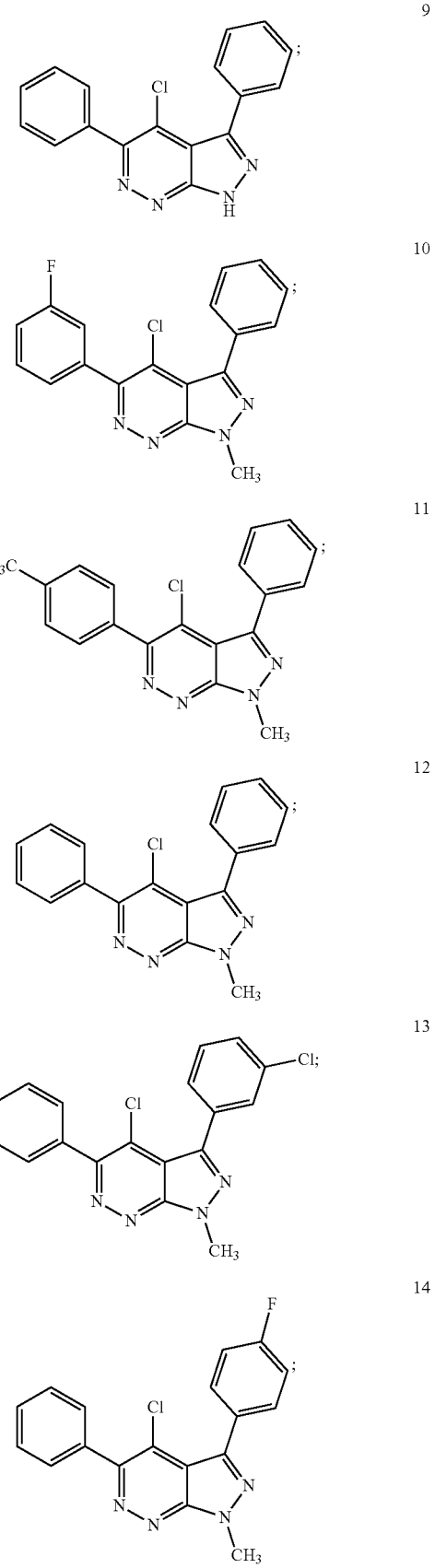

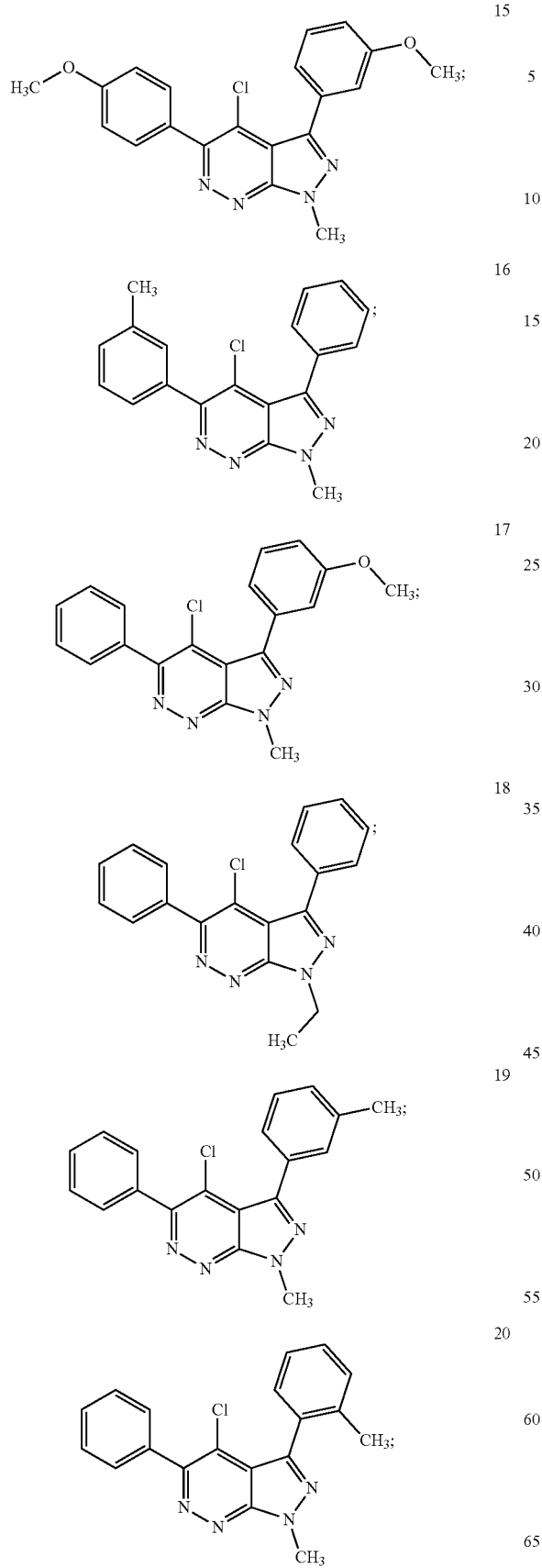
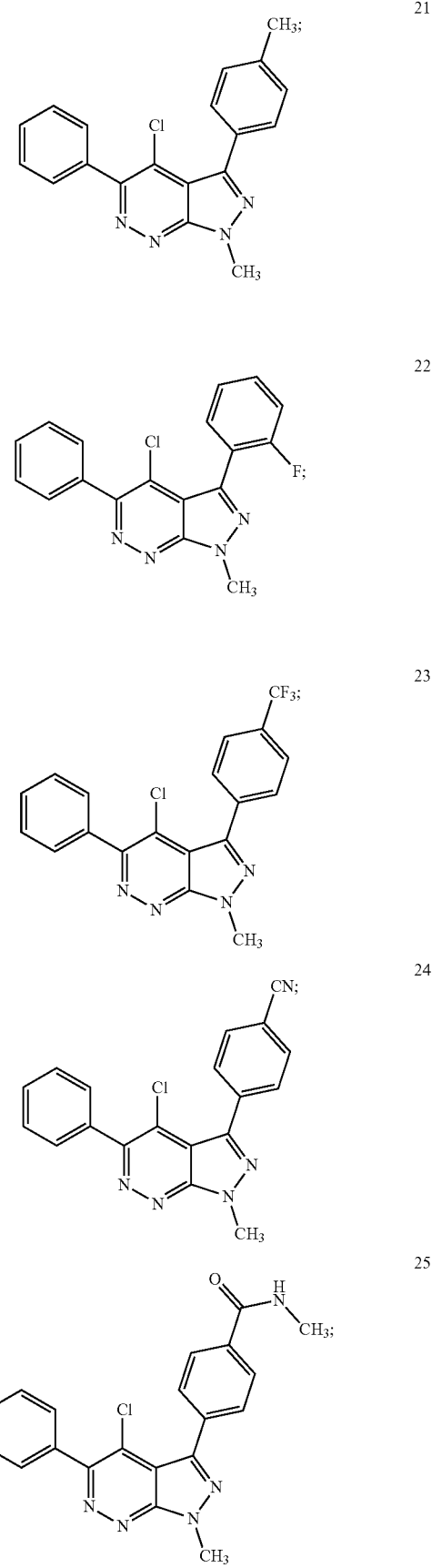

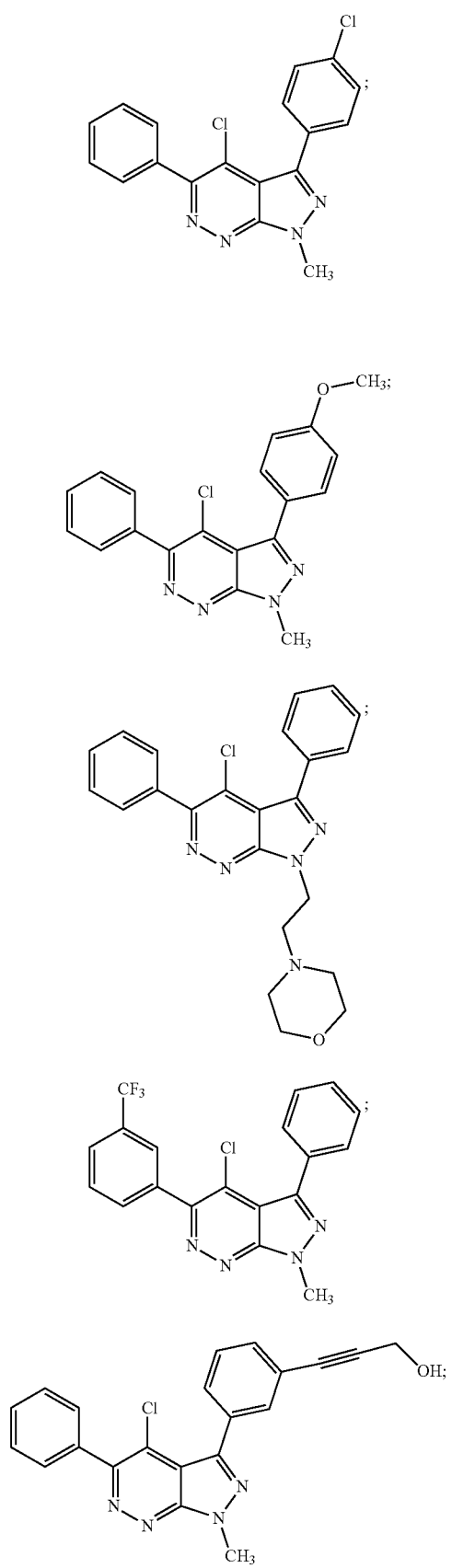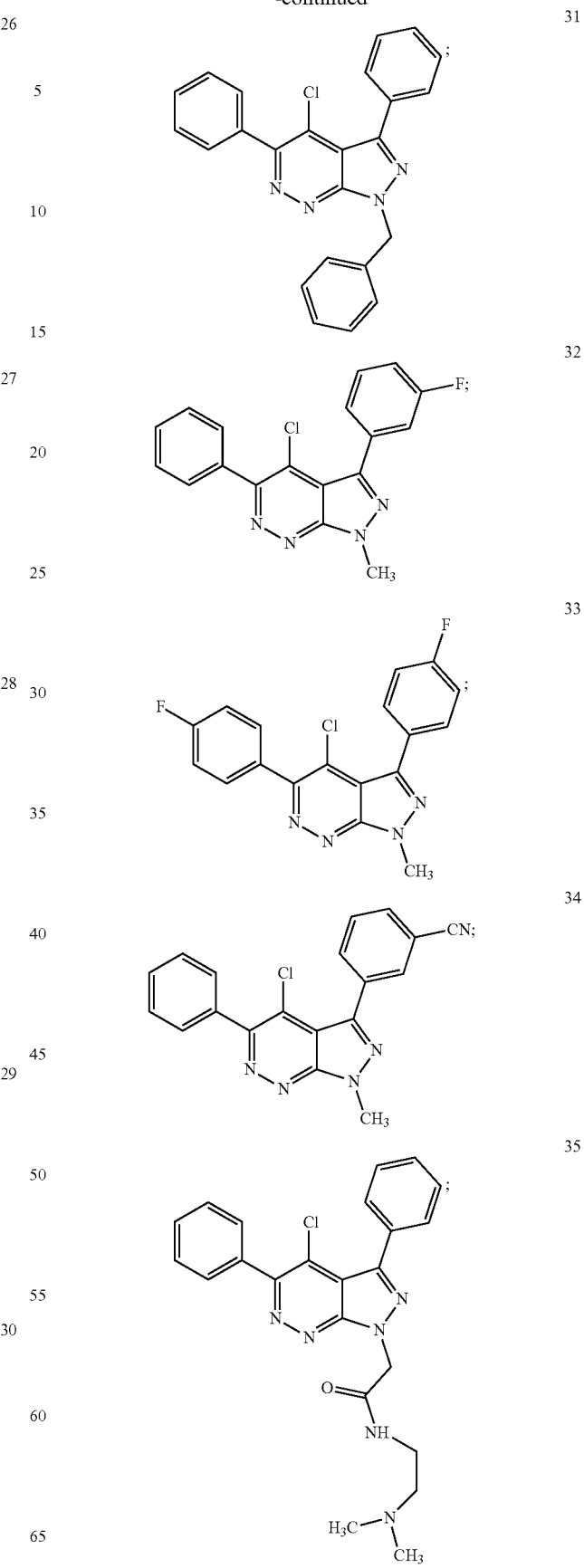

37
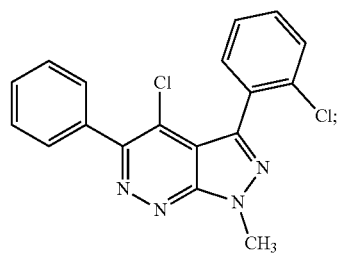
38
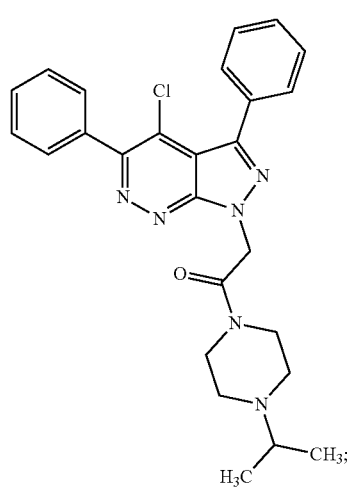
39
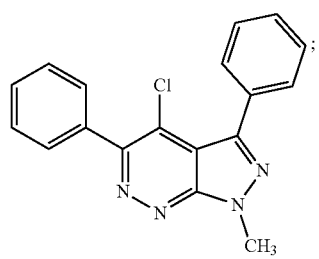
42
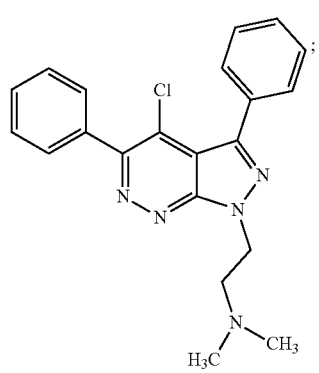
45
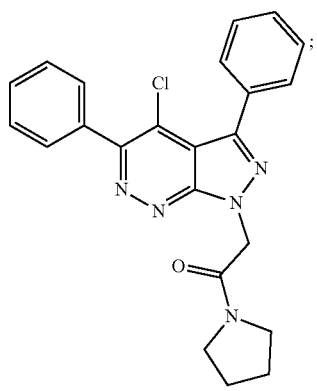
47
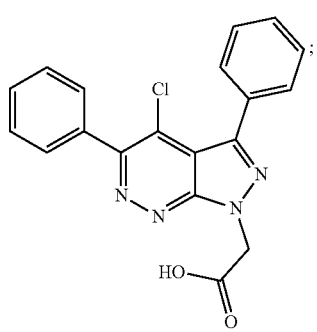
48
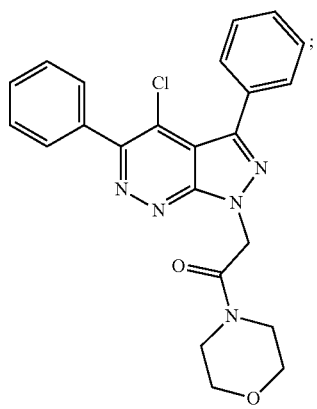
49
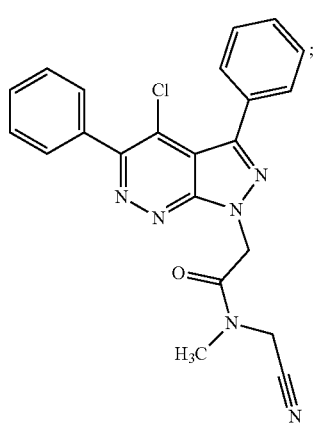

50
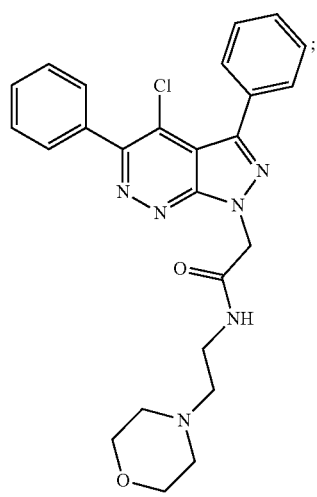
51
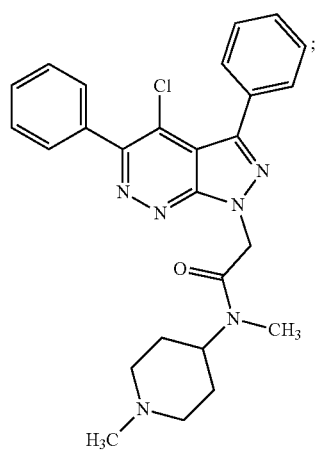
52
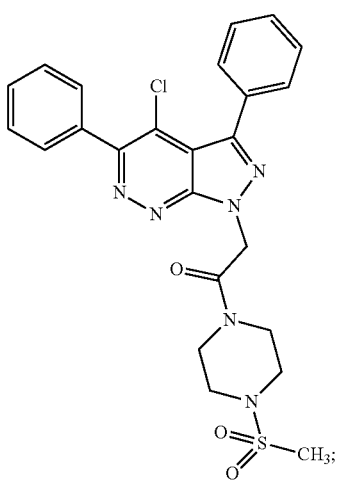
53
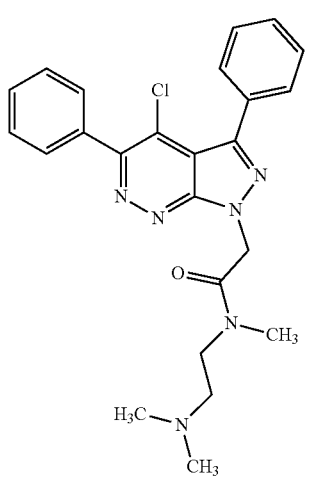
54
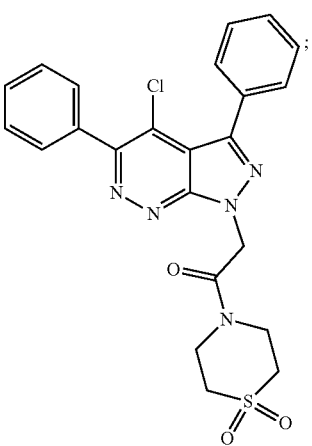
55
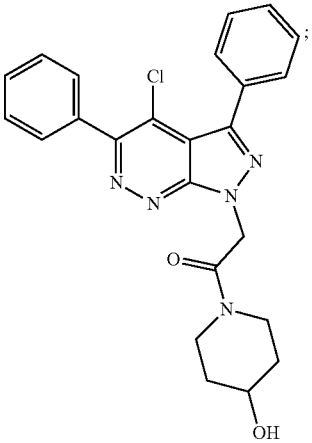

56
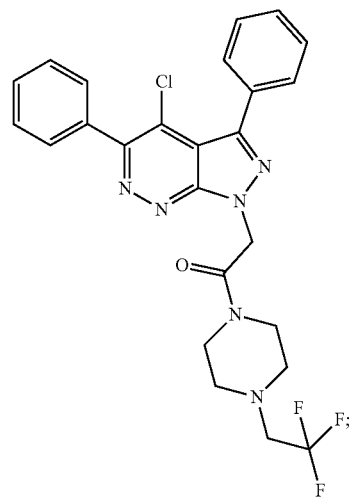
57
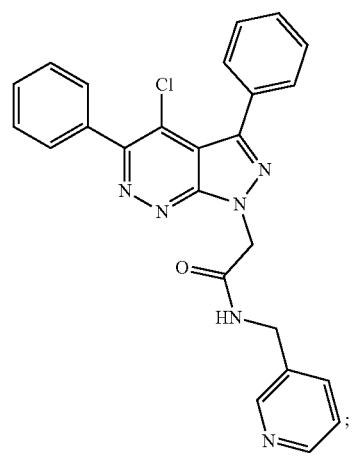
58
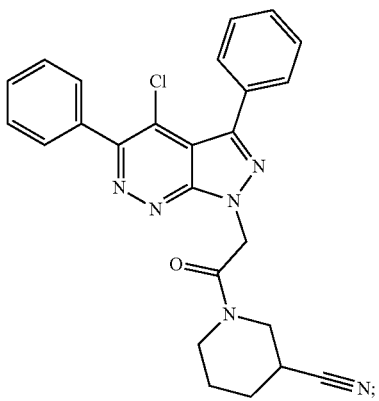
59
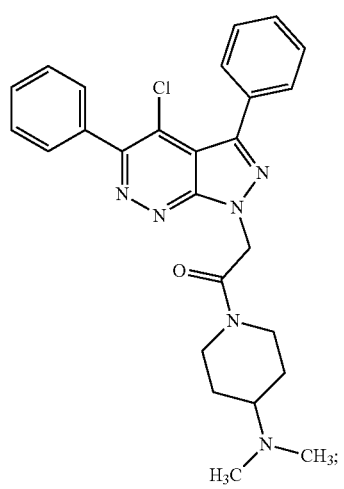
60
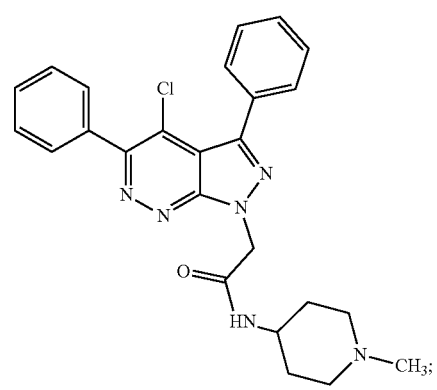
61
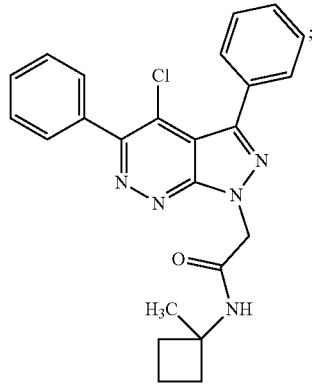
62
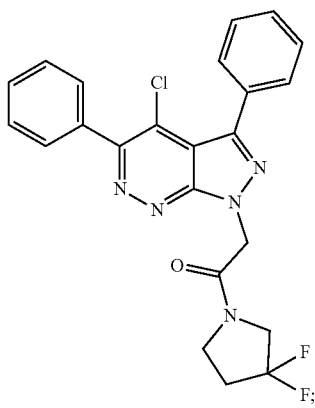

63
-continued
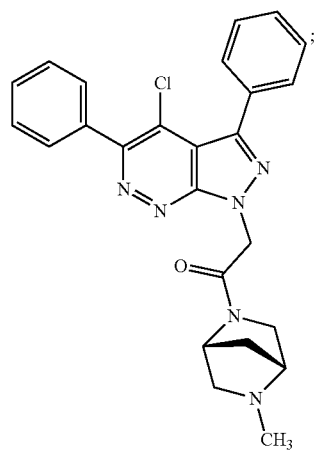
63
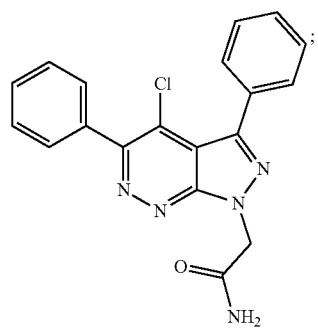
64
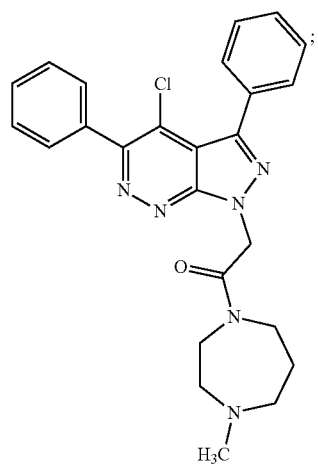
65
64
-continued
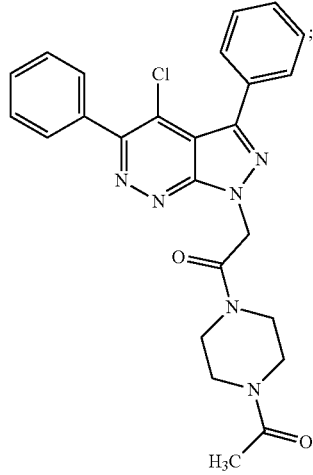
66
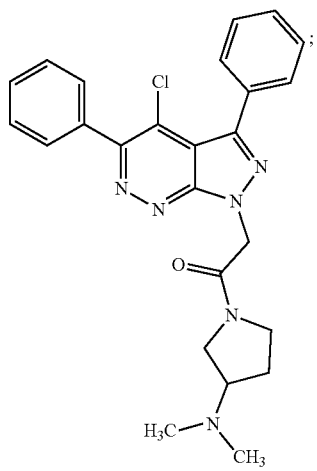
67
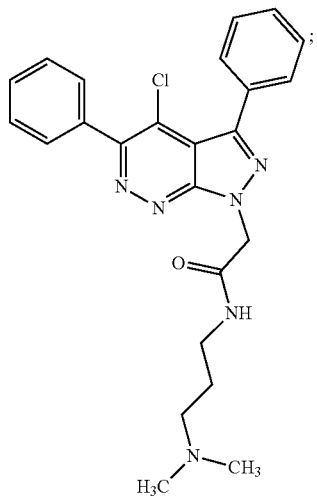
68

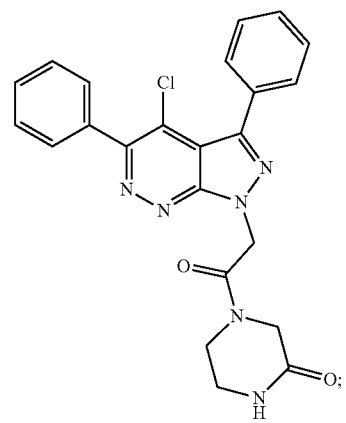
69
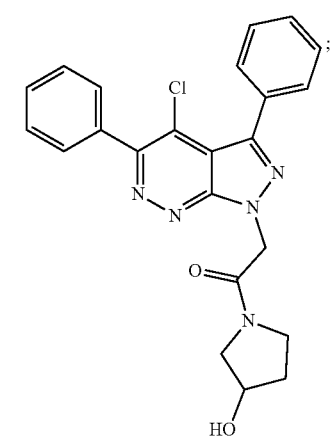
70
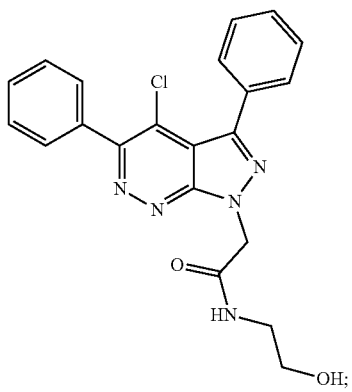
71
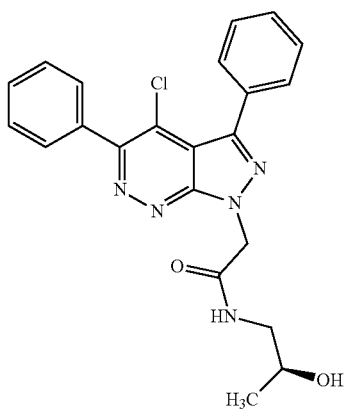
72
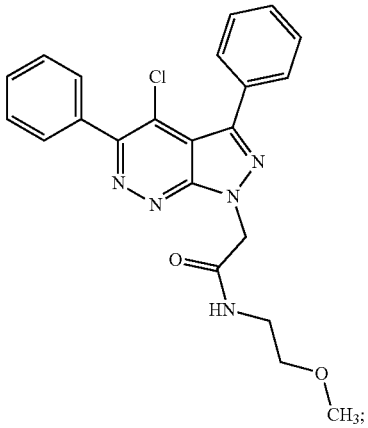
73
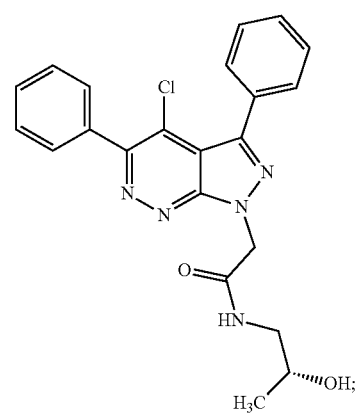
74
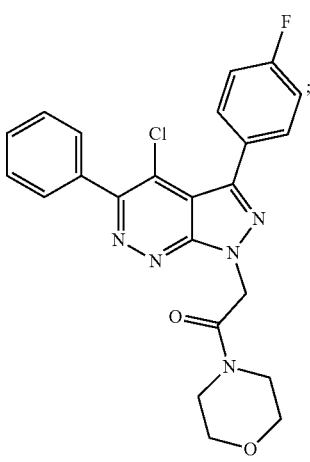
75

76 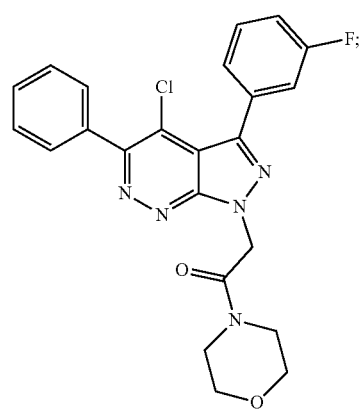
77 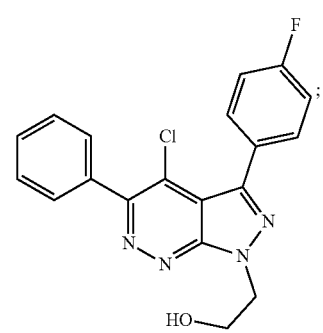
78 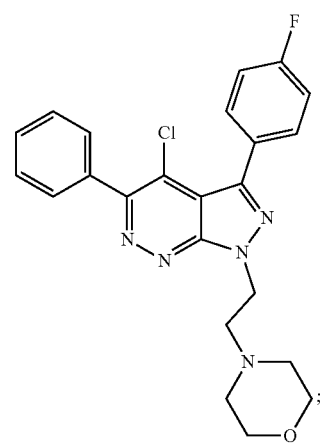
79 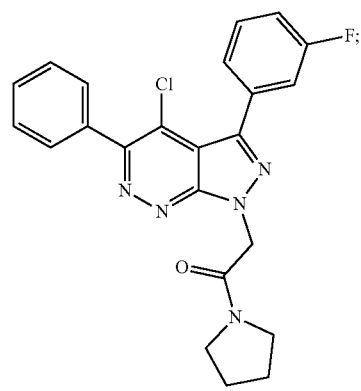
80 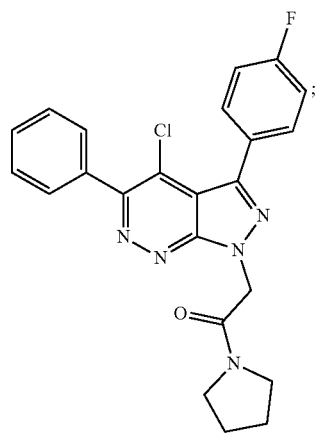
81 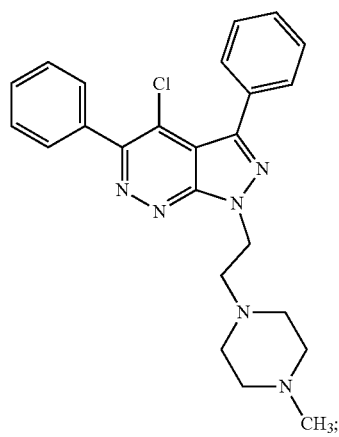
82 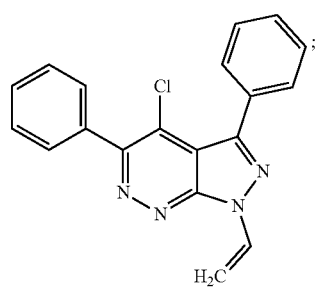
83 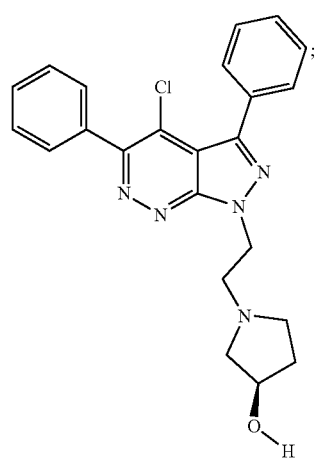

84
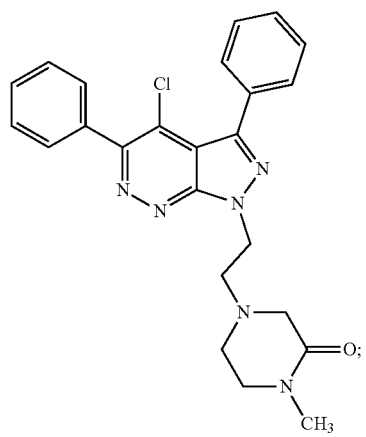
85
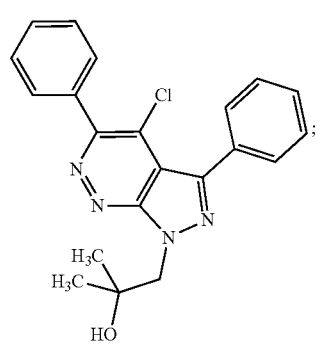
86
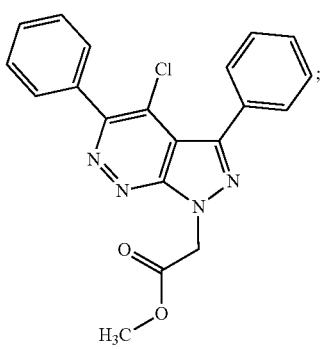
87
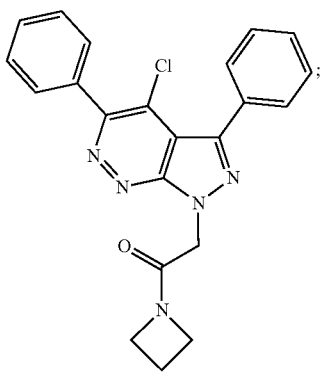
88
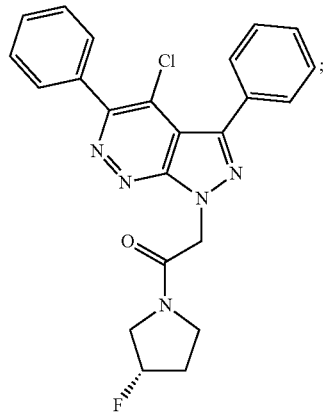
89
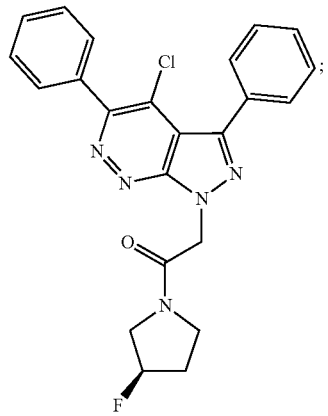
90
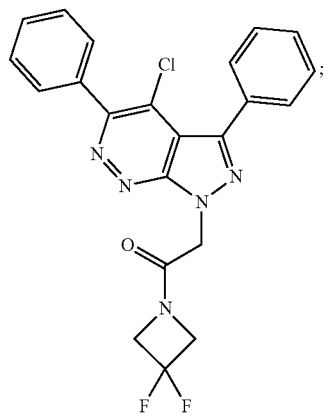
91
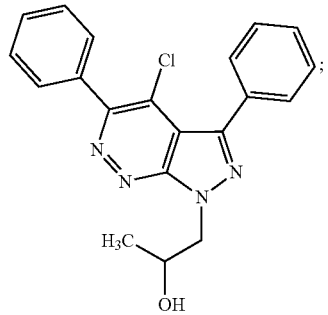

92
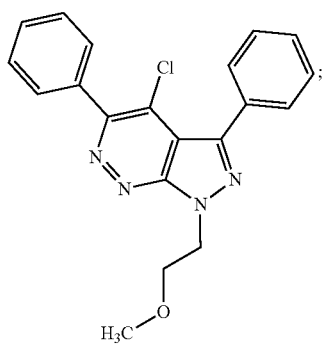

93
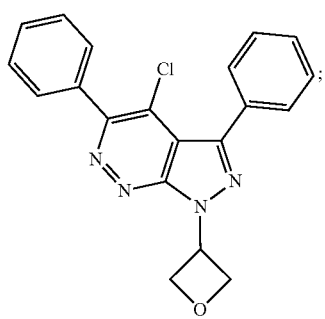

94
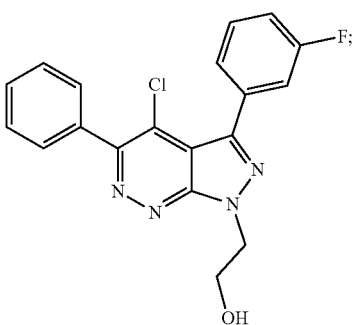

95
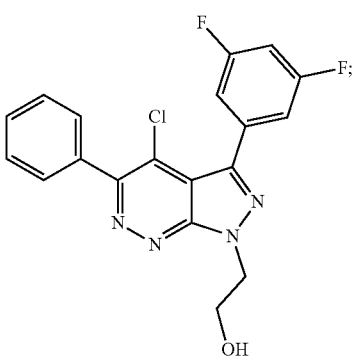

96
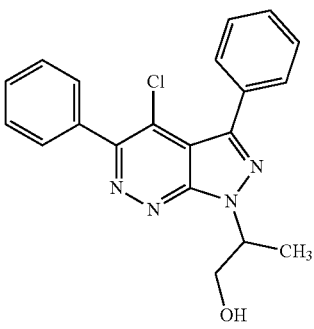

and

97
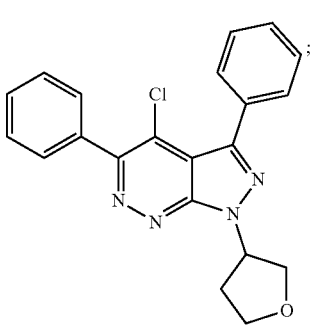

and pharmaceutically acceptable salts thereof.

Compounds of Formula IV

The invention additionally provides compounds of Formula IV:

Formula IV

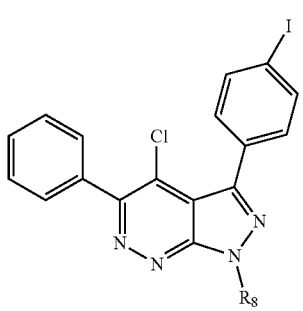

and salts thereof, wherein $R_8$ is —$C_1$-$C_3$ alkyl.

In certain embodiments of the invention, $R_8$ is —$CH_3$, in yet further embodiments of the invention, $R_8$ is —$CH_2CH_3$. In other embodiments of the invention, $R_8$ is —$CH_2CH_2CH_3$. In other embodiments of the invention, $R_8$ is —$CH(CH_3)_2$.

The invention still further provides Compound 43, which has the structure:

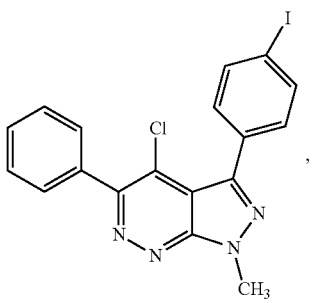 [SMILES: Cn1nc(-c2ccc(I)cc2)c2c(Cl)c(-c3ccccc3)nnc21]

and salts thereof. Such salts are the reaction product of Compound 43 and an inorganic or organic acid. In one embodiment a salt is a pharmaceutically acceptable salt.

Compounds of Formula IV, compound 43 and salts thereof are useful as intermediates for synthesizing for Pyrazolopyridazine compounds.

The invention still further provides Compound 44, which has the structure:

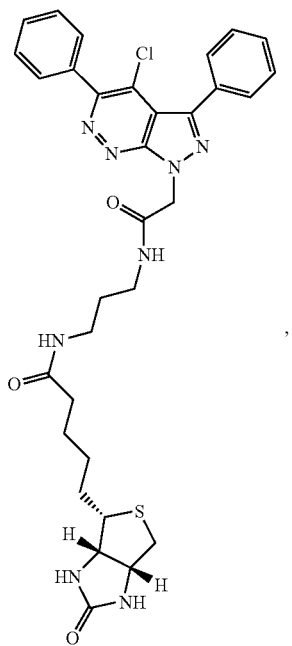 [SMILES: O=C(CCCC[C@@H]1SC[C@@H]2NC(=O)N[C@@H]21)NCCCNC(=O)Cn1nc(-c2ccccc2)c2c(Cl)c(-c3ccccc3)nnc21]

and salts thereof. Such salts are the reaction product of Compound 44 and an inorganic or organic acid. In one embodiment a salt is a pharmaceutically acceptable salt.

Compound 44 is useful as a probe for identifying proteins that bind to its bisphenyl pyrazolopyridazine moiety.

The invention still further provides Compound 46, which has the structure:

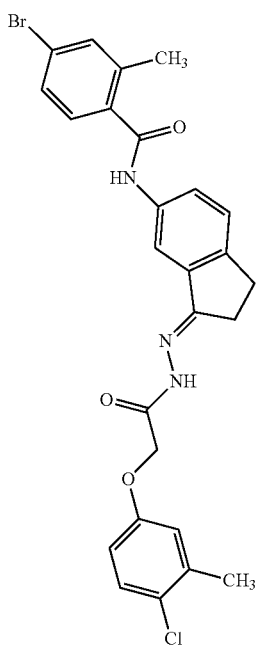 [SMILES: Cc1cc(OCC(=O)N/N=C2\CCc3ccc(NC(=O)c4ccc(Br)cc4C)cc32)ccc1Cl]

and pharmaceutically acceptable salts thereof.

Some of the compounds disclosed herein, for example, Compounds 44, 63, 72, 74, 83, 88 and 89, are depicted having a bold or hatched wedge, indicating absolute stereochemistry.

Without being bound by any particular mechanism, it is believed that the bisphenyl pyrazolopyridazine moiety of Pyrazolopyridazine compounds is involved in the restoration of the activity and trafficking of Clarin I, which is the protein encoded by the gene mutated in Usher III Syndrome (Adato et al., Eur J Hum Genet. 2002 June; 10(6):339-50)

Proteins or domains thereof that can interact with Clarin I, and therefore can bind to the bisphenyl pyrazolopyridazine moiety of Compound 44, include, but are not limited to the proteins listed in Table 1 (Tian et al., J Biol Chem. 2009 Jul. 10; 284(28):18980-93):

TABLE 1

4F2 cell-surface antigen heavy chain
78-kDa glucose-regulated protein
ATP synthase subunit γ, mitochondrial
Basigin
N-cadherin
Calnexin
Carboxypeptidase D
Catenin a-1
Cation-independent mannose-6-phosphate receptor
CD166 antigen
CD276 antigen
Cell adhesion molecule 1
Clarin-1
Coxsackievirus and adenovirus receptor
Guanine nucleotide-binding protein G(i), a-2 subunit
Guanine nucleotide-binding protein G(I)/G(S)/G(T) subunit beta-1
Heat shock 70-kDa protein 1
Integrin α-5
Integrin α-6
Integrin α-V
Integrin β-1
Junctional adhesion molecule A
Junctional adhesion molecule C
Monocarboxylate transporter 1
Myelin protein zero-like protein 1
Myosin light polypeptide 6

TABLE 1-continued

Neuropilin-1
Neutral amino acid transporter B(0)
Plasma membrane calcium-transporting ATPase 1
Plasma membrane calcium-transporting ATPase 4
Prostaglandin F2 receptor negative regulator
Protein 4.1
Ras-related C3 botulinum toxin substrate 1
Ras-related protein Rab-14
Ras-related protein Rab-9A
Ras-related protein Ral-A
Ras-related protein Rap-1A
Secretory carrier-associated membrane protein 1
Secretory carrier-associated membrane protein 3
Sodium/potassium-transporting ATPase subunit a-1
Sodium/potassium-transporting ATPase subunit β-3
Solute carrier family 12 member 2
Syntaxin-12
Syntaxin-4
Syntaxin-6
Syntaxin-7
Transferrin receptor protein 1
Tumor-associated calcium signal transducer 1
Type-1 angiotensin II receptor-associated protein
Tyrosine-protein kinase-like 7
Vesicle-associated membrane protein 3
Voltage-dependent anion-selective channel protein 1
Voltage-dependent anion-selective channel protein 2
Zinc transporter ZIP14

The compounds of the invention can be in the form of a salt. In some embodiments, the salt is a pharmaceutically acceptable salt. Pharmaceutically acceptable salts include, for example, acid-addition salts and base-addition salts. The acid that forms an acid-addition salt can be an organic acid or an inorganic acid. A base that forms a base-addition salt can be an organic base or an inorganic base. In some embodiments, a pharmaceutically acceptable salt is a metal salt. In some embodiments, a pharmaceutically acceptable salt is an ammonium salt.

Acid-addition salts can arise from the addition of an acid to the free-base form of a compound of the invention. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid-addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound of the invention having a carboxyl group. The inorganic base consists of a metal cation paired with a basic couterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, a aluminum salt, a copper salt, a cadmium salt, and a zinc salt.

Ammonium salts can arise from the addition of ammonia or an organic amine to a compound of the invention having a carboxyl group. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethylammonium salt, a diisopropylammonium salt, an ethanolammonium salt, a diethanolammonium salt, a triethanolammonium salt, a morpholinium salt, an N-methylmorpholinium salt, a piperidinium salt, an N-methylpiperidinium salt, an N-ethylpiperidinium salt, a dibenzylammonium salt, a piperazinium salt, a pyridinium salt, a pyrrazolium salt, an imidazolium salt, a pyrazinium salt, an ethylenediammonium salt, an N,N'-dibenzylethylenediammonium salt, a procaine salt, a chloroprocaine salt, a choline salt, a dicyclohexylammonium salt, and a N-methylglucamine salt.

Methods for Making the Pyrazolopyridazine Compounds

Non-limiting examples of synthetic schema that are useful for synthesizing the Pyrazolopyridazine compounds include the following.

Scheme 1

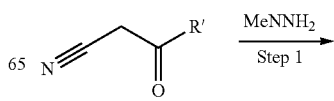

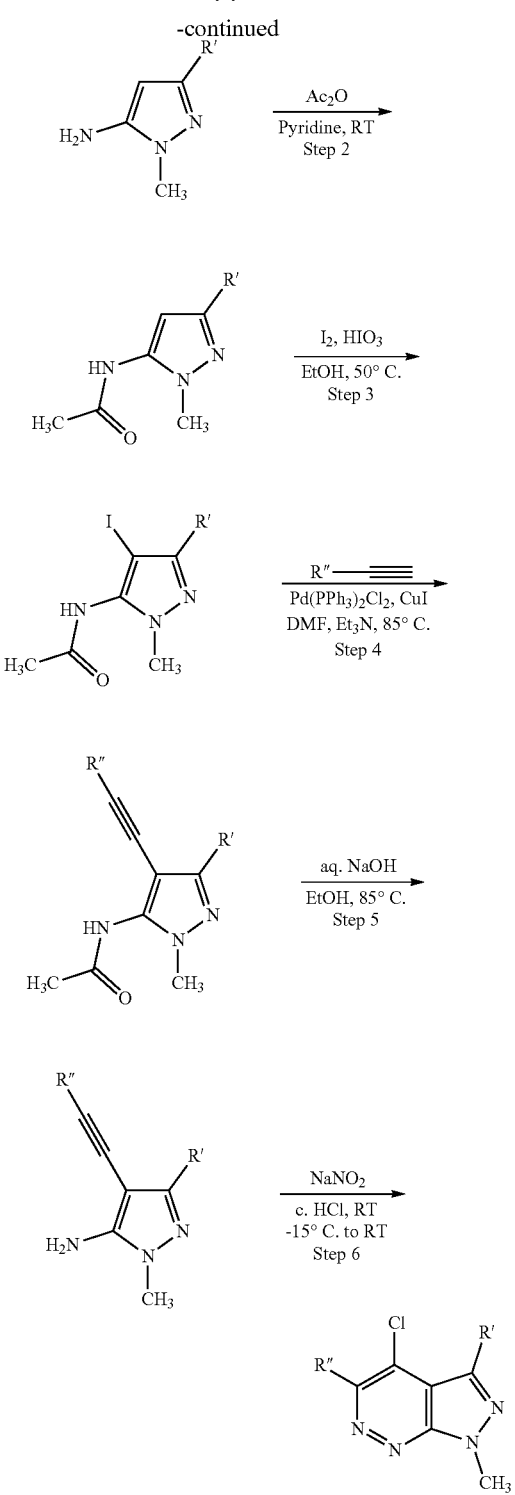

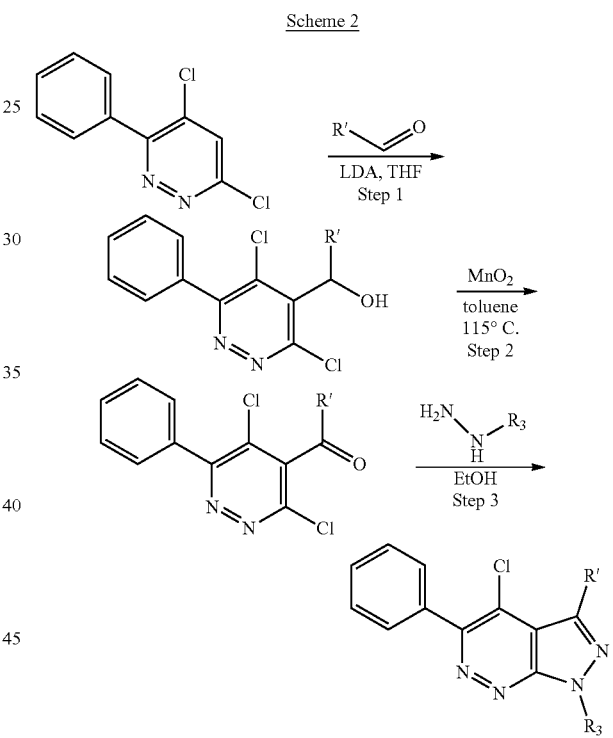

Scheme 1 generally describes the preparation of Pyrazolopyridazine compounds having a 1-N-methyl group and where R' and R" are independently an unsubstituted or a substituted phenyl group. For example, a 2-cyanocarbonyl compound in which R' is unsubstituted or substituted phenyl is condensed with N-methylhydrazine to provide a 3-substituted-1-methyl-1H-pyrazol-5-amine. The 5-amino group is acylated, for example, with acetic anhydride in the presence of a base, such as pyridine, to provide a 5-amido compound. The 5-amido compound is iodinated, for example, with a mixture of iodine and iodic acid in a solvent such as ethanol (EtOH) to provide an N-(3-substituted-4-iodo-1-methyl-1H-pyrazol-5-yl)acetamide. A palladium-mediated cross-coupling, such as a Sonagashira cross-coupling, of the acetamide with an R"-substituted terminal alkyne, catalyzed, for example, by a palladium complex such as palladium (II) bistriphenylphosphine dichloride in the presence of copper (I) iodide in a solvent such as dimethylformamide (DMF) with a base such as triethylamine provides a disubstituted alkyne in which R" is unsubstituted or substituted phenyl. Saponification of the alkyne acetamide with a base such as sodium hydroxide in a solvent such as ethanol provides the primary amine. Diazotization of the primary amine with sodium nitrite in concentrated hydrochloric acid provides a diazo intermediate, which cyclizes to provide a Pyrazolopyridazine compound having a 1-N-methyl group and where R' and R" are independently an unsubstituted or a substituted phenyl group.

Scheme 2 generally describes the preparation of Pyrazolopyridazine compounds having an $R_3$ group and in which R' is an unsubstituted or a substituted phenyl group. R' and $R_3$ can be the same or different. For example, 4,6-dichloro-3-phenylpyridazine is deprotonated with a base such as lithium diisopropyl amide (LDA) in a solvent such as tetrahydrofuran (THF), and the resultant 5-lithio species is condensed with an unsubstituted or a substituted benzaldehyde to provide a secondary alcohol. The alcohol is oxidized to a ketone with an oxidizing agent such as manganese dioxide in a solvent such as toluene. The ketone is condensed with an $R_3$-substituted hydrazine in a solvent such as ethanol to provide an intermediate hydrazone, which cyclizes to provide a Pyrazolopyridazine compound having a 1-N—$R_3$ group, in which $R_3$ is defined as in Formulas II and III and in which R' is an unsubstituted or a substituted phenyl group.

Scheme 3

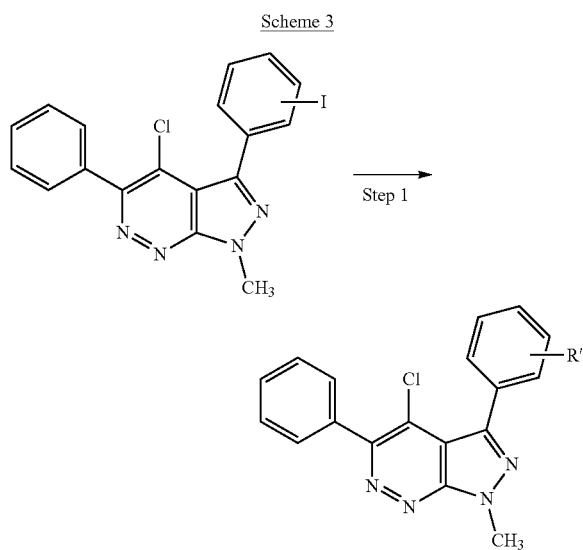

Scheme 3 generally describes the preparation of Pyrazolopyridazine compounds having a 1-N-methyl group and where R' is a cyano group, an alkyne, an alkene or an aryl group. For example, 1-methyl-3-iodophenyl-4-chloro-5-phenyl-1H-pyrazolo[3,4-c]pyridazine is coupled with a suitable coupling partner, such as a cyanide salt, a terminal alkyne, an alkenyl halide, or an aryl halide, optionally in the presence of a suitable catalyst such as a palladium complex, optionally in the presence of a non-palladium transition metal salt such as a zinc or copper salt, optionally in the presence of an additive such as triphenylphosphine or an organic amine base, to provide a Pyrazolopyridazine compound having a 1-N-methyl group and where R' is a cyano group, an alkyne, an alkene or an aryl group. The position of R', i.e., ortho, meta or para, in the product is the same as the position of the iodo group in the starting material.

Therapeutic Uses

A compound of the invention can be administered to a subject in need thereof for the treatment of a retinal degenerative disease. Non-limiting examples of retinal degenerative diseases include: retinitis pigmentosa, Leber's congenital Amaurosis, Syndromic retinal degenerations, age-related macular degeneration including wet and dry age-related macular degeneration, and Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

In a further embodiment of the invention, a compound of the invention can be administered to a subject in need thereof for the treatment of hearing loss associated with Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

A "subject" is a mammal, e.g., a human, mouse, rat, guinea pig, dog, cat, horse, cow, pig, or non-human primate, such as a monkey, chimpanzee, baboon or rhesus. In one embodiment, the subject is a human.

The compounds of the invention can be administered to a subject as a component of a composition that comprises a pharmaceutically acceptable carrier or vehicle. Non-limiting examples of suitable pharmaceutical carriers or vehicles include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, and phosphate buffered saline. These compositions can be administered as, for example, drops, solutions, suspensions, tablets, pills, capsules, powders, and sustained-release formulations. In some embodiments, the compositions comprise, for example, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate, and mineral oil. The compositions can additionally comprise lubricating agents, wetting agents, emulsifying and suspending agents, preserving agents, sweetening agents or flavoring agents.

The compositions can comprise an effective amount of a compound of the invention. An "effective amount" of a compound of the invention is an amount that is effective to treat a retinal degenerative disease or hearing loss associated with Usher Syndrome in a subject. The compositions can be formulated in a unit dosage form that comprises an effective amount of a compound of the invention. In some embodiments, the compositions comprise, for example, from about 1 ng to about 1,000 mg of a compound of the invention. In some embodiments, the compositions comprise from about 100 mg to about 1,000 mg of a compound of the invention. In some embodiments, the compositions comprise from about 100 mg to about 500 mg of a compound of the invention. In some embodiments, the compositions comprise from about 200 mg to about 300 mg of a compound of the invention.

The dosage of a compound of the invention can vary depending on the symptoms, age, and body weight of the subject, the nature and severity of the retinal degenerative disease or hearing loss associated with Usher Syndrome, the route of administration, and the form of the composition. The compositions described herein can be administered in a single dose or in divided doses. In some embodiments, the dosage of a compound of the invention ranges from about 0.01 ng to about 10 g per kg body mass of the subject, from about 1 ng to about 0.1 g per kg, or from about 100 ng to about 10 mg per kg.

Administration can be, for example, topical, intraaural, intraocular, parenteral, intravenous, intra-arterial, subcutaneous, intramuscular, intracranial, intraorbital, intraventricular, intracapsular, intraspinal, intracisternal, intraperitoneal, intranasal, aerosol, suppository, or oral. Formulations for oral use include tablets containing a compound of the invention in a mixture with non-toxic pharmaceutically acceptable excipients. These excipients can be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for ocular use can be in the form of eyedrops.

A compound of the invention or composition thereof can be provided in lyophilized form for reconstituting, for instance, in isotonic, aqueous, or saline buffers for parental, subcutaneous, intradermal, intramuscular, or intravenous administration. A composition of the invention can also be in the form of a liquid preparation useful for oral, intraaural, nasal, or sublingual administration, such as a suspension, syrup or elixir. A composition of the invention can also be in a form suitable for oral administration, such as a capsule, tablet, pill, and chewable solid formulation. A composition of the invention can also be prepared as a cream for dermal administration as a liquid, a viscous liquid, a paste, or a powder. A composition of the invention can also be prepared as a powder for pulmonary administration with or without an aerosolizing component.

The compositions can be in oral, intraaural, intranasal, sublingual, intraduodenal, subcutaneous, buccal, intracolonic, rectal, vaginal, mucosal, pulmonary, transdermal, intradermal, parenteral, intravenous, intramuscular and ocular dosage forms as well as being able to traverse the blood-brain barrier.

The compositions of the invention can be administered by various means known in the art. For example, the compositions of the invention can be administered orally, and can be formulated as tablets, capsules, granules, powders or syrups. Alternatively, compositions of the invention can be administered parenterally as injections (for example, intravenous, intramuscular or subcutaneous), drop infusion preparations or suppositories. For ophthalmic application compositions of the invention can be formulated as eye drops or eye ointments. Aural compositions can be formulated as ear drops, ointments, creams, liquids, gels, or salves for application to the ear, either internally or superficially. These formulations can be prepared by conventional means, and the compositions can be mixed with any conventional additive, such as an excipient, a binder, a disintegrating agent, a lubricant, a solubilizing agent, a suspension aid, an emulsifying agent, or a coating agent.

Compositions of the invention can include wetting agents, emulsifiers, and lubricants, coloring agents, release agents, coating agents, sweetening, flavoring and perfuming agents, preservatives and antioxidants.

Compositions can be suitable, for example, for oral, intraaural, intraocular, nasal, topical (including buccal and sublingual), rectal, vaginal, aerosol and/or parenteral administration. The compositions can be provided in a unit dosage form, and can be prepared by any methods known in the art.

Formulations suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia. Compositions of the invention can also be administered as a bolus, electuary, or paste.

Additional examples of pharmaceutically acceptable carriers or vehicles include: (1) fillers or extenders, such as starches, lactose, sucrose, glucose, mannitol, and/or silicic acid; (2) binders, such as carboxymethyl cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; (10) coloring agents; and (11) buffering agents. Similar compositions can be employed as fillers in soft- or hard-filled gelatin capsules.

Liquid dosage forms for oral administration include pharmaceutically acceptable emulsions, microemulsions, gels, solutions, suspensions, syrups and elixirs. The liquid dosage form can contain inert diluents commonly used in the art, for example, water or other solvents, solubilizing agents and emulsifiers, such as ethyl alcohol, isopropyl alcohol, diethyl carbonate, ethyl acetate, benzyl alcohol, benzyl benzoate, propylene glycol, 1,3-butylene glycol, oils such as, cottonseed, groundnut, corn, germ, olive, castor and sesame oils, glycerol, tetrahydrofuryl alcohol, polyethylene glycols, fatty acid esters of sorbitan, and mixtures thereof.

Suspension dosage forms can contain suspending, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The dosage forms for transdermal administration of a subject composition include drops, powders, sprays, ointments, pastes, creams, lotions, gels, solutions, and patches. The ointments, pastes, creams, and gels can contain excipients, such as animal and vegetable fats, oils, waxes, paraffin, starch, tragacanth, cellulose derivatives, polyethylene glycols, silicones, bentonite, silicic acid, talc and zinc oxide, or mixtures thereof.

Powders and sprays can contain excipients such as lactose, talc, silicic acid, aluminum hydroxide, calcium silicates, polyamide powder, or mixtures thereof. Sprays may additionally contain customary propellants, such as chlorofluorohydrocarbons and volatile unsubstituted hydrocarbons, such as butane and propane.

Compositions can be administered by aerosol of solid particles. A non-aqueous (e.g., fluorocarbon propellant) suspension could be used. Sonic nebulizers can be used because they minimize exposure to shear, which might cause degradation.

An aqueous aerosol can be made by formulating an aqueous solution or suspension of a compound of the invention with any conventional pharmaceutically acceptable carriers or vehicles such non-ionic surfactants (Tweens, Pluronics, or polyethylene glycol); proteins such as serum albumin; sorbitan esters; fatty acids; lecithin; amino acids; buffers; salts; sugars; or sugar alcohols.

Compositions suitable for parenteral administration comprise a compound of the invention and one or more pharmaceutically acceptable sterile isotonic aqueous or non-aqueous solutions, dispersions, suspensions, or emulsions, or sterile powders which can be reconstituted into sterile injectable solutions or dispersions just prior to use, which can contain antioxidants, buffers, bacteriostats, or solutes, which render the formulation isotonic with the blood of the subject, and suspending or thickening agents.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1: 4-chloro-3-(2-chlorophenyl)-1-methyl-5-phenyl-1H-pyrazolo[3,4-c]pyridazine (Compound 37)

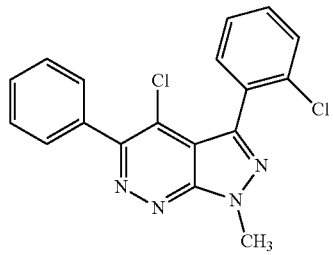 [SMILES: Cn1nc(-c2ccccc2Cl)c2c(Cl)c(-c3ccccc3)nnc21]

Step 1: 3-(2-chlorophenyl)-1-methyl-1H-pyrazol-5-amine

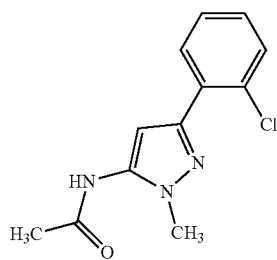 [SMILES: CC(=O)Nc1cc(-c2ccccc2Cl)nn1C]

A mixture of 2-chlorobenzoylacetonitrile (540 mg, 3 mmol) and methylhydrazine (158 µl, 3 mmol) in methanol (3 mL) was heated at 120° C. for 1 hour in a microwave. The reaction mixture was concentrated in vacuo to give 3-(2-chlorophenyl)-1-methyl-1H-pyrazol-5-amine as a solid (617 mg), which was used as such in the subsequent step.

Step 2: N-(3-(2-chlorophenyl)-1-methyl-1H-pyrazol-5-yl)acetamide

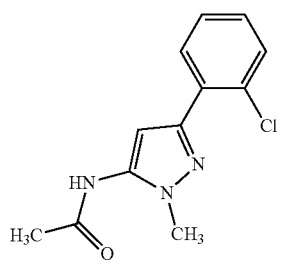

To a solution of 3-(2-chlorophenyl)-1-methyl-1H-pyrazol-5-amine (617 mg, 3 mmol) in pyridine (6 mL) was added acetic anhydride (425 µl, 4.5 mmol). The reaction was stirred at room temperature for 16 h. The mixture was concentrated in vacuo. The crude residue was purified by column chromatography (silica gel, gradient 0 to 100% ethyl acetate/isohexane) yielding N-(3-(2-chlorophenyl)-1-methyl-1H-pyrazol-5-yl)acetamide as a solid (526 mg).

Step 3: N-(3-(2-chlorophenyl)-4-iodo-1-methyl-1H-pyrazol-5-yl)acetamide

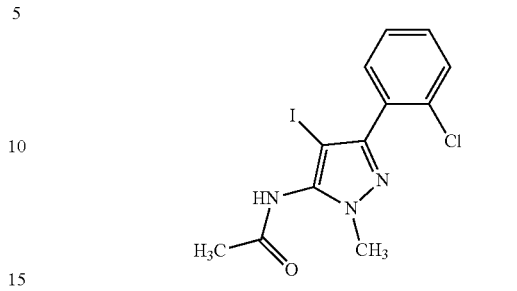

To a solution of N-(3-(2-chlorophenyl)-1-methyl-1H-pyrazol-5-yl)acetamide (526 mg, 2.12 mmol) in ethanol (16 mL) were added iodic acid (93 mg, 0.53 mmol) and iodine (294 mg, 1.16 mmol). The reaction was stirred for 18 h at 50° C. The reaction mixture was concentrated in vacuo and the residue was dissolved in $CH_2Cl_2$ and washed with a 2 N $Na_2SO_3$ solution. The organic phase was dried over $MgSO_4$, filtered and evaporated to give N-(3-(2-chlorophenyl)-4-iodo-1-methyl-1H-pyrazol-5-yl)acetamide as a light orange solid (756 mg), which was used as such in the subsequent step.

Step 4: N-(3-(2-chlorophenyl)-1-methyl-4-(phenylethynyl)-1H-pyrazol-5-yl)acetamide

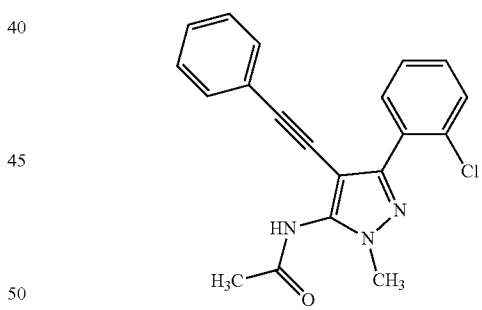

To a degassed solution of phenylacetylene (157 µl, 1.43 mmol) and $Et_3N$ (3.3 mL) in DMF (1.2 mL) were added N-(3-(2-chlorophenyl)-4-iodo-1-methyl-1H-pyrazol-5-yl)acetamide (413 mg, 1.1 mmol), CuI (42 mg, 0.22 mmol) and $PdCl_2(PPh_3)_2$ (77 mg, 0.11 mmol). The mixture was flushed with $N_2$ and then heated to 85° C. for 3 h. The reaction mixture was concentrated in vacuo and the residue was purified by column chromatography (silica gel, gradient 0 to 100% ethyl acetate/isohexane) yielding N-(3-(2-chlorophenyl)-1-methyl-4-(phenylethynyl)-1H-pyrazol-5-yl)acetamide as a solid (181 mg).

Step 5: 3-(2-chlorophenyl)-1-methyl-4-(phenylethynyl)-1H-pyrazol-5-amine

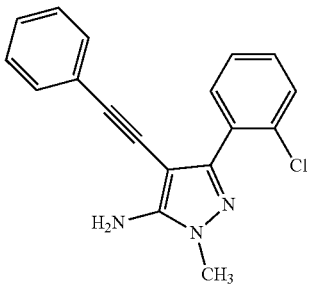 [SMILES: Cn1nc(-c2ccccc2Cl)c(C#Cc2ccccc2)c1N]

A solution of N-(3-(2-chlorophenyl)-1-methyl-4-(phenylethynyl)-1H-pyrazol-5-yl)acetamide (170 mg, 0.49 mmol) in ethanol (1 mL) and 25% NaOH (1.4 mL) was heated to 85° C. for 30 h. The reaction mixture was partitioned between ethyl acetate and water. The aqueous phase was washed with ethyl acetate and the organic phases combined, dried over $MgSO_4$, filtered and evaporated to give 3-(2-chlorophenyl)-1-methyl-4-(phenylethynyl)-1H-pyrazol-5-amine as a solid (136 mg), which was used as such in the subsequent step.

Step 6: 4-chloro-3-(2-chlorophenyl)-1-methyl-5-phenyl-1H-pyrazolo[3,4-c]pyridazine (Compound 37)

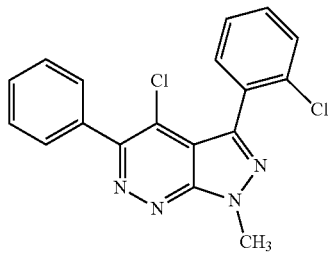 [SMILES: Cn1nc(-c2ccccc2Cl)c2c(Cl)c(-c3ccccc3)nnc21]

To a cooled (cooling bath −15° C.) stirred suspension of 3-(2-chlorophenyl)-1-methyl-4-(phenylethynyl)-1H-pyrazol-5-amine (136 mg, 0.44 mmol) in conc. HCl (3.7 mL) was added a solution of sodium nitrite (34 mg, 0.49 mmol) in water (0.3 mL). After 5 min, the cooling bath was removed and the reaction mixture was stirred at room temperature for 1 h. The reaction was cooled again (0° C.) and poured onto a sat. $NaHCO_3$ solution. Ethyl acetate was added and pH was adjusted to 7-8 with sat. $NaHCO_3$. The aqueous phase was extracted with ethyl acetate and the organic phases combined, dried over $MgSO_4$, filtered and evaporated. Crude material was purified by column chromatography (silica gel, gradient 0 to 4% ethyl acetate/$CH_2Cl_2$) yielding Compound 37 as a solid (47 mg).

LCMS (10 cm_ESCI_Formic) Rt 4.72 min; m/z 355 [M+H] 97.96% purity.

Example 2: 4-chloro-3-(3-methoxyphenyl)-1-methyl-5-phenyl-1H-pyrazolo[3,4-c]pyridazine (Compound 17)

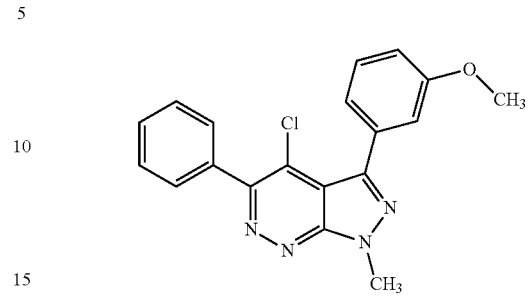

Compound 17 was synthesised following similar procedures outlined in Example 1 (Compound 37), using 3-methoxybenzoylacetonitrile instead of 2-chlorobenzoyl acetonitrile in Step 1.

LCMS (10 cm_ESCI_Formic) Rt 4.6 min; m/z 351 [M+H] 96.23% purity.

Example 3: 4-chloro-3-(4-methoxyphenyl)-1-methyl-5-phenyl-1H-pyrazolo[3,4-c]pyridazine (Compound 27)

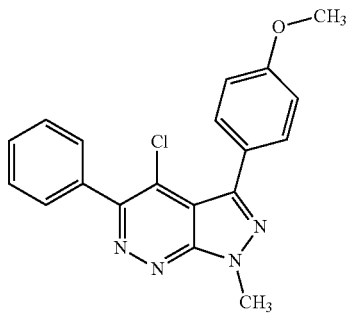 [SMILES: COc1ccc(-c2nn(C)c3nnc(-c4ccccc4)c(Cl)c23)cc1]

Compound 27 was synthesised following similar procedures outlined in Example 1 (Compound 37), using 4-methoxybenzoylacetonitrile instead of 2-chlorobenzoyl acetonitrile in Step 1.

LCMS (10 cm_ESCI_Bicarb) Rt 3.97 min; m/z 351 [M+H] 96.77% purity.

Example 4: 4-chloro-3-(3-chlorophenyl)-1-methyl-5-phenyl-1H-pyrazolo[3,4-c]pyridazine (Compound 13)

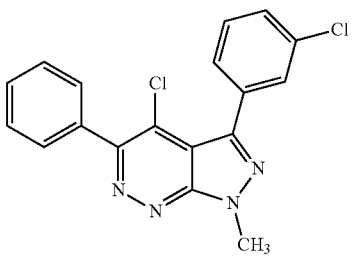 [SMILES: Cn1nc(-c2cccc(Cl)c2)c2c(Cl)c(-c3ccccc3)nnc21]

Compound 13 was synthesised following similar procedures outlined in Example 1 (Compound 37), using 3-chlorobenzoylacetonitrile instead of 2-chlorobenzoyl acetonitrile in Step 1.

LCMS (10 cm_ESI_Bicarb) Rt 4.16 min; m/z 355 [M+H] 98.38% purity.

Example 5: 4-chloro-3-(3-methoxyphenyl)-5-(4-methoxyphenyl)-1-methyl-1H-pyrazolo[3,4-c]pyridazine (Compound 15)

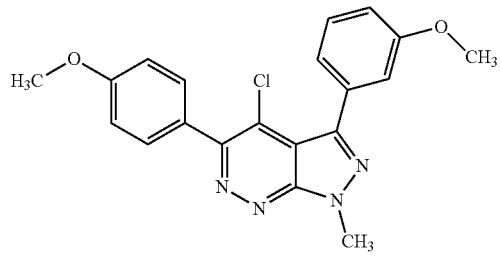

Compound 15 was synthesised following similar procedures outlined in Example 1 (Compound 37), using 3-methoxybenzoylacetonitrile instead of 2-chlorobenzoyl acetonitrile in Step 1 and 4-methoxyphenyl acetylene instead of phenyl acetylene in Step 4.

LCMS (10 cm_ESCI_Bicarb) Rt 4.3 min; m/z 381 [M+H] 95.3% purity.

Example 6: 4-chloro-3,5-bis(4-fluorophenyl)-1-methyl-1H-pyrazolo[3,4-c]pyridazine (Compound 33)

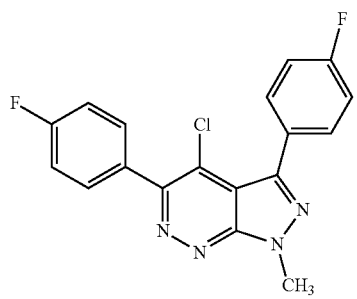 [SMILES: Cn1nc(-c2ccc(F)cc2)c2c(Cl)c(-c3ccc(F)cc3)nnc21]

Compound 33 was synthesised following similar procedures outlined in Example 1 (Compound 37), using 4-fluorobenzoylacetonitrile instead of 2-chlorobenzoyl acetonitrile in Step 1. As a slightly modified procedure, the residue of Step 1 was purified by column chromatography (silica gel, gradient 30 to 100% EtOAc/isohexane). The residue of Step 3 was dissolved in $CH_2Cl_2$ and washed with an aqueous $Na_2S_2O_3$ solution. Product of Step 3 was purified by column chromatography (silica gel, gradient 0 to 100% ethyl acetate/$CH_2Cl_2$. 4-fluorophenyl acetylene was used instead of phenyl acetylene in Step 4. The reaction mixture of Step 4 was worked up with $CH_2Cl_2$, water and $K_2CO_3$ instead of EtOAc, aq. sat. $NaHCO_3$. The residue was purified by column chromatography (silica gel, gradient 10 to 100% EtOAc/isohexane) to provide Compound 33.

LCMS (10 cm_ESCI_Formic) Rt 4.18 min; m/z 357 [M+H] 99.63% purity.

Example 7: 4-chloro-1-methyl-3,5-diphenyl-1H-pyrazolo[3,4-c]pyridazine (Compound 39)

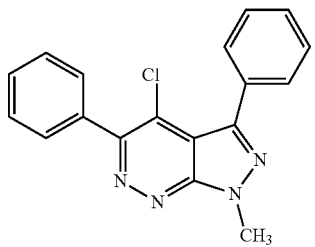 [SMILES: Cn1nc(-c2ccccc2)c2c(Cl)c(-c3ccccc3)nnc21]

Compound 39 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine.

LCMS (10 cm_ESCI_Bicarb) Rt 4.39 min; m/z 321 [M+H] 95.87% purity.

Example 8: 4-chloro-3-(4-chlorophenyl)-1-methyl-5-phenyl-1H-pyrazolo[3,4-c]pyridazine (Compound 26)

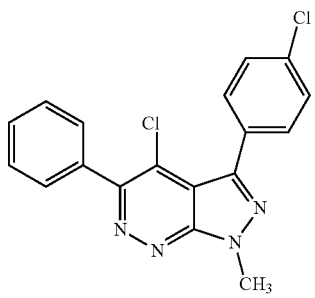 [SMILES: Cn1nc(-c2ccc(Cl)cc2)c2c(Cl)c(-c3ccccc3)nnc21]

Compound 26 was synthesised following similar procedures outlined in Example 1 (Compound 37), starting from Step 2 using 3-(4-chlorophenyl)-1-methyl-1H-pyrazol-5-amine instead of 3-(2-chlorophenyl)-1-methyl-1H-pyrazol-5-amine.

LCMS (10 cm_ESCI_Formic) Rt 4.91 min; m/z 355 [M+H] 99.36% purity.

Example 9: 4-chloro-5-(4-fluorophenyl)-1-methyl-3-phenyl-1H-pyrazolo[3,4-c]pyridazine (Compound 4)

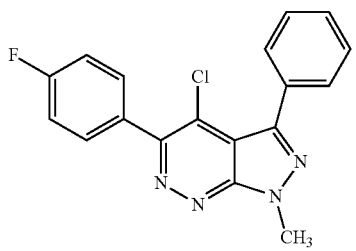 [SMILES: Cn1nc(-c2ccccc2)c2c(Cl)c(-c3ccc(F)cc3)nnc21]

Compound 4 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine and 4-fluorophenylacetylene instead of phenyl acetylene in Step 4.

LCMS (15 cm_Bicarb_GeminiNX_HPLC) Rt 11.15 min; m/z 339 [M+H] 97.86% purity.

Example 10: 4-Chloro-5-(4-methoxyphenyl)-1-methyl-3-phenyl-1H-pyrazolo[3,4-c]pyridazine (Compound 8)

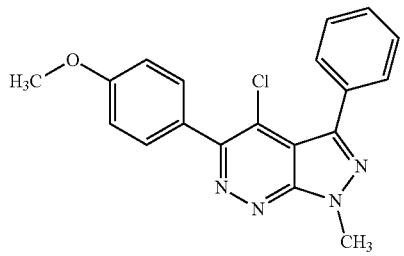 [SMILES: COc1ccc(-c2nnc3c(c(-c4ccccc4)nn3C)c2Cl)cc1]

Compound 8 was synthesised following similar procedures outlined in Example 6 (Compound 33), starting from Step 2 using 1-methyl-3-phenyl-1H-pyrazol-5-amine instead of 3-(4-fluorophenyl)-1-methyl-1H-pyrazol-5-amine.

LCMS (15 cm_Formic_ASCENTIS_HPLC) Rt 10.61 min; m/z 351 [M+H] 98.07% purity.

Example 11: 4-Chloro-3-(4-fluorophenyl)-1-methyl-5-phenyl-1H-pyrazolo[3,4-c]pyridazine (Compound 14)

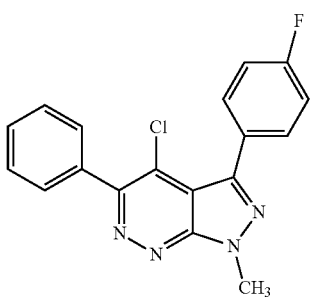 [SMILES: Cn1nc(-c2ccc(F)cc2)c2c(Cl)c(-c3ccccc3)nnc21]

Compound 14 was synthesised following similar procedures outlined in Example 1 (Compound 37), starting from Step 2 using 3-(4-fluorophenyl)-1-methyl-1H-pyrazol-5-amine instead of 3-(2-chlorophenyl)-1-methyl-1H-pyrazol-5-amine.

LCMS (10 cm_ESI_Bicarb) Rt 3.88 min; m/z 339 [M+H] 98.17% purity.

Example 12: 4-Chloro-5-(3-fluorophenyl)-1-methyl-3-phenyl-1H-pyrazolo[3,4-c]pyridazine (Compound 10)

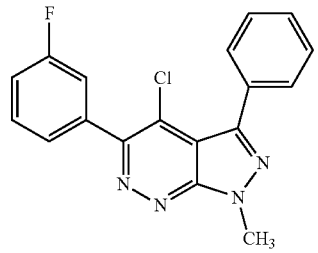 [SMILES: Cn1nc(-c2ccccc2)c2c(Cl)c(-c3cccc(F)c3)nnc21]

Compound 10 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine and 3-fluorophenylacetylene instead of phenyl acetylene in Step 4.

LCMS (10 cm_ESI_Formic) Rt 4.18 min; m/z 339 [M+H] 96.5% purity.

Example 13: 4-Chloro-1-methyl-3-phenyl-5-p-tolyl-1H-pyrazolo[3,4-c]pyridazine (Compound 11)

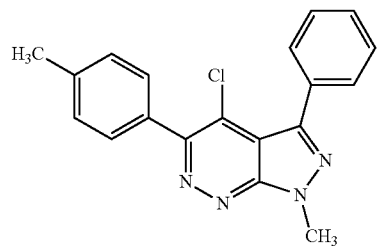 [SMILES: Cc1ccc(-c2nnc3c(c(-c4ccccc4)nn3C)c2Cl)cc1]

Compound 11 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine and 4-tolylacetylene instead of phenyl acetylene in Step 4.

LCMS (10 cm_ESI_Bicarb) Rt 4.07 min; m/z 335 [M+H] 98.54% purity.

Example 14: 4-Chloro-1-methyl-3-phenyl-5-m-tolyl-1H-pyrazolo[3,4-c]pyridazine (Compound 16)

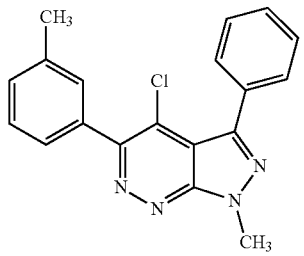 [SMILES: Cn1nc(-c2ccccc2)c2c(Cl)c(-c3cccc(C(F)(F)F)c3)nnc21]

Compound 16 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine and 3-tolylacetylene instead of phenyl acetylene in Step 4.

LCMS (10 cm_ESI_Bicarb) Rt 4.07 min; m/z 335 [M+H] 98.36% purity.

Example 15: 4-chloro-1-methyl-3-phenyl-5-(3-(trifluoromethyl)phenyl)-1H-pyrazolo[3,4-c]pyridazine (Compound 29)

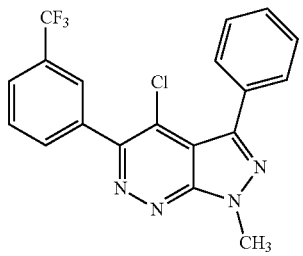

Compound 29 was synthesised following similar procedures outlined in Example 1 (Compound 37), starting from Step 2 using 1-methyl-3-phenyl-1H-pyrazol-5-amine instead of 3-(2-chlorophenyl)-1-methyl-1H-pyrazol-5-amine and 3-(trifluoromethyl)-phenylacetylene instead of phenyl acetylene in Step 4.

LCMS (15 cm_Formic_ASCENTIS_HPLC) Rt 13.11 min; m/z 389 [M+H] 86.58% purity.

Example 16: 2-(4-chloro-3,5-diphenyl-1H-pyrazolo[3,4-c]pyridazin-1-yl)-N-methylacetamide (Compound 5)

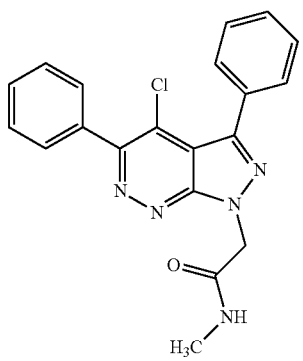 [SMILES: CNC(=O)Cn1nc(-c2ccccc2)c2c(Cl)c(-c3ccccc3)nnc21]

Compound 5 was synthesised from 2-(4-chloro-3,5-diphenyl-1H-pyrazolo[3,4-c]pyridazin-1-yl)acetic acid, which was synthesised following similar procedures outlined in Example 1 (Compound 37), using benzoylacetonitrile instead of 2-chlorobenzoyl acetonitrile and ethyl hydrazinoacetate hydrochloride and 1.5 equivalent of triethylamine instead of methylhydrazine in Step 1. To a suspension of 2-(4-chloro-3,5-diphenyl-1H-pyrazolo[3,4-c]pyridazin-1-yl)acetic acid (73 mg, 0.2 mmol) in $CH_2Cl_2$ (1 mL) were added 2-hydroxypyridine-N-oxide (HOPO) (22 mg, 0.2 mmol), methylamine hydrochloride (14 mg, 0.2 mmol), 1-(3-dimethylaminopropyl)-3-ethylcarbodiimide hydrochloride (EDAC) (50 mg, 0.25 mmol), diisopropylethylamine (DIPEA) (90 µl, 0.2 mmol) and DMF (0.5 mL). The reaction mixture was stirred at room temperature for 90 min then concentrated in vacuo. The residue was purified by preparative HPLC yielding Compound 5 as an off-white solid (6 mg).

LCMS (15 cm_Bicarb_GeminiNX_HPLC) Rt 10.02 min; m/z 378 [M+H] 94.61% purity.

Example 17: 2-(4-Chloro-3,5-diphenyl-1H-pyrazolo[3,4-c]pyridazin-1-yl)-1-(4-methylpiperazin-1-yl)ethanone (Compound 1)

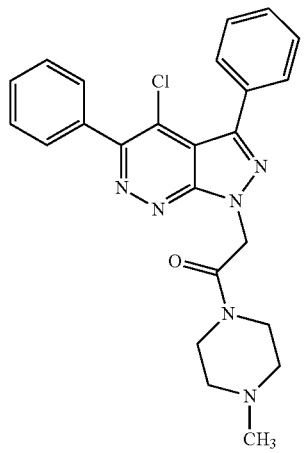 [SMILES: CN1CCN(C(=O)Cn2nc(-c3ccccc3)c3c(Cl)c(-c4ccccc4)nnc32)CC1]

Compound 1 was synthesised from 2-(4-chloro-3,5-diphenyl-1H-pyrazolo[3,4-c]pyridazin-1-yl)acetic acid following a similar procedure outlined in Example 16 (Compound 5), using N-methylpiperazine instead of methylamine hydrochloride in the final step. The residue in the final step was purified by preparative HPLC, followed by column chromatography (silica gel, gradient 0 to 5% triethylamine/acetone), yielding the Compound 1 as an off-white solid (6 mg).

LCMS (15 cm_Bicarb_GeminiNX_HPLC) Rt 10.12 min; m/z 447 [M+H] 96.8% purity.

Example 18: 2-(4-Chloro-3,5-diphenyl-1H-pyrazolo[3,4-c]pyridazin-1-yl)-N-(2-(dimethylamino)ethyl)acetamide (Compound 2)

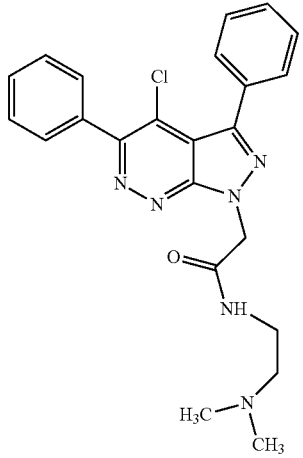 [SMILES: CN(C)CCNC(=O)Cn1nc(-c2ccccc2)c2c(Cl)c(-c3ccccc3)nnc21]

Compound 2 was synthesised from 2-(4-chloro-3,5-diphenyl-1H-pyrazolo[3,4-c]pyridazin-1-yl)acetic acid following a similar procedure outlined in Example 17 (Compound 1), using N,N'-dimethylethylenediamine instead of N-methylpiperazine in the final step.

LCMS (15 cm_Formic_ASCENTIS_HPLC) Rt 7.68 min; m/z 435 [M+H] 95.51% purity.

Example 19: 2-(4-Chloro-3,5-diphenyl-1H-pyrazolo[3,4-c]pyridazin-1-yl)-1-(4-isopropylpiperazin-1-yl)ethanone (Compound 38)

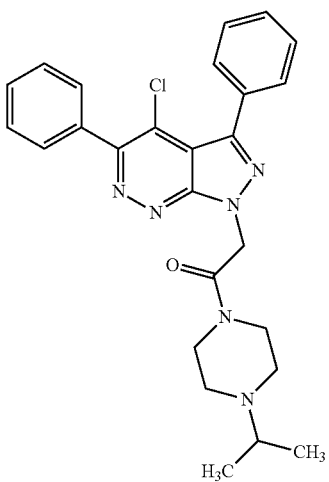 [SMILES: CC(C)N1CCN(C(=O)Cn2nc(-c3ccccc3)c3c(Cl)c(-c4ccccc4)nnc32)CC1]

Compound 38 was synthesised from 2-(4-chloro-3,5-diphenyl-1H-pyrazolo[3,4-c]pyridazin-1-yl)acetic acid following a similar procedure outlined in Example 17 (Compound 1), using N-isopropylpiperazine instead of N-methylpiperazine in the final step.

LCMS (15 cm_Formic_ASCENTIS_HPLC) Rt 12.54 min; m/z 475 [M+H] 95.82% purity.

Example 20: 4-(4-Chloro-1-methyl-5-phenyl-1H-pyrazolo[3,4-c]pyridazin-3-yl)-N-methylbenzamide (Compound 25)

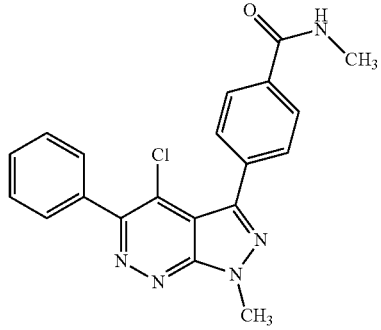 [SMILES: CNC(=O)c1ccc(-c2nn(C)c3nnc(-c4ccccc4)c(Cl)c23)cc1]

Compound 25 was synthesised following similar procedures outlined in Example 1 (Compound 37), using methyl 4-(cyanoacetyl)benzoate instead of 2-chlorobenzoyl acetonitrile in Step 1. 4-(5-Amino-1-methyl-4-(phenylethynyl)-1H-pyrazol-3-yl)benzoic acid obtained in Step 5 was converted to 4-(5-amino-1-methyl-4-(phenylethynyl)-1H-pyrazol-3-yl)-N-methylbenzamide following a similar procedure outlined in Example 16 (Compound 5). 4-(5-Amino-1-methyl-4-(phenylethynyl)-1H-pyrazol-3-yl)-N-methylbenzamide was converted to the Compound 25 following a similar procedure outlined in Step 5 of Example 5.

LCMS (10 cm_ESI_Formic) Rt 3.1 min; m/z 378 [M+H] 99.89% purity.

Example 21: 2-(4-Chloro-3,5-diphenyl-1H-pyrazolo[3,4-c]pyridazin-1-yl)-N-(3-(7-nitrobenzo[c][1,2,5]oxadiazol-4-ylamino)propyl)acetamide (Compound 6)

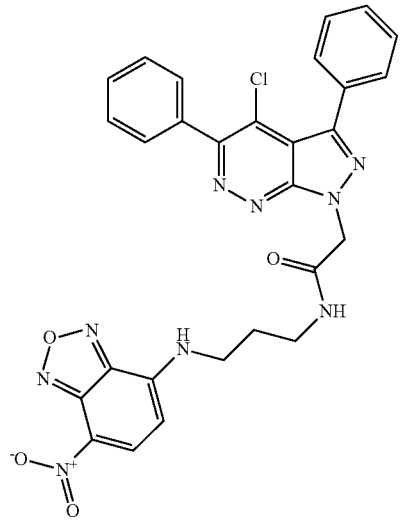

Compound 6 was synthesised from 2-(4-chloro-3,5-diphenyl-1H-pyrazolo[3,4-c]pyridazin-1-yl)acetic acid following a similar procedure outlined in Example 16 (Compound 5), using N1-(7-nitrobenzo[c][1,2,5]oxadiazol-4-yl)propane-1,3-diamine instead of methylamine hydrochloride in the final step.

LCMS (10 cm_ESI_Bicarb) Rt 3.59 min; m/z 584 [M+H] 97.74% purity.

Example 22: 4-Chloro-3,5-diphenyl-1H-pyrazolo[3,4-c]pyridazine (Compound 9)

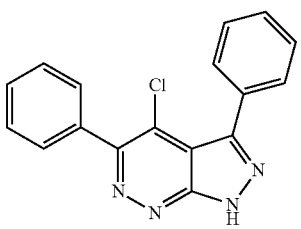 [SMILES: Clc1c(-c2ccccc2)nnc2[nH]nc(-c3ccccc3)c12]

Step 1: (3,5-dichloro-6-phenylpyridazin-4-yl)(phenyl)methanol

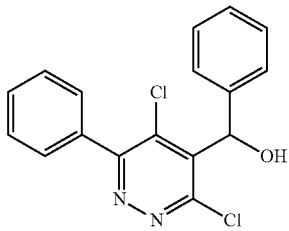 [SMILES: OC(c1ccccc1)c1c(Cl)nnc(-c2ccccc2)c1Cl]

To a solution of LDA (2 M in THF, 2.4 mL, 4.7 mmol) in THF (8 mL) at −78° C. was added dropwise a solution of 3-phenyl-4,6-dichloropyridazine (700 mg, 3.1 mmol) in THF (2 mL). After 30 min at −78° C., benzaldehyde (400 mg, 3.75 mmol) was added. The reaction mixture was allowed to warm up to room temperature overnight. The reaction mixture was partitioned between ethyl acetate and water. The aqueous phase was extracted with ethyl acetate and the organic phases were combined, washed with water and brine, dried over MgSO$_4$, filtered and concentrated in vacuo. The crude residue was purified by column chromatography (silica gel, gradient 10 to 20% ethyl acetate/isohexane) yielding 3,5-dichloro-6-phenylpyridazin-4-yl)(phenyl)methanol as a yellow solid (200 mg).

Step 2: (3,5-dichloro-6-phenylpyridazin-4-yl)(phenyl)methanone

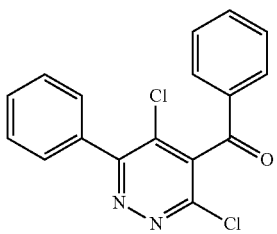 [SMILES: O=C(c1ccccc1)c1c(Cl)nnc(-c2ccccc2)c1Cl]

A mixture of (3,5-dichloro-6-phenylpyridazin-4-yl)(phenyl)methanol (200 mg, 0.6 mmol), manganese dioxide (700 mg, 8 mmol) in dry toluene (20 mL) was heated at 115° C. for 3 h under Dean Stark conditions. The reaction mixture was cooled and filtered, and the residue was washed with CH$_2$Cl$_2$. The filtrate was concentrated in vacuo. The crude residue was purified by column chromatography (silica gel, gradient 10 to 20% ethyl acetate/isohexane) yielding (3,5-dichloro-6-phenylpyridazin-4-yl)(phenyl)methanone as a solid (150 mg).

Step 3: 4-chloro-3,5-diphenyl-1H-pyrazolo[3,4-c]pyridazine (Compound 9)

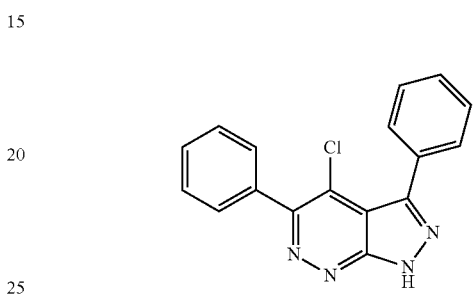

A mixture of (3,5-dichloro-6-phenylpyridazin-4-yl)(phenyl)methanone (150 mg, 0.46 mmol) and hydrazine hydrate (27 mg, 0.55 mmol) in ethanol (0.5 mL) was stirred at 40° C. for 1 h in a sealed tube. The reaction mixture was cooled and filtered, and the residue was washed with diethyl ether. The filtrate was concentrated in vacuo. The crude residue was purified by column chromatography (silica gel, gradient 0 to 20% ethyl acetate/isohexane) yielding Compound 9 as a white solid (12 mg).

LCMS (10 cm_ESCI_Formic) Rt 4.16 min; m/z 307 [M+H] 95.8% purity.

Example 23: 4-Chloro-3-(4-iodophenyl)-1-methyl-5-phenyl-1H-pyrazolo[3,4-c]pyridazine (Compound 43)

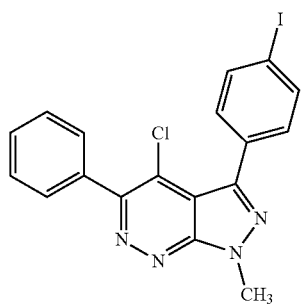 [SMILES: Cn1nc(-c2ccc(I)cc2)c2c(Cl)c(-c3ccccc3)nnc21]

Compound 43 was synthesised following similar procedures outlined in Example 22 (Compound 9), using 4-iodobenzaldehyde instead of benzaldehyde in Step 1 and methyl hydrazine instead of hydrazine hydrate in Step 3. As a slightly modified procedure, Step 3 was performed at 60° C. for 4 h in a sealed tube. Subsequently, the mixture was cooled and filtered, and the residue was washed with cold ethanol. The filtered residue was purified by column chromatography (silica gel, gradient 5 to 10% ethyl acetate/isohexane) yielding Compound 43 as an off-white solid.

LCMS (15 cm_Bicarb_GeminiNX_HPLC) Rt 12.63 min; m/z 447 [M+H] 97.4% purity.

Example 24: 4-chloro-1-methyl-5-phenyl-3-m-tolyl-1H-pyrazolo[3,4-c]pyridazine (Compound 19)

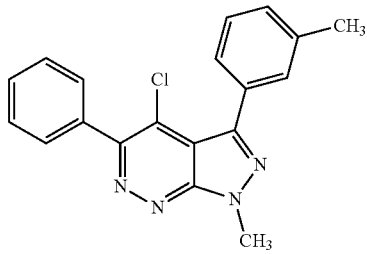 [SMILES: Cc1cccc(-c2nn(C)c3nnc(-c4ccccc4)c(Cl)c23)c1]

Compound 19 was synthesised following similar procedures outlined in Example 22 (Compound 9), using 3-methylbenzaldehyde instead of benzaldehyde in Step 1 and methyl hydrazine instead of hydrazine hydrate in Step 3. As a slightly modified procedure, Step 3 was performed at 60° C. for 16 h in a sealed tube. Subsequently, the reaction mixture was partitioned between $CH_2Cl_2$ and water. The organic phase was separated using a phase separating cartridge and concentrated in vacuo. The crude residue was purified by column chromatography (silica gel, gradient 5 to 20% ethyl acetate/isohexane) yielding Compound 19 as a solid.

LCMS (15 cm_Bicarb_GeminiNX_HPLC) Rt 11.47 min; m/z 335 [M+H] 97.18% purity.

Example 25: 4-Chloro-1-methyl-5-phenyl-3-o-tolyl-1H-pyrazolo[3,4-c]pyridazine (Compound 20)

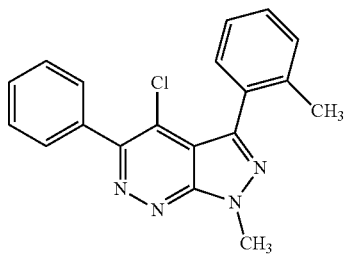 [SMILES: Cc1ccccc1-c1nn(C)c2nnc(-c3ccccc3)c(Cl)c12]

Compound 20 was synthesised following similar procedures outlined in Example 22 (Compound 9), using 2-methylbenzaldehyde instead of benzaldehyde in Step 1 and methyl hydrazine instead of hydrazine hydrate in Step 3.

LCMS (10 cm_ESI_Formic) Rt 4.2 min; m/z 335 [M+H] 98.48% purity.

Example 26: 4-Chloro-1-methyl-5-phenyl-3-p-tolyl-1H-pyrazolo[3,4-c]pyridazine (Compound 21)

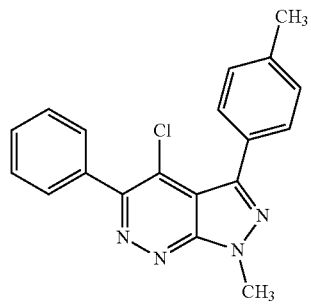 [SMILES: Cc1ccc(-c2nn(C)c3nnc(-c4ccccc4)c(Cl)c23)cc1]

Compound 21 was synthesised following similar procedures outlined in Example 24 (Compound 19), using 4-methylbenzaldehyde instead of 3-methylbenzaldehyde in Step 1. As a slightly modified procedure, Step 3 was performed at 70° C. for 16 h in a sealed tube.

LCMS (15 cm_Bicarb_GeminiNX_HPLC) Rt 11.44 min; m/z 335 [M+H] 97.13% purity.

Example 27: 4-Chloro-3-(2-fluorophenyl)-1-methyl-5-phenyl-1H-pyrazolo[3,4-c]pyridazine (Compound 22)

Compound 22 was synthesised following similar procedures outlined in Example 24 (Compound 19), using 2-fluorobenzaldehyde instead of 3-methylbenzaldehyde in Step 1.

LCMS (10 cm_ESI_Formic) Rt 4.04 min; m/z 339 [M+H] 96.36% purity.

Example 28: 4-Chloro-3-(3-fluorophenyl)-1-methyl-5-phenyl-1H-pyrazolo[3,4-c]pyridazine (Compound 32)

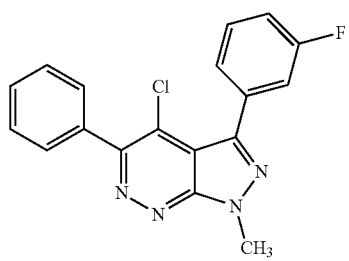 [SMILES: Cn1nc(-c2cccc(F)c2)c2c(Cl)c(-c3ccccc3)nnc21]

Compound 32 was synthesised following similar procedures outlined in Example 24 (Compound 19), using 3-fluorobenzaldehyde instead of 3-methylbenzaldehyde in Step 1.

LCMS (15 cm_Formic_ASCENTIS_HPLC) Rt 12.79 min; m/z 339 [M+H] 98.58% purity.

Example 29: 4-Chloro-1-methyl-5-phenyl-3-(4-(trifluoromethyl)phenyl)-1H-pyrazolo[3,4-c]pyridazine (Compound 23)

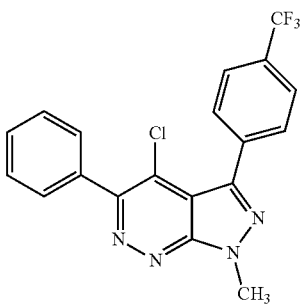 [SMILES: Cn1nc(-c2ccc(C(F)(F)F)cc2)c2c(Cl)c(-c3ccccc3)nnc21]

Compound 23 was synthesised following similar procedures outlined in Example 24 (Compound 19), using 4-trifluoromethylbenzaldehyde instead of 3-methylbenzaldehyde in Step 1. As a slightly modified procedure, in Step 2, the reaction mixture was filtered and following evaporation of the filtrate, purification of (3,5-dichloro-6-phenylpyridazin-4-yl)(4-(trifluoromethyl)phenyl)methanone was carried out by trituration of the solid residue in diethyl ether.

LCMS (10 cm_ESCI_Bicarb) Rt 4.68 min; m/z 389 [M+H] 98.96% purity.

Example 30: 4-Chloro-3-(3-iodophenyl)-1-methyl-5-phenyl-1H-pyrazolo[3,4-c]pyridazine (Compound 3)

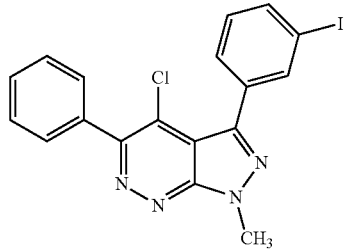 [SMILES: Cn1nc(-c2cccc(I)c2)c2c(Cl)c(-c3ccccc3)nnc21]

Compound 3 was synthesised following similar procedures outlined in Example 25 (Compound 20), using 3-iodobenzaldehyde instead of 2-methylbenzaldehyde in Step 1. As a slightly modified procedure, the crude residue of Step 3 was purified by column chromatography (silica gel, gradient 80 to 100% $CH_2Cl_2$/isohexane to 2% diethyl ether/$CH_2Cl_2$), yielding Compound 3 as a solid.

LCMS (10 cm_ESCI_Formic) Rt 5.03 min; m/z 447 [M+H] 99.13% purity.

Example 31: 4-Chloro-1-ethyl-3,5-diphenyl-1H-pyrazolo[3,4-c]pyridazine (Compound 18)

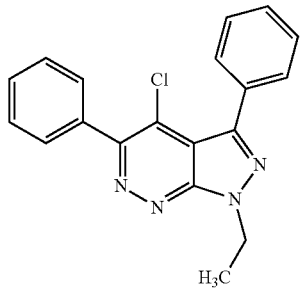 [SMILES: CCn1nc(-c2ccccc2)c2c(Cl)c(-c3ccccc3)nnc21]

Compound 18 was synthesised following similar procedures outlined in Example 22 (Compound 9), using ethyl hydrazine instead of hydrazine hydrate in Step 3. As a slightly modified procedure, Step 3 was performed at 90° C. for 16 h in a sealed tube. Subsequently, the reaction mixture was partitioned between $CH_2Cl_2$ and water. The organic phase was separated using a phase separating cartridge and concentrated in vacuo. The crude residue was purified by column chromatography (silica gel, 5% ethyl acetate/isohexane) yielding Compound 18 as a solid.

LCMS (15 cm_Bicarb_GeminiNX_HPLC) Rt 11.52 min; m/z 335 [M+H] 94.7% purity.

Example 32: 2-(4-chloro-3,5-diphenyl-1H-pyrazolo[3,4-c]pyridazin-1-yl)ethanol (Compound 7)

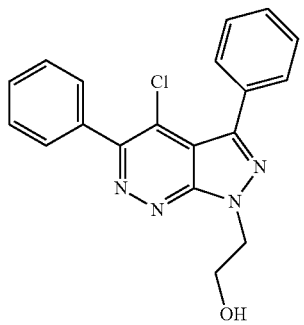 [SMILES: OCCn1nc(-c2ccccc2)c2c(Cl)c(-c3ccccc3)nnc21]

Compound 7 was synthesised following similar procedures outlined in Example 31 (Compound 18), using 2-hydroxyethyl hydrazine instead of ethyl hydrazine in Step 3. As a slightly modified procedure, Step 3 was performed at 90° C. for 30 min in the microwave. The crude residue was purified by column chromatography (silica gel, gradient 10 to 50% ethyl acetate/isohexane), yielding Compound 7 as a solid.

LCMS (15 cm_Bicarb_GeminiNX_HPLC) Rt 10.29 min; m/z 351 [M+H] 95.59% purity.

Example 33: 1-Benzyl-4-chloro-3,5-diphenyl-1H-pyrazolo[3,4-c]pyridazine (Compound 31)

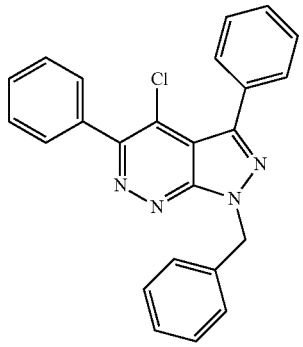 [SMILES: Clc1c(-c2ccccc2)nnc2c1c(-c1ccccc1)nn2Cc1ccccc1]

Compound 31 was synthesised following similar procedures outlined in Example 31 (Compound 18), using benzyl hydrazine dihydrochloride instead of ethyl hydrazine in Step 3. As a slightly modified procedure, Step 3 was performed at 50° C. for 16 h. The crude residue was purified by column chromatography (silica gel, gradient 5 to 10% ethyl acetate/isohexane), followed by preparative HPLC, yielding Compound 31 as a solid.

LCMS (15 cm_Formic_ASCENTIS_HPLC) Rt 11.04 min; m/z 397 [M+H] 98.71% purity.

Example 34: 4-(2-(4-chloro-3,5-diphenyl-1H-pyrazolo[3,4-c]pyridazin-1-yl)ethyl)morpholine (Compound 28)

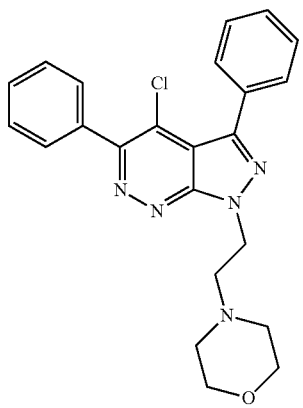 [SMILES: Clc1c(-c2ccccc2)nnc2c1c(-c1ccccc1)nn2CCN1CCOCC1]

Compound 28 was synthesised following similar procedures outlined in Example 31 (Compound 18), using 4-(2-hydrazinylethyl)morpholine instead of ethyl hydrazine in Step 3. As a slightly modified procedure, Step 3 was performed at 60° C. for 16 h. The reaction mixture was concentrated in vacuo and the crude residue was purified by column chromatography (silica gel, gradient 50 to 100% ethyl acetate/isohexane), followed by preparative HPLC, yielding Compound 28 as a solid.

LCMS (10 cm_ESCI_Formic) Rt 2.85 min; m/z 420 [M+H] 97.41% purity.

Example 35: 4-(4-chloro-1-methyl-5-phenyl-1H-pyrazolo[3,4-c]pyridazin-3-yl)benzonitrile (Compound 24)

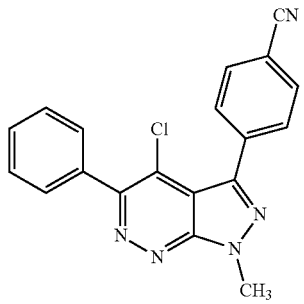 [SMILES: Cn1nc(-c2ccc(C#N)cc2)c2c(Cl)c(-c3ccccc3)nnc21]

A degassed mixture of 4-chloro-3-(4-iodophenyl)-1-methyl-5-phenyl-1H-pyrazolo[3,4-c]pyridazine (Compound 43, Example 23) (70 mg, 0.16 mmol), $Zn(CN)_2$ (18 mg, 0.094 mmol) and $Pd(PPh_3)_4$ (18 mg, 0.016 mmol) in DMF (1 mL) was heated at 100° C. for 40 min in a microwave. The reaction mixture was partitioned between ethyl acetate and water. The organic phase was washed with water and brine, dried using a phase separating cartridge and concentrated in vacuo. The crude residue was purified by column chromatography (silica gel, 10 to 20% ethyl acetate/isohexane), yielding Compound 24 as a solid (30 mg).

LCMS (10 cm_ESCI_Formic) Rt 4.4 min; m/z 346 [M+H] 96.24% purity.

Example 36: 3-(4-chloro-1-methyl-5-phenyl-1H-pyrazolo[3,4-c]pyridazin-3-yl)benzonitrile (Compound 34)

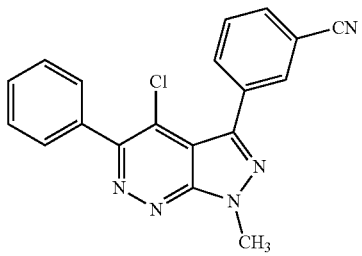 [SMILES: Cn1nc(-c2cccc(C#N)c2)c2c(Cl)c(-c3ccccc3)nnc21]

Compound 34 was synthesised following similar procedures outlined in Example 35 (Compound 24), using 4-chloro-3-(3-iodophenyl)-1-methyl-5-phenyl-1H-pyrazolo[3,4-c]pyridazine (Compound 3, Example 30) as the starting material instead of 4-chloro-3-(4-iodophenyl)-1-methyl-5-phenyl-1H-pyrazolo[3,4-c]pyridazine (Compound 43, Example 23).

LCMS (10 cm_ESCI_Formic) Rt 4.36 min; m/z 346 [M+H] 99.13% purity.

Example 37: 3-(3-(4-chloro-1-methyl-5-phenyl-1H-pyrazolo[3,4-c]pyridazin-3-yl)phenyl)prop-2-yn-1-ol (Compound 30)

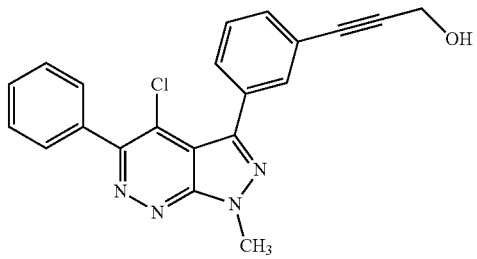 [SMILES: Cn1nc(-c2cccc(C#CCO)c2)c2c(Cl)c(-c3ccccc3)nnc21]

A mixture of 4-chloro-3-(3-iodophenyl)-1-methyl-5-phenyl-1H-pyrazolo [3,4-c]pyridazine (Compound 7, Example 32) (80 mg, 0.18 mmol), propargyl alcohol (41 mg, 0.74 mmol), triethylamine (87 µl, 0.63 mmol), CuI (3.5 mg, 0.018 mmol), triphenylphosphine (5 mg, 0.018 mmol) and Pd(PPh$_3$)$_4$ (20 mg, 0.018 mmol) in 1,4-dioxane (1.5 mL) was heated at 100° C. for 4 h in a sealed tube. The reaction mixture was partitioned between CH$_2$Cl$_2$ and water. The organic phase was separated and dried using a phase separating cartridge then concentrated in vacuo. The crude residue was purified by column chromatography (silica gel, 20-30% ethyl acetate/isohexane), yielding Compound 30 as a solid (26 mg).

LCMS (15 cm_Formic_ASCENTIS_HPLC) Rt 9.67 min; m/z 375 [M+H] 86.09% purity.

Example 38: N-(3-(2-(4-chloro-3,5-diphenyl-1H-pyrazolo[3,4-c]pyridazin-1-yl)acetamido)propyl)-5-((4S)-2-oxohexahydro-1H-thieno[3,4-d]imidazol-4-yl)pentanamide (Compound 44)

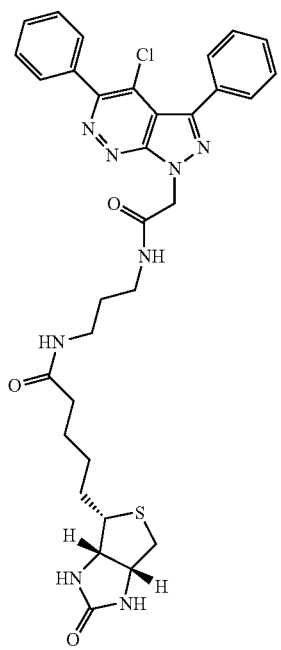 [SMILES: O=C(CCCC[C@@H]1SC[C@@H]2NC(=O)N[C@@H]21)NCCCNC(=O)Cn1nc(-c2ccccc2)c2c(Cl)c(-c3ccccc3)nnc21]

To a solution of N-(3-aminopropyl)-5-((3aS,4S,6aR)-2-oxohexahydro-1H-thieno[3,4-d]imidazol-4-yl)pentanamide (also known as N-(3-Aminopropyl)biotinamide trifluoroacetate, commercially available from Sigma-Aldrich or J&K Scientific Ltd) (0.22 mmol) in anhydrous DMF (1.1 mL) were sequentially added DIPEA (57 µL, 0.33 mmol), 2-(4-chloro-3,5-diphenyl-1H-pyrazolo[3,4-c]pyridazin-1-yl)acetic acid (80 mg, 0.22 mmol) and 2-(7-Aza-1H-benzotriazole-1-yl)-1,1,3,3-tetramethyluronium hexafluorophosphate (HATU, commercially available from Sigma-Aldrich or Novabiochem) (125 mg, 0.33 mmol). The reaction mixture was stirred at room temperature for 2 h, then diluted with ethyl acetate and washed with aqueous NaHCO$_3$ and 4% aqueous LiCl. The organic phase was then dried over MgSO$_4$, and evaporated under vacuum. The residue was purified by preparative HPLC yielding Compound 44 as a beige solid (34 mg).

LCMS (15 cm_Bicarb_GeminiNX_HPLC) Rt 9.26 min; m/z 647 [M+H] 90.15% purity.

Example 39: 2-(4-chloro-3,5-diphenyl-1H-pyrazolo[3,4-c]pyridazin-1-yl)-1-(pyrrolidin-1-yl)ethanone (Compound 45)

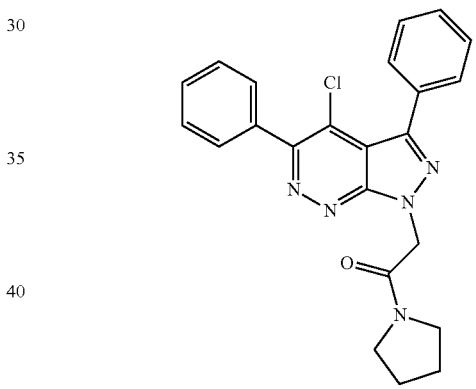

To a suspension of 2-(4-chloro-3,5-diphenyl-1H-pyrazolo[3,4-c]pyridazin-1-yl)acetic acid (510 mg, 1.4 mmol) in CH$_2$Cl$_2$ (9 mL) were added pyrrolidine (174 µL, 2.1 mmol), diisopropylethylamine (DIPEA) (366 µL, 2.1 mmol) and 2-(7-Aza-1H-benzotriazole-1-yl)-1,1,3,3-tetramethyluronium hexafluorophosphate (HATU) (798 mg, 2.1 mmol). The solution obtained was stirred at room temperature for 90 min then diluted with CH$_2$Cl$_2$. The organic phase was washed with aqueous NaHCO$_3$, passed over a phase separator and concentrated in vacuo. The resultant residue was purified using chromatography (silica gel, gradient 0 to 70% ethyl acetate/isohexane) followed by a second chromatography purification (silica gel, gradient 0 to 25% dichloromethane/ether) yielding Compound 45 as a solid (165 mg).

LCMS (10 cm_ESCI_Formic) Rt 4.27 min; m/z 418 [M+H] 99.92% purity.

Example 40: 2-(4-chloro-3,5-diphenyl-1H-pyrazolo[3,4-c]pyridazin-1-yl)acetic acid (Compound 47)

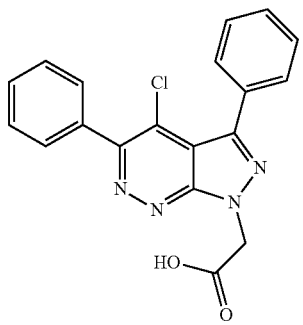 [SMILES: O=C(O)Cn1nc(-c2ccccc2)c2c(Cl)c(-c3ccccc3)nnc21]

A suspension of sodium 2-(5-amino-3-phenyl-4-(phenylethynyl)-1H-pyrazol-1-yl)acetate (2 g, 6.0 mmol) in diethylether (10 mL) and concentrated HCl (50 mL) was cooled at −15° C. before sodium nitrite (0.62 g, 8.0 mmol) in water (5 mL) was added dropwise. The solution was allowed to warm up to room temperature and left stirring for further 18 h. The reaction mixture was carefully quenched with an aqueous solution of $Na_2CO_3$ at 10° C., until pH basic, and then extracted EtOAc, backwashed with water then brine, dried ($MgSO_4$) and concentrated in vacuo. The resultant residue was purified using chromatography (silica gel, gradient 2 to 10% diethylether/$CH_2Cl_2$) yielding Compound 47 as a yellow foam (580 mg).

LCMS (10 cm_ESCI_Formic) Rt 3.73 min; m/z 365 [M+H] 94.82% purity

Example 41: 2-(4-chloro-3,5-diphenyl-1H-pyrazolo[3,4-c]pyridazin-1-yl)-1-morpholinoethanone (Compound 48)

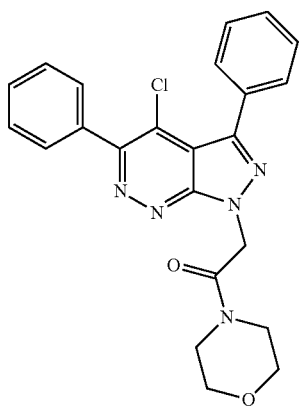 [SMILES: O=C(Cn1nc(-c2ccccc2)c2c(Cl)c(-c3ccccc3)nnc21)N1CCOCC1]

To a suspension of 2-(4-chloro-3,5-diphenyl-1H-pyrazolo[3,4-c]pyridazin-1-yl)acetic acid (60 mg, 0.16 mmol) in DMF (1 mL) were added morpholine (17 mg, 0.20 mmol) and 1-(3-dimethylaminopropyl)-3-ethylcarbodiimide hydrochloride (EDC. HCl) (38 mg, 0.20 mmol). The solution obtained was stirred at room temperature for 18 h then diluted with EtOAc. The organic phase was washed with water and brine, dried ($MgSO_4$) and concentrated in vacuo. The resultant residue was purified using chromatography (silica gel, ethyl acetate) yielding the Compound 48 as a solid (20 mg).

LCMS (10 cm_ESCI_Formic) Rt 3.67 min; m/z 434 [M+H] 95.17% purity.

Example 42: 2-(4-chloro-3,5-diphenyl-1H-pyrazolo[3,4-c]pyridazin-1-yl)-N-(cyanomethyl)-N-methylacetamide (Compound 49)

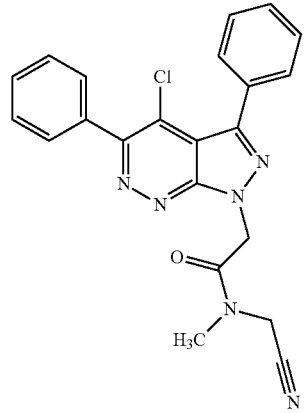 [SMILES: CN(CC#N)C(=O)Cn1nc(-c2ccccc2)c2c(Cl)c(-c3ccccc3)nnc21]

To a suspension of 2-(4-chloro-3,5-diphenyl-1H-pyrazolo[3,4-c]pyridazin-1-yl)acetic acid (60 mg, 0.16 mmol) in DMF (1 mL) were added N-methyl aminoacetonitrile (14 mg, 0.20 mmol) and 1,1'-carbonyldiimidazole hydrochloride (CDI. HCl) (38 mg, 0.20 mmol). The solution obtained was stirred at room temperature for 2 h then diluted with EtOAc. The organic phase was washed with water and brine, dried ($MgSO_4$) and concentrated in vacuo. The resultant residue was purified using chromatography (silica gel, gradient 1/1 ethyl acetate/isohexane) yielding Compound 49 as a solid (30 mg).

LCMS (10 cm_ESCI_Formic) Rt 4.17 min; m/z 417 [M+H] 94.82% purity.

Example 43: 2-(4-chloro-3,5-diphenyl-1H-pyrazolo[3,4-c]pyridazin-1-yl)-N-(2-morpholinoethyl)acetamide (Compound 50)

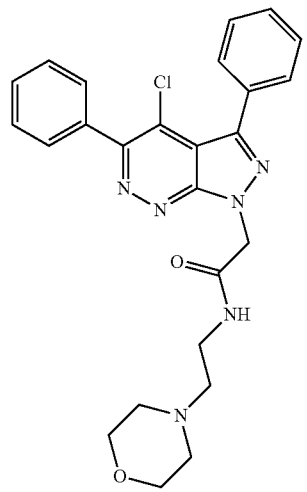 [SMILES: O=C(Cn1nc(-c2ccccc2)c2c(Cl)c(-c3ccccc3)nnc21)NCCN1CCOCC1]

To a suspension of 2-(4-chloro-3,5-diphenyl-1H-pyrazolo[3,4-c]pyridazin-1-yl)acetic acid (60 mg, 0.16 mmol) in DMF (1 mL) were added 4-(2-aminoethyl)morpholine (32 mg, 0.25 mmol) and 1-(3-dimethylaminopropyl)-3-ethylcarbodiimide hydrochloride (EDC.HCl) (38 mg, 0.20 mmol). The solution obtained was stirred at room temperature for 18 h then diluted with EtOAc. The organic phase was washed with water and brine, dried (MgSO$_4$) and concentrated in vacuo. The resultant residue was purified using chromatography (silica gel, gradient 10% MeOH/ethyl acetate) yielding Compound 50 as a solid (10 mg).

LCMS (10 cm_ESCI_Formic) Rt 3.64 min; m/z 477 [M+H] 95.28% purity.

Example 44: 2-(4-chloro-3,5-diphenyl-1H-pyrazolo [3,4-c]pyridazin-1-yl)-N-methyl-N-(1-methylpiperidin-4-yl)acetamide (Compound 51)

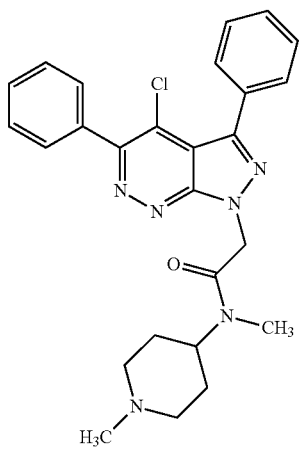 [SMILES: CN1CCC(N(C)C(=O)Cn2nc(-c3ccccc3)c3c(Cl)c(-c4ccccc4)nnc32)CC1]

To a suspension of 2-(4-chloro-3,5-diphenyl-1H-pyrazolo [3,4-c]pyridazin-1-yl)acetic acid (60 mg, 0.16 mmol) in DMF (1 mL) were added 1-methyl-4-(methylamino)piperidine (23 mg, 0.18 mmol), diisopropylethylamine (DIPEA) (63 µL, 0.36 mmol) and 2-(7-aza-1H-benzotriazole-1-yl)-1,1,3,3-tetramethyluronium hexafluorophosphate (HATU) (75 mg, 0.20 mmol). The solution obtained was stirred at room temperature for 1 hr then diluted with EtOAc. The organic phase was washed with water and brine, dried (MgSO$_4$) and concentrated in vacuo. The resultant residue was purified using chromatography (silica gel, gradient 1% Et$_3$N in 10-20% MeOH/ethyl acetate) yielding Compound 51 as a solid (2 mg).

LCMS (15 cm_Formic_ASCENTIS_HPLC) Rt 7.79 min; m/z 475 [M+H] 94.53% purity.

Example 45: 2-(4-chloro-3,5-diphenyl-1H-pyrazolo [3,4-c]pyridazin-1-yl)-1-(4-(methylsulfonyl)piperazin-1-yl)ethanone (Compound 52)

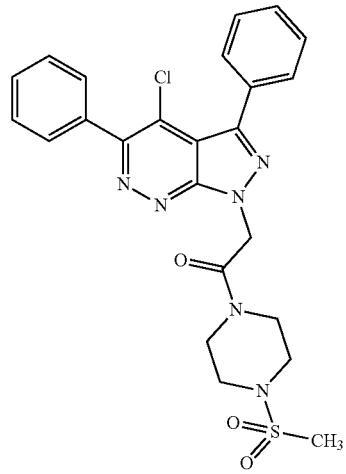 [SMILES: CS(=O)(=O)N1CCN(C(=O)Cn2nc(-c3ccccc3)c3c(Cl)c(-c4ccccc4)nnc32)CC1]

To a suspension of 2-(4-chloro-3,5-diphenyl-1H-pyrazolo [3,4-c]pyridazin-1-yl)acetic acid (56 mg, 0.15 mmol) in DMF (1 mL) were added 1-(methylsulfonyl)piperazine (28 mg, 0.17 mmol), diisopropylethylamine (DIPEA) (59 µL, 0.34 mmol) and 2-(7-aza-1H-benzotriazole-1-yl)-1,1,3,3-tetramethyluronium hexafluorophosphate (HATU) (70 mg, 0.18 mmol). The solution obtained was stirred at room temperature for 18 h then diluted with EtOAc. The organic phase was washed with water and brine, dried (MgSO$_4$) and concentrated in vacuo. The resultant residue was purified using chromatography (silica gel, gradient 20-40% ethyl acetate/isohexane) followed by a second chromatography purification (silica gel, gradient 10% ether/CH$_2$Cl$_2$) yielding Compound 52 as a solid (11 mg).

LCMS (15 cm_Bicarb_GeminiNX_HPLC) Rt 10.35 min; m/z 511 [M+H] 92.47% purity.

Example 46: 2-(4-chloro-3,5-diphenyl-1H-pyrazolo [3,4-c]pyridazin-1-yl)-N-(2-(dimethylamino)ethyl)-N-methylacetamide (Compound 53)

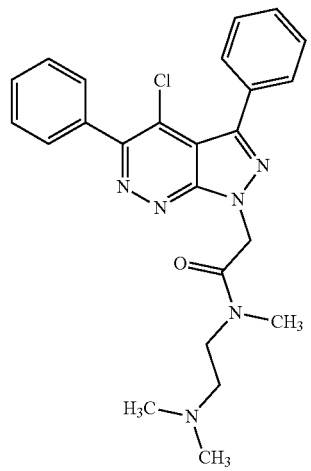 [SMILES: CN(C)CCN(C)C(=O)Cn1nc(-c2ccccc2)c2c(Cl)c(-c3ccccc3)nnc21]

To a suspension of 2-(4-chloro-3,5-diphenyl-1H-pyrazolo[3,4-c]pyridazin-1-yl)acetic acid (56 mg, 0.15 mmol) in DMF (1 mL) were added $N^1,N^1,N^2$-trimethylethane-1,2-diamine (17 mg, 0.17 mmol), diisopropylethylamine (DIPEA) (59 µL, 0.34 mmol) and 2-(7-aza-1H-benzotriazole-1-yl)-1,1,3,3-tetramethyluronium hexafluorophosphate (HATU) (70 mg, 0.18 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 53 as a solid (11 mg).

LCMS (10 cm_ESCI_Bicarb) Rt 3.35 min; m/z 449 [M+H] 95.56% purity.

Example 47: 2-(4-chloro-3,5-diphenyl-1H-pyrazolo[3,4-c]pyridazin-1-yl)-1,1-dioxido-4-thiomorpholinoethanone (Compound 54)

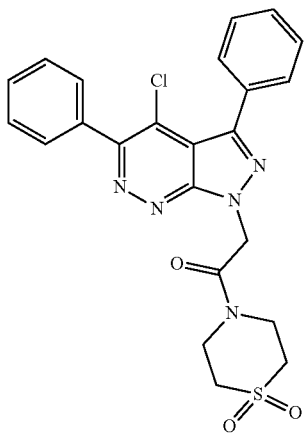 [SMILES: O=C(Cn1nc(-c2ccccc2)c2c(Cl)c(-c3ccccc3)nnc21)N1CCS(=O)(=O)CC1]

To a suspension of 2-(4-chloro-3,5-diphenyl-1H-pyrazolo[3,4-c]pyridazin-1-yl)acetic acid (100 mg, 0.27 mmol) in DMF (2 mL) were added thiomorpholine 1,1-dioxide (40 mg, 0.30 mmol), diisopropylethylamine (DIPEA) (105 µL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC followed by a second chromatography purification (silica gel, gradient 1/1 ethyl acetate/isohexane) yielding Compound 54 as a solid (33 mg).

LCMS (10 cm_Formic_ACE 3 C18 AR_HPLC) Rt 11.54 min; m/z 482 [M+H] 90.61% purity.

Example 48: 2-(4-chloro-3,5-diphenyl-1H-pyrazolo[3,4-c]pyridazin-1-yl)-1-(4-hydroxypiperidin-1-yl)ethanone (Compound 55)

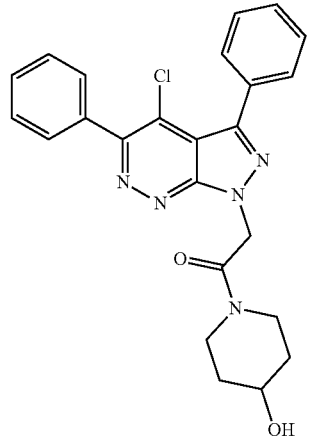 [SMILES: O=C(Cn1nc(-c2ccccc2)c2c(Cl)c(-c3ccccc3)nnc21)N1CCC(O)CC1]

To a suspension of 2-(4-chloro-3,5-diphenyl-1H-pyrazolo[3,4-c]pyridazin-1-yl)acetic acid (100 mg, 0.27 mmol) in DMF (2 mL) were added piperidin-4-ol (30 mg, 0.30 mmol), diisopropylethylamine (DIPEA) (105 µL, 0.60 mmol) and 2-(7-aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC followed by a second chromatography purification (silica gel, gradient 1/1 ethyl acetate/isohexane) yielding Compound 55 as a solid (10 mg).

LCMS (15 cm_Bicarb_GeminiNX_HPLC) Rt 9.83 min; m/z 448 [M+H] 95.96% purity.

Example 49: 2-(4-chloro-3,5-diphenyl-1H-pyrazolo[3,4-c]pyridazin-1-yl)-1-(4-(2,2,2-trifluoroethyl)piperazin-1-yl)ethanone (Compound 56)

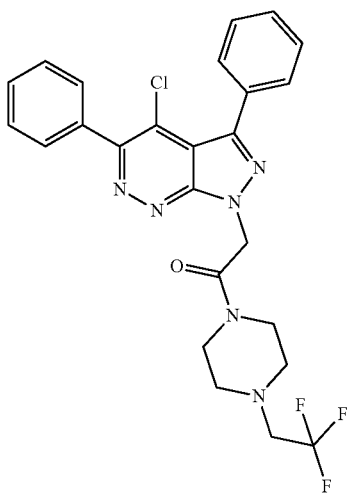 [SMILES: O=C(Cn1nc(-c2ccccc2)c2c(Cl)c(-c3ccccc3)nnc21)N1CCN(CC(F)(F)F)CC1]

To a suspension of 2-(4-chloro-3,5-diphenyl-1H-pyrazolo[3,4-c]pyridazin-1-yl)acetic acid (100 mg, 0.27 mmol) in DMF (2 mL) were added 1-(2,2,2-trifluoroethyl)piperazine (50 mg, 0.30 mmol), diisopropylethylamine (DIPEA) (105 µL, 0.60 mmol) and 2-(7-aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 56 as a solid (41 mg).

LCMS (15 cm_Bicarb_GeminiNX_HPLC) Rt 10.93 min; m/z 515 [M+H] 93.62% purity.

Example 50: 2-(4-chloro-3,5-diphenyl-1H-pyrazolo[3,4-c]pyridazin-1-yl)-N-(pyridin-3-ylmethyl)acetamide (Compound 57)

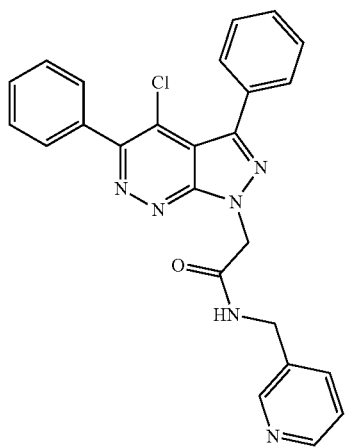 [SMILES: O=C(Cn1nc(-c2ccccc2)c2c(Cl)c(-c3ccccc3)nnc21)NCc1cccnc1]

To a suspension of 2-(4-chloro-3,5-diphenyl-1H-pyrazolo[3,4-c]pyridazin-1-yl)acetic acid (100 mg, 0.27 mmol) in DMF (2 mL) were added pyridin-3-ylmethanamine (33 mg, 0.30 mmol), diisopropylethylamine (DIPEA) (105 µL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 57 as a solid (37 mg).

LCMS (10 cm_ESCI_Formic) Rt 3.24 min; m/z 455 [M+H] 99.50% purity.

Example 51: 1-(2-(4-chloro-3,5-diphenyl-1H-pyrazolo[3,4-c]pyridazin-1-yl)acetoyl)piperidine-3-carbonitrile (Compound 58)

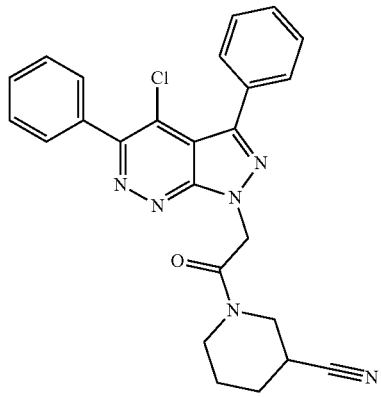 [SMILES: N#CC1CCCN(C(=O)Cn2nc(-c3ccccc3)c3c(Cl)c(-c4ccccc4)nnc32)C1]

To a suspension of 2-(4-chloro-3,5-diphenyl-1H-pyrazolo[3,4-c]pyridazin-1-yl)acetic acid (100 mg, 0.27 mmol) in DMF (2 mL) were added piperidine-3-carbonitrile (33 mg, 0.30 mmol), diisopropylethylamine (DIPEA) (105 µL, 0.60 mmol) and 2-(7-aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC followed by a second chromatography purification (silica gel, gradient 1/1 ethyl acetate/isohexane) yielding Compound 58 as a solid (28 mg).

LCMS (10 cm_Formic_ACE 3 C18 AR_HPLC) Rt 12.04 min; m/z 457 [M+H] 97.93% purity.

Example 52: 2-(4-chloro-3,5-diphenyl-1H-pyrazolo[3,4-c]pyridazin-1-yl)-1-(4-(dimethylamino)piperidin-1-yl)ethanone (Compound 59)

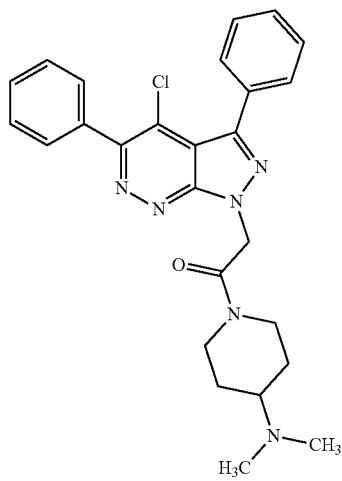 [SMILES: CN(C)C1CCN(C(=O)Cn2nc(-c3ccccc3)c3c(Cl)c(-c4ccccc4)nnc32)CC1]

To a suspension of 2-(4-chloro-3,5-diphenyl-1H-pyrazolo[3,4-c]pyridazin-1-yl)acetic acid (100 mg, 0.27 mmol) in DMF (2 mL) were added N,N-dimethylpiperidin-4-amine (40 mg, 0.30 mmol), diisopropylethylamine (DIPEA) (105 μL, 0.60 mmol) and 2-(7-aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 59 as a solid (10 mg).

LCMS (15 cm_Formic_ASCENTIS_HPLC) Rt 7.99 min; m/z 475 [M+H] 91.14% purity.

Example 53: 2-(4-chloro-3,5-diphenyl-1H-pyrazolo[3,4-c]pyridazin-1-yl)-N-(1-methylpiperidin-4-yl)acetamide (Compound 60)

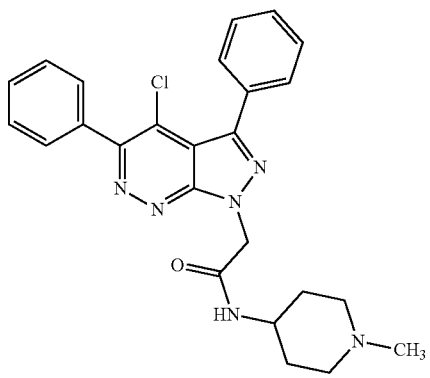 [SMILES: CN1CCC(NC(=O)Cn2nc(-c3ccccc3)c3c(Cl)c(-c4ccccc4)nnc32)CC1]

To a suspension of 2-(4-chloro-3,5-diphenyl-1H-pyrazolo[3,4-c]pyridazin-1-yl)acetic acid (100 mg, 0.27 mmol) in DMF (2 mL) were added 1-methylpiperidin-4-amine (35 mg, 0.30 mmol), diisopropylethylamine (DIPEA) (105 μL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 60 as a solid (22 mg).

LCMS (15 cm_Formic_ASCENTIS_HPLC) Rt 7.90 min; m/z 461 [M+H] 94.77% purity.

Example 54: 2-(4-chloro-3,5-diphenyl-1H-pyrazolo[3,4-c]pyridazin-1-yl)-N-(1-methylcyclobutyl)acetamide (Compound 61)

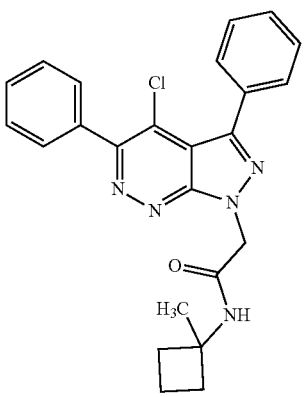 [SMILES: CC1(NC(=O)Cn2nc(-c3ccccc3)c3c(Cl)c(-c4ccccc4)nnc32)CCC1]

To a suspension of 2-(4-chloro-3,5-diphenyl-1H-pyrazolo[3,4-c]pyridazin-1-yl)acetic acid (100 mg, 0.27 mmol) in DMF (2 mL) were added 1-methyl-cyclobutyl amine hydrochloride (37 mg, 0.30 mmol), diisopropylethylamine (DIPEA) (150 μL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 2 h then diluted with EtOAc. The organic phase was washed with water and brine, dried (MgSO$_4$) and concentrated in vacuo. The resultant residue was purified by chromatography purification (silica gel, gradient 10-20% ethyl acetate/isohexane) yielding Compound 61 as a solid (22 mg).

LCMS (15 cm_Bicarb_GeminiNX_HPLC) Rt 10.96 min; m/z 432 [M+H] 96.73% purity.

Example 55: 2-(4-chloro-3,5-diphenyl-1H-pyrazolo[3,4-c]pyridazin-1-yl)-1-(3,3-difluoropyrrolidin-1-yl)ethanone (Compound 62)

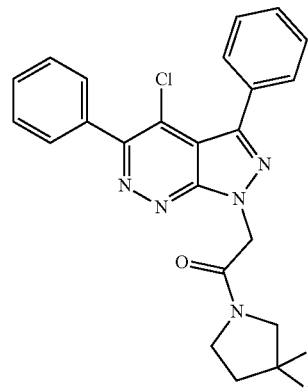

To a suspension of 2-(4-chloro-3,5-diphenyl-1H-pyrazolo[3,4-c]pyridazin-1-yl)acetic acid (100 mg, 0.27 mmol) in DMF (2 mL) were added 3,3-difluoropyrrolidine hydrochloride (43 mg, 0.30 mmol), diisopropylethylamine (DIPEA) (150 μL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 2 h then diluted with EtOAc. The organic phase was washed with water and brine, dried (MgSO$_4$) and concentrated in vacuo. The resultant residue was purified by chromatography purification (silica gel, gradient 10-20% ethyl acetate/isohexane) yielding Compound 62 as a solid (18 mg).

LCMS (15 cm_Bicarb_GeminiNX_HPLC) Rt 10.72 min; m/z 454 [M+H] 93.08% purity.

Example 56: 2-(4-chloro-3,5-diphenyl-1H-pyrazolo[3,4-c]pyridazin-1-yl)-1-((1R,4R)-5-methyl-2,5-diazabicyclo[2.2.1]heptan-2-yl)ethanone (Compound 63)

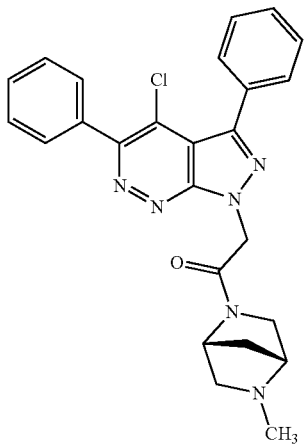 [SMILES: CN1C[C@H]2C[C@@H]1CN2C(=O)Cn1nc(-c2ccccc2)c2c(Cl)c(-c3ccccc3)nnc21]

To a suspension of 2-(4-chloro-3,5-diphenyl-1H-pyrazolo[3,4-c]pyridazin-1-yl)acetic acid (100 mg, 0.27 mmol) in DMF (2 mL) were added (1R,4R)-2-methyl-2,5-diazabicyclo[2.2.1]heptane (26 mg, 0.30 mmol), diisopropylethylamine (DIPEA) (105 μL, 0.60 mmol) and 2-(7-Aza-1H-benzotriazole-1-yl)-1,1,3,3-tetramethyluronium hexafluorophosphate (HATU) (125 mg, 0.33 mmol). The solution obtained was stirred at room temperature for 18 h then diluted with EtOAc. The organic phase was washed with water and brine, dried (MgSO$_4$) and concentrated in vacuo. The resultant residue was purified by preparative HPLC yielding Compound 63 as a solid (11 mg).

LCMS (15 cm_Formic_ASCENTIS_HPLC) Rt 7.82 min; m/z 459 [M+H] 94.39% purity.

Example 57: 2-(4-chloro-3,5-diphenyl-1H-pyrazolo[3,4-c]pyridazin-1-yl)acetamide (Compound 64)

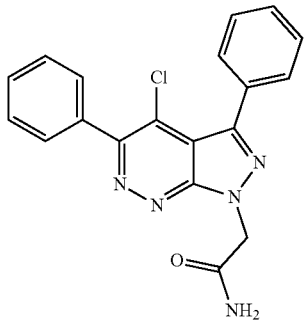 [SMILES: NC(=O)Cn1nc(-c2ccccc2)c2c(Cl)c(-c3ccccc3)nnc21]

To a solution of 2-(4-chloro-3,5-diphenyl-1H-pyrazolo[3,4-c]pyridazin-1-yl)acetic acid (160 mg, 0.44 mmol) in CH$_2$Cl$_2$ (6 mL) was added oxalyl chloride (55 μl, 0.66 mmol). The solution obtained was stirred at room temperature for 1 h. The reaction mixture was concentrated in vacuo. The residue was dissolved in CH$_2$Cl$_2$ (6 mL) and a solution (7 N) of ammonia in methanol was added dropwise (125 μl, 0.8 mmol). The reaction mixture was stirred for 1 h, then concentrated in vacuo. The resultant residue was purified by preparative HPLC yielding Compound 64 as a solid (32 mg).

LCMS (10 cm_ESCI_Bicarb_MeCN) Rt 3.62 min; m/z 364 [M+H] 99.1% purity.

Example 58: 2-(4-chloro-3,5-diphenyl-1H-pyrazolo[3,4-c]pyridazin-1-yl)-1-(4-methyl-1,4-diazepan-1-yl)ethanone (Compound 65)

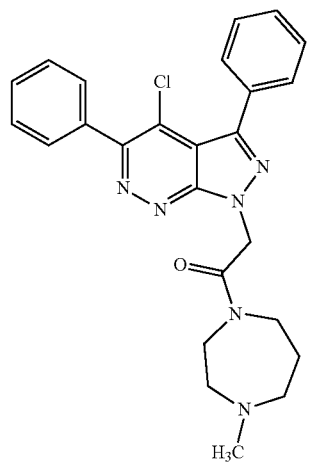 [SMILES: CN1CCCN(C(=O)Cn2nc(-c3ccccc3)c3c(Cl)c(-c4ccccc4)nnc32)CC1]

A solution of diisopropylethylamine (DIPEA) (120 μL, 0.67 mmol) and 1-methyl 1,4-diazepane (34 mg, 0.3 mmol) in CH$_2$Cl$_2$ (1 mL) was added to a mixture of 2-(4-chloro-3,5-diphenyl-1H-pyrazolo[3,4-c]pyridazin-1-yl)acetic acid (100 mg, 0.27 mmol), N-(3-Dimethylaminopropyl)-N'-ethylcarbodiimide hydrochloride(EDC) (60 mg, 0.3 mmol) and 2-hydroxypyridine-N-oxide (HOPO) (30 mg, 0.27 mmol). The solution obtained was stirred at room temperature for 18 h. The reaction was purified using chromatography (silica gel, gradient 0 to 5% triethylamine/acetone) followed by preparative HPLC yielding Compound 65 as a white solid (25 mg).

LCMS (10 cm_ESCI_Formic) Rt 2.73 min; m/z 461 [M+H] 99.86% purity.

Example 59: 1-(4-acetoylpiperazin-1-yl)-2-(4-chloro-3,5-diphenyl-1H-pyrazolo[3,4-c]pyridazin-1-yl)ethanone (Compound 66)

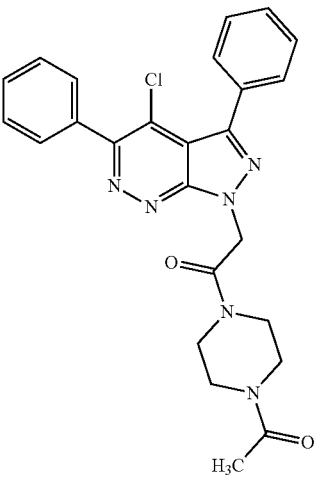 [SMILES: CC(=O)N1CCN(C(=O)Cn2nc(-c3ccccc3)c3c(Cl)c(-c4ccccc4)nnc32)CC1]

A solution of diisopropylethylamine (DIPEA) (120 µL, 0.67 mmol) and 1-acetylpiperazine (38 mg, 0.3 mmol) in CH$_2$Cl$_2$ (1 mL) was added to a mixture of 2-(4-chloro-3,5-diphenyl-1H-pyrazolo[3,4-c]pyridazin-1-yl)acetic acid (100 mg, 0.27 mmol), N-(3-dimethylaminopropyl)-N-ethylcarbodiimide hydrochloride(EDC) (60 mg, 0.3 mmol) and 2-hydroxypyridine-N-oxide (HOPO) (30 mg, 0.27 mmol). The solution obtained was stirred at room temperature for 18 h then 1-acetylpiperazine (10 mg, 0.08 mmol) and N-(3-dimethylaminopropyl)-N'-ethylcarbodiimide hydrochloride (EDC) (30 mg, 0.15 mmol) were added. After a further 3.5 h the reaction was purified using chromatography (silica gel, gradient 0 to 5% triethylamine/acetone) followed by preparative HPLC yielding Compound 66 as a white solid (32.2 mg).

LCMS (10 cm_ESCI_Formic) Rt 3.67 min; m/z 475 [M+H] 99.58% purity.

Example 60: 2-(4-chloro-3,5-diphenyl-1H-pyrazolo[3,4-c]pyridazin-1-yl)-1-(3-(dimethylamino)pyrrolidin-1-yl)ethanone (Compound 67)

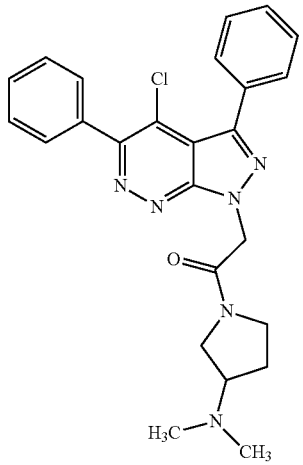 [SMILES: CN(C)C1CCN(C(=O)Cn2nc(-c3ccccc3)c3c(Cl)c(-c4ccccc4)nnc32)C1]

A solution of diisopropylethylamine (DIPEA) (120 µL, 0.67 mmol) and N,N-dimethylpyrrolidine (34 mg, 0.3 mmol) in CH$_2$Cl$_2$ (1 mL) was added to a mixture of 2-(4-chloro-3,5-diphenyl-1H-pyrazolo[3,4-c]pyridazin-1-yl)acetic acid (100 mg, 0.27 mmol), N-(3-dimethylaminopropyl)-N'-ethylcarbodiimide hydrochloride(EDC) (60 mg, 0.3 mmol) and 2-hydroxypyridine-N-oxide (HOPO) (30 mg, 0.27 mmol). The solution obtained was stirred at room temperature for 18 h then N,N-dimethylpyrrolidine (10 mg, 0.09 mmol) and N-(3-dimethylaminopropyl)-N'-ethylcarbodiimide hydrochloride(EDC) (30 mg, 0.15 mmol) were added. After a further 3.5 h the reaction was purified using chromatography (silica gel, gradient 0 to 5% triethylamine/acetone) followed by preparative HPLC yielding Compound 67 as a white solid (27.3 mg).

LCMS (10 cm_ESCI_Formic) Rt 2.73 min; m/z 461 [M+H] 99.54% purity.

Example 61: 2-(4-chloro-3,5-diphenyl-1H-pyrazolo[3,4-c]pyridazin-1-yl)-N-(3-(dimethylamino)propyl)acetamide (Compound 68)

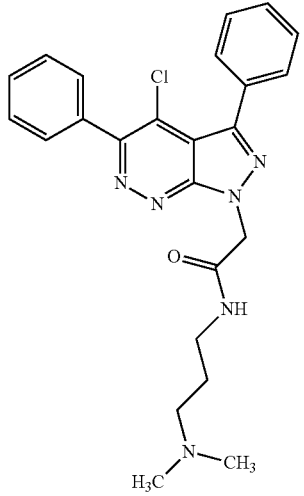 [SMILES: CN(C)CCCNC(=O)Cn1nc(-c2ccccc2)c2c(Cl)c(-c3ccccc3)nnc21]

Example 61 was synthesised following a similar procedure outlined in Example 58, using 3-dimethylaminopropylamine instead of 1-methyl 1,4-diazepane. Compound 68 was obtained as a colourless solid (16 mg).

LCMS (10 cm_ESCI_Formic) Rt 2.68 min; m/z 449 [M+H] 97.9% purity.

Example 62: 4-(2-(4-chloro-3,5-diphenyl-1H-pyrazolo[3,4-c]pyridazin-1-yl)acetoyl)piperazin-2-one (Compound 69)

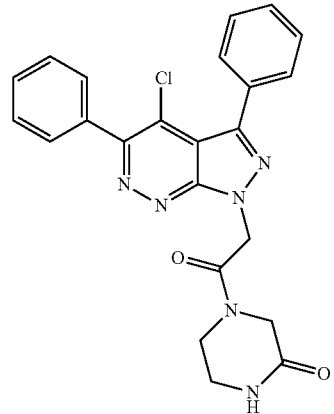 [SMILES: O=C1CN(C(=O)Cn2nc(-c3ccccc3)c3c(Cl)c(-c4ccccc4)nnc32)CCN1]

To a suspension of 2-(4-chloro-3,5-diphenyl-1H-pyrazolo[3,4-c]pyridazin-1-yl)acetic acid (111 mg, 0.3 mmol) in CH$_2$Cl$_2$ (2 mL) were added 2-oxopiperazine (33 mg, 0.33 mmol), diisopropylethylamine (DIPEA) (80 µL, 0.45 mmol) and 2-(7-aza-1H-benzotriazole-1-yl)-1,1,3,3-tetramethyluronium hexafluorophosphate (HATU) (130 mg, 0.33 mmol). The solution obtained was stirred at room temperature for 2 h then diluted with CH$_2$Cl$_2$. The organic phase was washed with aqueous water, dried over MgSO$_4$, filtered and concentrated in vacuo. The resultant residue was purified using chromatography (silica gel, gradient 20 to 100% ethyl acetate/isohexane, then 0 to 100% ethyl acetate/acetone) followed by preparative HPLC yielding Compound 69 as a brown solid (69.7 mg).

LCMS (10 cm_ESCI_Bicarb) Rt 3.52 min; m/z 447 [M+H] 98.17% purity.

Example 63: 2-(4-chloro-3,5-diphenyl-1H-pyrazolo[3,4-c]pyridazin-1-yl)-1-(3-hydroxypyrrolidin-1-yl)ethanone (Compound 70)

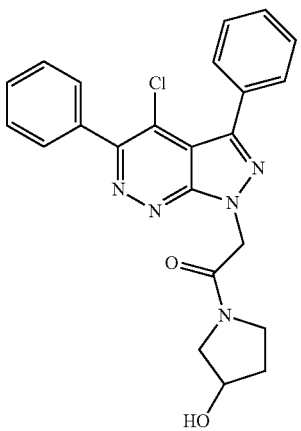 [SMILES: O=C(Cn1nc(-c2ccccc2)c2c(Cl)c(-c3ccccc3)nnc21)N1CCC(O)C1]

Example 63 was synthesised following a similar procedure outlined in Example 62, using 3-hydroxypyrrolidine instead of 2-oxopiperazine. Compound 70 was obtained as a white solid (46 mg).

LCMS (10 cm_ESCI_Formic) Rt 3.73 min; m/z 434 [M+H] 99.79% purity.

Example 64: 2-(4-chloro-3,5-diphenyl-1H-pyrazolo[3,4-c]pyridazin-1-yl)-N-(2-hydroxyethyl)acetamide (Compound 71)

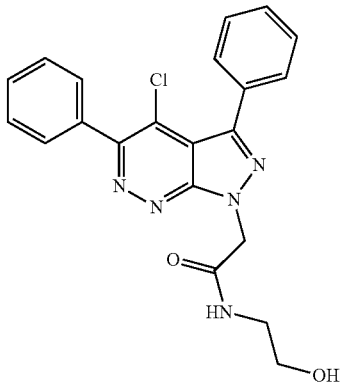 [SMILES: O=C(Cn1nc(-c2ccccc2)c2c(Cl)c(-c3ccccc3)nnc21)NCCO]

Example 64 was synthesised following a similar procedure outlined in Example 62, using ethanolamine instead of 2-oxopiperazine. Compound 71 was obtained as a white solid (13 mg).

LCMS (10 cm_ESCI_Bicarb_MeCN) Rt 3.50 min; m/z 408 [M+H] 99.78% purity.

Example 65: (S)-2-(4-chloro-3,5-diphenyl-1H-pyrazolo[3,4-c]pyridazin-1-yl)-N-(2-hydroxypropyl)acetamide (Compound 72)

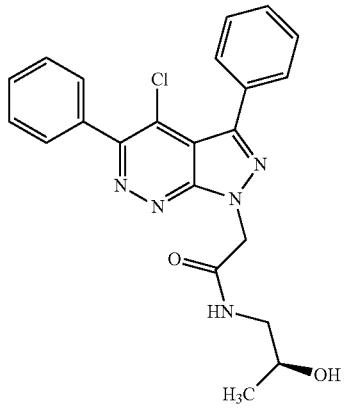 [SMILES: C[C@H](O)CNC(=O)Cn1nc(-c2ccccc2)c2c(Cl)c(-c3ccccc3)nnc21]

Example 65 was synthesised following a similar procedure outlined in Example 62, using (S)-1-amino-2-propanol instead of 2-oxopiperazine. Compound 72 was obtained as a white solid (29 mg).

LCMS (10 cm_ESCI_Bicarb_MeCN) Rt 3.58 min; m/z 422 [M+H] 98.12% purity.

Example 66: 2-(4-chloro-3,5-di phenyl-1H-pyrazolo[3,4-c] pyridazin-1-yl)-N-(2-methoxyethyl)acetamide (Compound 73)

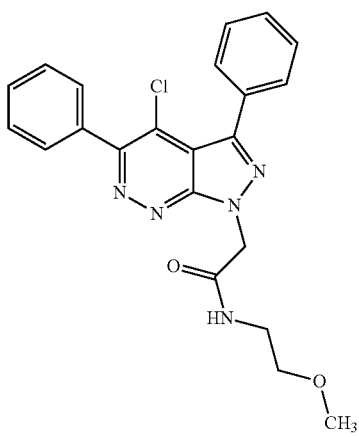 [SMILES: COCCNC(=O)Cn1nc(-c2ccccc2)c2c(Cl)c(-c3ccccc3)nnc21]

Example 66 was synthesised following a similar procedure outlined in Example 62, using methoxyethylamine instead of 2-oxopiperazine. Compound 73 was obtained as a white solid (25.7 mg).

LCMS (10 cm_ESCI_Formic_MeCN) Rt 4.05 min; m/z 422 [M+H] 99.65% purity.

121

Example 67: (R)-2-(4-chloro-3,5-diphenyl-1H-pyrazolo[3,4-c]pyridazin-1-yl)-N-(2-hydroxypropyl)acetamide (Compound 74)

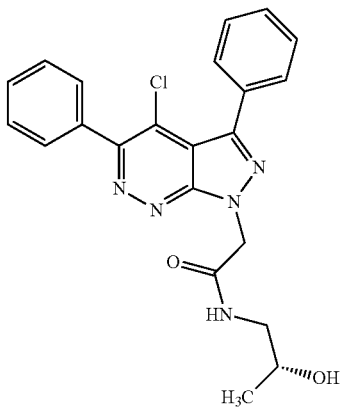 [SMILES: C[C@@H](O)CNC(=O)Cn1nc(-c2ccccc2)c2c(Cl)c(-c3ccccc3)nnc21]

Example 67 was synthesised following a similar procedure outlined in Example 62, using (R)-1-amino-2-propanol instead of 2-oxopiperazine. Compound 74 was obtained as a white solid (37 mg).

LCMS (10 cm_ESCI_Bicarb_MeCN) Rt 3.14 min; m/z 422 [M+H] 99.7% purity.

Example 68: 2-(4-chloro-3-(4-fluorophenyl)-5-phenyl-1H-pyrazolo[3,4-c]pyridazin-1-yl)-1-morpholinoethanone (Compound 75)

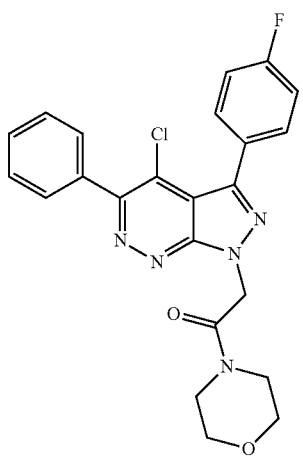 [SMILES: O=C(Cn1nc(-c2ccc(F)cc2)c2c(Cl)c(-c3ccccc3)nnc21)N1CCOCC1]

122

Step 1: ethyl 2-(5-amino-3-(4-fluorophenyl)-1H-pyrazol-1-yl)acetate

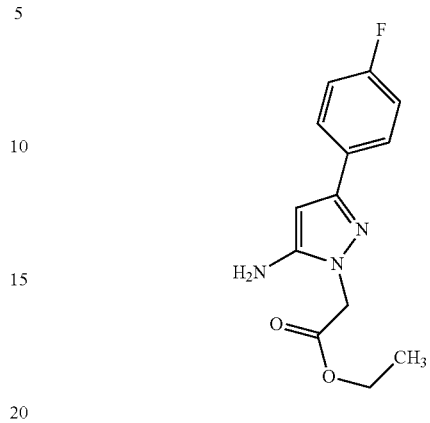

A mixture of 4-fluorobenzoylacetonitrile (5 g, 30.7 mmol) and ethyl hydrazinoacetate hydrochloride (4.74 g, 30.7 mmol) in ethanol (50 mL) was heated to reflux for 2 h. The reaction mixture was concentrated in vacuo. The crude reaction mixture was partitioned between $CH_2Cl_2$ and concentrated aqueous ammonia. The aqueous phase was extracted with $CH_2Cl_2$ and the organic phases combined, dried over $MgSO_4$, filtered and evaporated to give ethyl 2-(5-amino-3-(4-fluorophenyl)-1H-pyrazol-1-yl)acetate as a solid (7.4 g), which was used as such in the subsequent step.

Step 2: ethyl 2-(5-acetamido-3-(4-fluorophenyl)-1H-pyrazol-1-yl)acetate

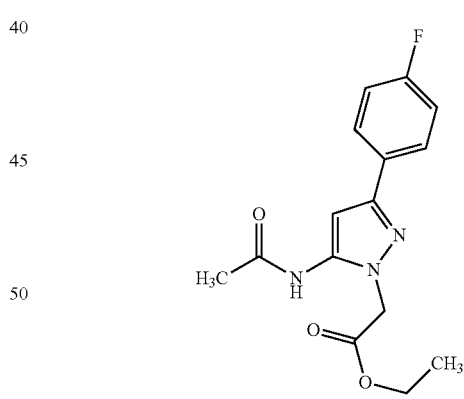

To a solution of ethyl 2-(5-amino-3-(4-fluorophenyl)-1H-pyrazol-1-yl)acetate (6.91 g, 26.3 mmol) in pyridine (62 mL) was added acetic anhydride (3 ml, 31.5 mmol). The reaction was stirred at room temperature for 16 h. Ethanol was added and the mixture was concentrated in vacuo. The crude residue was purified by column chromatography (silica gel, gradient 10 to 100% ethyl acetate/isohexane) yielding ethyl 2-(5-acetamido-3-(4-fluorophenyl)-1H-pyrazol-1-yl)acetate as a solid (7.6 g).

Step 3: ethyl 2-(5-acetamido-3-(4-fluorophenyl)-4-iodo-1H-pyrazol-1-yl)acetate

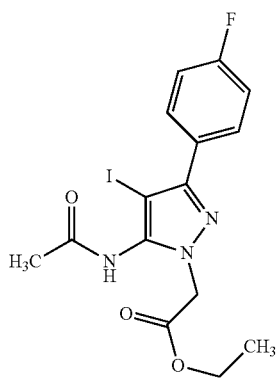 [SMILES: CCOC(=O)Cn1nc(-c2ccc(F)cc2)c(I)c1NC(C)=O]

To a solution of ethyl 2-(5-acetamido-3-(4-fluorophenyl)-1H-pyrazol-1-yl)acetate (1.1 g, 3.7 mmol) in ethanol (33 mL) were added iodic acid (170 mg, 0.95 mmol) and iodine (480 mg, 1.9 mmol). The reaction was stirred for 90 min at 60° C. The reaction mixture was concentrated in vacuo and the residue was dissolved in $CH_2Cl_2$ and washed with a 2 N $Na_2SO_3$ solution. The organic phase was dried over $MgSO_4$, filtered and evaporated to give ethyl 2-(5-acetamido-3-(4-fluorophenyl)-4-iodo-1H-pyrazol-1-yl)acetate as a white solid (1.63 g), which was used as such in the subsequent step.

Step 4: ethyl 2-(5-acetamido-3-(4-fluorophenyl)-4-(phenylethynyl)-1H-pyrazol-1-yl)acetate

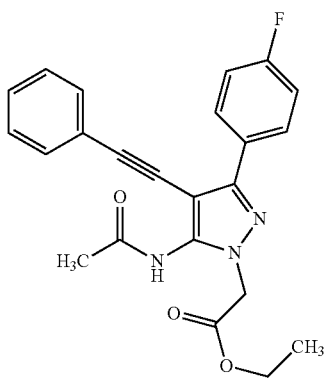 [SMILES: CCOC(=O)Cn1nc(-c2ccc(F)cc2)c(C#Cc2ccccc2)c1NC(C)=O]

A degassed solution of phenylacetylene (290 mg, 2.8 mmol) and $Et_3N$ (11 mL) in DMF (4 mL) was added to ethyl 2-(5-acetamido-3-(4-fluorophenyl)-4-(phenylethynyl)-1H-pyrazol-1-yl)acetate (1.0 g, 2.3 mmol), CuI (90 mg, 0.46 mmol) and $PdCl_2(PPh_3)_2$ (160 mg, 0.23 mmol) under an atmosphere of $N_2$. The reaction was then heated to 85° C. for 5 h. The reaction mixture was concentrated in vacuo and the residue was purified by column chromatography (silica gel, gradient 10 to 100% ethyl acetate/isohexane) yielding ethyl 2-(5-acetamido-3-(4-fluorophenyl)-4-(phenylethynyl)-1H-pyrazol-1-yl)acetate as a tan solid (620 mg).

Step 5: 2-(5-amino-3-(4-fluorophenyl)-4-(phenylethynyl)-1H-pyrazol-1-yl)acetic acid

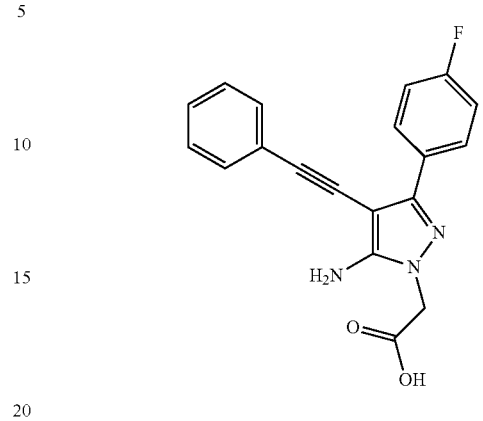

A solution of ethyl 2-(5-acetamido-3-(4-fluorophenyl)-4-(phenylethynyl)-1H-pyrazol-1-yl)acetate (620 mg, 1.5 mmol) in ethanol (7 mL) and 25% NaOH (7 mL) was heated to 83° C. for 16 h. The resultant solid was filtered, washed with ethanol and water then dried in vacuo to give 2-(5-amino-3-(4-fluorophenyl)-4-(phenylethynyl)-1H-pyrazol-1-yl)acetic acid as a solid (521 mg), which was used as such in the subsequent step.

Step 6: 2-(4-chloro-3-(4-fluorophenyl)-5-phenyl-1H-pyrazolo[3,4-c]pyridazin-1-yl)acetic acid

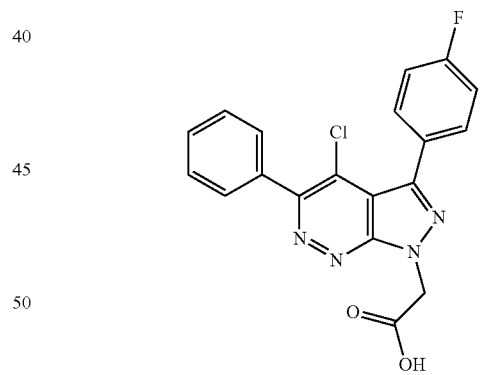

To a cooled (cooling bath −5° C.) stirred suspension of sodium nitrite (320 mg, 4.65 mmol) in conc. HCl (5 mL) was added 2-(5-amino-3-(4-fluorophenyl)-4-(phenylethynyl)-1H-pyrazol-1-yl)acetic acid (521 mg, 1.55 mmol). A further 5 ml of conc. HCl was added and the cooling bath was removed and the reaction mixture was stirred at room temperature for 3.5 h. Water and $CH_2Cl_2$ were added to the reaction mixture. The aqueous phase was extracted with $CH_2Cl_2$ and the organic phases combined, dried over $MgSO_4$, filtered and evaporated to give 2-(4-chloro-3-(4-fluorophenyl)-5-phenyl-1H-pyrazolo[3,4-c]pyridazin-1-yl)acetic acid as a solid (419 mg), which was used as such in the subsequent step.

Step 7: 2-(4-chloro-3-(4-fluorophenyl)-5-phenyl-1H-pyrazolo[3,4-c]pyridazin-1-yl)-1-morpholinoethanone

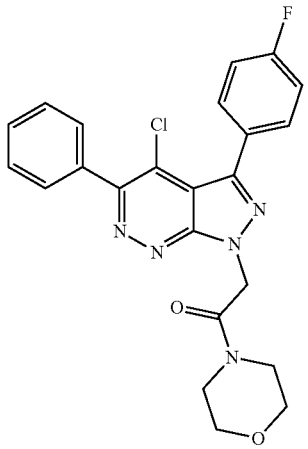 [SMILES: O=C(Cn1nc(-c2ccc(F)cc2)c2c(Cl)c(-c3ccccc3)nnc21)N1CCOCC1]

To a suspension of 2-(4-chloro-3-(4-fluorophenyl)-5-phenyl-1H-pyrazolo[3,4-c]pyridazin-1-yl)acetic acid (150 mg, 0.39 mmol) in $CH_2Cl_2$ (3 mL) were added morpholine (34 mg, 0.39 mmol), diisopropylethylamine (DIPEA) (200 µL, 1.2 mmol) and 2-(7-aza-1H-benzotriazole-1-yl)-1,1,3,3-tetramethyluronium hexafluorophosphate (HATU) (180 mg, 0.47 mmol). The solution obtained was stirred at room temperature for 75 min before being purified using chromatography (silica gel, gradient 20 to 100% ethyl acetate/isohexane) followed by preparative HPLC yielding Compound 75 as a clear glass solid (11.5 mg).

LCMS (10 cm_ESCI_Formic_MeCN) Rt 4.12 min; m/z 452 [M+H] 99.32% purity.

Example 69: 2-(4-chloro-3-(3-fluorophenyl)-5-phenyl-1H-pyrazolo[3,4-c]pyridazin-1-yl)-1-morpholinoethanone (Compound 76)

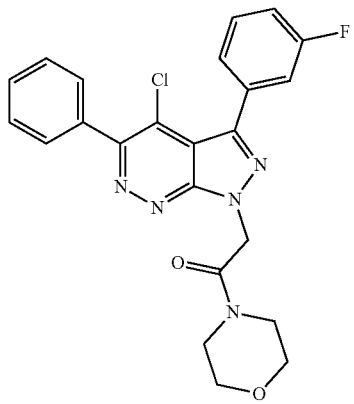 [SMILES: O=C(Cn1nc(-c2cccc(F)c2)c2c(Cl)c(-c3ccccc3)nnc21)N1CCOCC1]

Example 69 (Compound 76) was synthesised following a similar procedure outlined in Example 68 (Compound 75), using 3-fluorobenzoylacetonitrile instead of 4-fluorobenzoylacetonitrile in step 1. Compound 76 was obtained as a yellow solid (4.8 mg).

LCMS (15 cm_Bicarb_GeminiNX_HPLC_CH3CN) Rt 10.39 min; m/z 452 [M+H] 95.01% purity.

Example 70: 2-(4-chloro-3-(4-fluorophenyl)-5-phenyl-1H-pyrazolo[3,4-c]pyridazin-1-yl)ethanol (Compound 77)

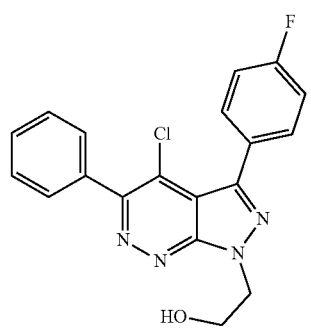 [SMILES: OCCn1nc(-c2ccc(F)cc2)c2c(Cl)c(-c3ccccc3)nnc21]

Compound 77 was synthesised starting from ethyl 2-(5-acetamido-3-(4-fluorophenyl)-4-(phenylethynyl)-1H-pyrazol-1-yl)acetate (Example 68, Step 4):

Step 1: N-(3-(4-fluorophenyl)-1-(2-hydroxyethyl)-4-(phenylethynyl)-1H-pyrazol-5-yl)acetamide

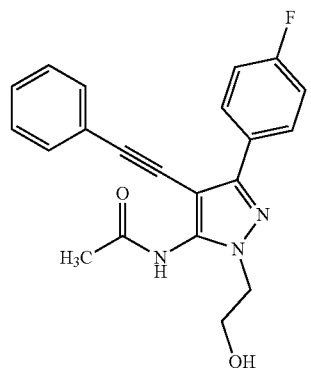 [SMILES: CC(=O)Nc1c(C#Cc2ccccc2)c(-c2ccc(F)cc2)nn1CCO]

To a solution of ethyl 2-(5-acetamido-3-(4-fluorophenyl)-4-(phenylethynyl)-1H-pyrazol-1-yl)acetate (1 g, 2.5 mmol) in ethanol (40 mL) and methanol (10 ml) was added sodium borohydride (466 mg, 12.3 mmol and the reaction stirred at room temperature for 16 h. The reaction mixture was concentrated in vacuo and the residue was dissolved in $CH_2Cl_2$ and washed with a dilute $NH_4Cl$ solution. The aqueous was extracted with $CH_2Cl_2$ and the combined organic extracts were dried over $MgSO_4$, filtered and evaporated. The crude product was suspended in $CH_2Cl_2$ (20 ml), heated to reflux, allowed to cool and the product was filtered and dried in vacuo to give N-(3-(4-fluorophenyl)-1-(2-hydroxyethyl)-4-(phenylethynyl)-1H-pyrazol-5-yl)acetamide as a white solid (659 mg), which was used as such in the subsequent step.

Step 2: 2-(5-amino-3-(4-fluorophenyl)-4-(phenylethynyl)-1H-pyrazol-1-yl)ethanol

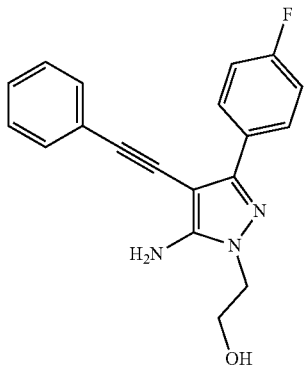 [SMILES: Nc1c(C#Cc2ccccc2)c(-c2ccc(F)cc2)nn1CCO]

A solution of N-(3-(4-fluorophenyl)-1-(2-hydroxyethyl)-4-(phenylethynyl)-1H-pyrazol-5-yl)acetamide (382 mg, 1.05 mmol) in ethanol (4 mL) and 25% NaOH (6 mL) was heated to 83° C. for 16 h. The reaction mixture was partitioned between ethyl acetate and water. The aqueous phase was washed with ethyl acetate twice and the organic phases combined, dried over MgSO$_4$, filtered and evaporated, purification using chromatography (silica gel, gradient 0 to 10% methanol/CH$_2$Cl$_2$) gave 2-(5-amino-3-(4-fluorophenyl)-4-(phenylethynyl)-1H-pyrazol-1-yl)ethanol as a solid (122 mg), which was used as such in the subsequent step.

Step 3: 2-(4-chloro-3-(4-fluorophenyl)-5-phenyl-1H-pyrazolo[3,4-c]pyridazin-1-yl)ethanol

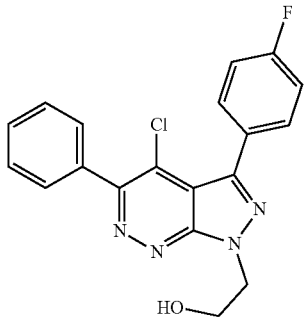 [SMILES: OCCn1nc(-c2ccc(F)cc2)c2c(Cl)c(-c3ccccc3)nnc21]

To a cooled (cooling bath −10° C.) stirred suspension of sodium nitrite (120 mg, 1.7 mmol) in conc. HCl (3.6 mL) was added 2-(5-amino-3-(4-fluorophenyl)-4-(phenylethynyl)-1H-pyrazol-1-yl)ethanol (183 mg, 0.57 mmol) and the reaction mixture was allowed to warm to ambient temperature over 90 min. Water and CH$_2$Cl$_2$ were added to the reaction mixture. The aqueous phase was extracted with CH$_2$Cl$_2$ (×4) and the organic phases combined, dried over MgSO$_4$, filtered and evaporated the crude material was purified using chromatography (silica gel, gradient 20 to 100% ethyl acetate/isohexane) followed by preparative HPLC yielding Compound 77 as a white solid (6.5 mg).

LCMS (10 cm_ESCI_Formic_MeCN) Rt 4.07 min; m/z 369 [M+H] 99.76% purity.

Example 71: 4-(2-(4-chloro-3-(4-fluorophenyl)-5-phenyl-1H-pyrazolo[3,4-c]pyridazin-1-yl)ethyl)morpholine (Compound 78)

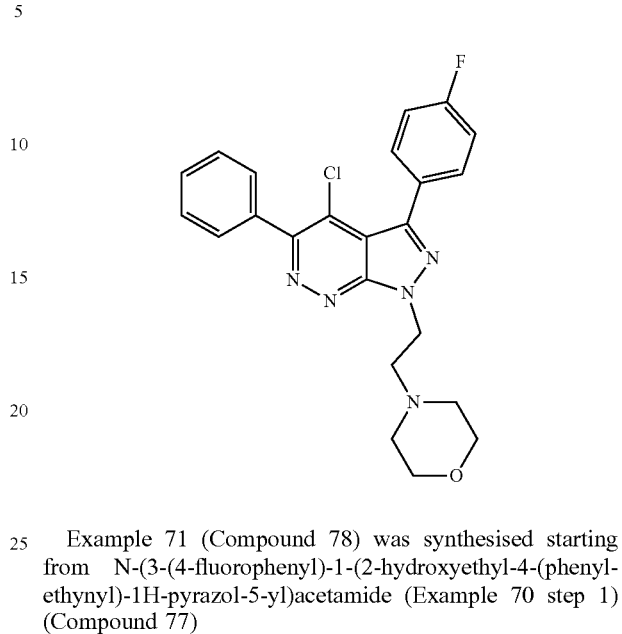

Example 71 (Compound 78) was synthesised starting from N-(3-(4-fluorophenyl)-1-(2-hydroxyethyl-4-(phenylethynyl)-1H-pyrazol-5-yl)acetamide (Example 70 step 1) (Compound 77)

Step 1: N-(3-(4-fluorophenyl)-1-(2-morpholinoethyl)-4-(phenylethynyl)-1H-pyrazol-5-yl)acetamide

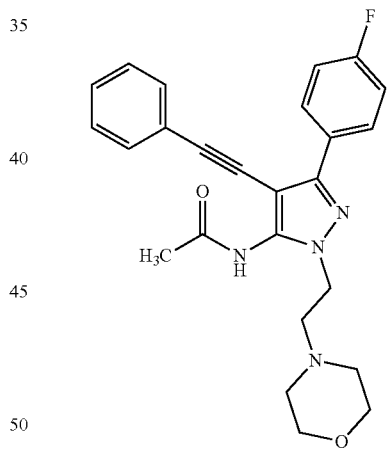

To a suspension of N-(3-(4-fluorophenyl)-1-(2-hydroxyethyl)-4-(phenylethynyl)-1H-pyrazol-5-yl)acetamide (269 mg, 0.74 mmol) in CH$_2$Cl$_2$ (9 mL) and triethylamine (155 µl, 1.11 mmol) was added methanesulphonyl chloride (65 µl, 0.81 mmol and the reaction stirred at room temperature for 16 h. The reaction mixture was poured onto ice/water and the organic layer was dried over MgSO$_4$, filtered and evaporated. The crude product was dissolved in THF (10 ml) and morpholine (320 µl, 3.7 mmol) was added. The reaction was heated to 55° C. for 24 h before evaporating the solvent in vacuo. The crude was partitioned between CH$_2$Cl$_2$ and dilute aqueous NaHCO$_3$ and the organic layer was dried over MgSO$_4$, filtered and evaporated. Purification using chromatography (silica gel, gradient 0 to 10% methanol/CH$_2$Cl$_2$) gave N-(3-(4-fluorophenyl)-1-(2-morpholinoethyl)-4-(phenylethynyl)-1H-pyrazol-5-yl)acetamide as a white solid (141 mg) which was used as such in the subsequent step.

Step 2: 3-(4-fluorophenyl)-1-(2-morpholinoethyl)-4-(phenylethynyl)-1H-pyrazol-5-amine

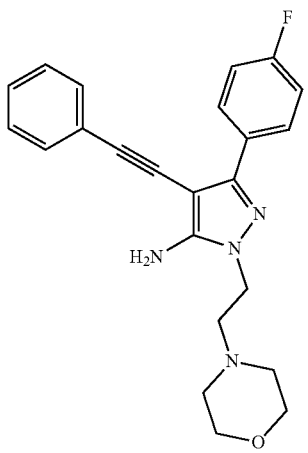 [SMILES: Nc1c(C#Cc2ccccc2)c(-c2ccc(F)cc2)nn1CCN1CCOCC1]

A solution of N-(3-(4-fluorophenyl)-1-(2-morpholinoethyl)-4-(phenylethynyl)-1H-pyrazol-5-yl)acetamide (141 mg, 0.32 mmol) in ethanol (1.5 mL) and 25% NaOH (1.5 mL) was heated to 83° C. for 16 h. The reaction mixture was partitioned between ethyl acetate and water. The aqueous phase was washed with ethyl acetate and the organic phases combined, dried over MgSO$_4$, filtered and evaporated to give 3-(4-fluorophenyl)-1-(2-morpholinoethyl)-4-(phenylethynyl)-1H-pyrazol-5-amine as a solid (129 mg) which was used as such in the subsequent step.

Step 3: 3-(4-fluorophenyl)-1-(2-morpholinoethyl)-5-phenyl-1H-pyrazolo[3,4-c]pyridazin-4-ol

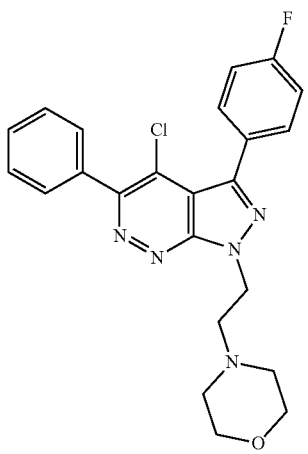 [SMILES: Fc1ccc(-c2nn(CCN3CCOCC3)c3nnc(-c4ccccc4)c(Cl)c23)cc1]

To a cooled (cooling bath −10° C.) stirred suspension of sodium nitrite (82 mg, 1.2 mmol) in conc. HCl (2.6 mL) was added a solution of 3-(4-fluorophenyl)-1-(2-morpholinoethyl)-4-(phenylethynyl)-1H-pyrazol-5-amine (129 mg, 0.33 mmol) in trifluoroacetic acid (0.5 ml) and the reaction mixture was allowed to warm to ambient temperature over 2 h. Water and CH$_2$Cl$_2$ were added. The aqueous phase was extracted with CH$_2$Cl$_2$ (×3) and the organic phases combined, dried over MgSO$_4$, filtered and evaporated. The crude material was purified by preparative HPLC to give 3-(4-fluorophenyl)-1-(2-morpholinoethyl)-5-phenyl-1H-pyrazolo[3,4-c]pyridazin-4-ol as a solid (27.8 mg) which was used as such in the subsequent step.

Step 4: 4-(2-(4-chloro-3-(4-fluorophenyl)-5-phenyl-1H-pyrazolo[3,4-c]pyridazin-1-yl)ethyl)morpholine (Compound 78)

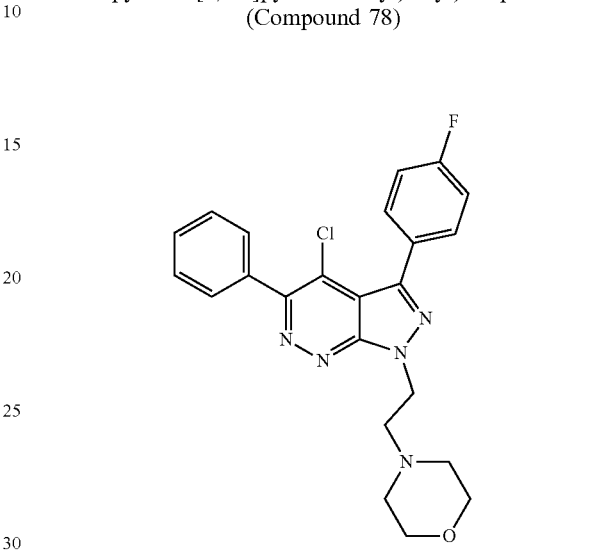

3-(4-fluorophenyl)-1-(2-morpholinoethyl)-5-phenyl-1H-pyrazolo[3,4-c]pyridazin-4-ol (27.8 mg, 0.07 mmol) was heated to 80° C. in POCl$_3$ (0.5 ml) for 2.75 h the solvent was removed in vacuo and the crude purified by preparative HPLC to give Compound 78 as an orange solid (10.7 mg).
LCMS (10 cm_ESCI_Formic_MeCN) Rt 2.87 min; m/z 438 [M+H] 99.73% purity.

Example 72: 2-(4-chloro-3-(3-fluorophenyl)-5-phenyl-1H-pyrazolo[3,4-c]pyridazin-1-yl)-1-(pyrrolidin-1-yl)ethanone (Compound 79)

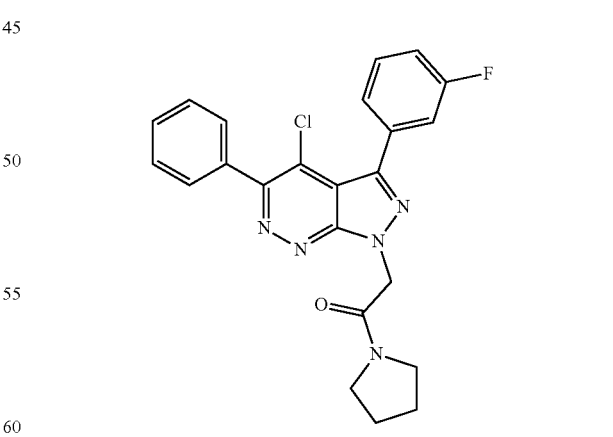

Example 72 (Compound 79) was synthesised following a similar procedure outlined in Example 68 (Compound 75), using 3-fluorobenzoylacetonitrile instead of 4-fluorobenzoylacetonitrile in step 1 and pyrrolidine instead of morpholine in step 7. Compound 79 was obtained as a yellow solid (13.1 mg).

LCMS (15 cm_Bicarb_GeminiNX_HPLC_CH3CN) Rt 10.68 min; m/z 436 [M+H] 96.6% purity.

Example 73: 2-(4-chloro-3-(4-fluorophenyl)-5-phenyl-1H-pyrazolo[3,4-c]pyridazin-1-yl)-1-(pyrrolidin-1-yl)ethanone (Compound 80)

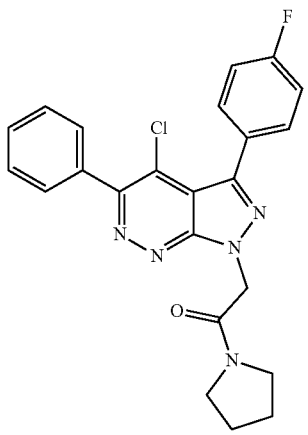 [SMILES: O=C(Cn1nc(-c2ccc(F)cc2)c2c(Cl)c(-c3ccccc3)nnc21)N1CCCC1]

Example 73 (Compound 80) was synthesised following a similar procedure outlined in Example 68, using pyrrolidine instead of morpholine in step 7. Compound 80 was obtained as a yellow solid (13.1 mg).

LCMS (15 cm_Bicarb_GeminiNX_HPLC_CH3CN) Rt 10.66 min; m/z 436 [M+H] 95.6% purity.

Example 74: 4-chloro-1-(2-(4-methylpiperazin-1-yl)ethyl)-3,5-diphenyl-1H-pyrazolo[3,4-c]pyridazine (Compound 81)

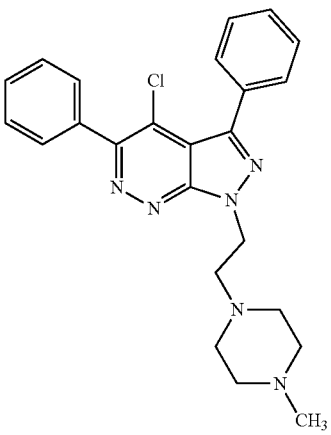 [SMILES: CN1CCN(CCn2nc(-c3ccccc3)c3c(Cl)c(-c4ccccc4)nnc32)CC1]

Example 74 was synthesised following a similar procedure outlined in Example 71, using N-methyl piperazine instead of morpholine in step 1. Compound 81 was obtained as a yellow solid (6.0 mg).

LCMS (15 cm_Formic_ASCE+NTIS_HPLC_CH3CN) Rt 8.01 min; m/z 433 [M+H] 98.4% purity.

Example 75: 4-chloro-3,5-diphenyl-1-vinyl-1H-pyrazolo[3,4-c]pyridazine (Compound 82)

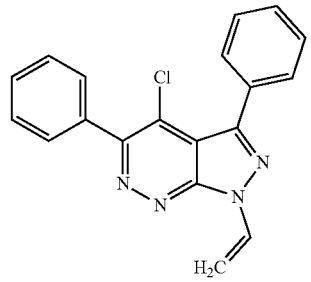 [SMILES: C=Cn1nc(-c2ccccc2)c2c(Cl)c(-c3ccccc3)nnc21]

Compound 82 was synthesised starting from 2-(4-chloro-3,5-diphenyl-1H-pyrazolo[3,4-c]pyridazin-1-yl)ethanol (Example 32)

Step 1: 4-chloro-1-(2-iodoethyl)-3,5-diphenyl-1H-pyrazolo[3,4-c]pyridazine

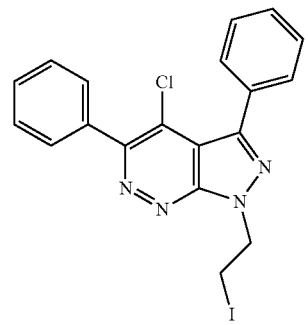 [SMILES: Clc1c(-c2ccccc2)nnc2c1c(-c1ccccc1)nn2CCI]

Triphenylphosphine (160 mg, 0.62 mmol), imidazole (42 mg, 0.62 mmol) and iodine (160 mg, 0.62 mmol) were added to a solution of 2-(4-chloro-3,5-diphenyl-1H-pyrazolo[3,4-c]pyridazin-1-yl)ethanol (181 mg, 0.52 mmol) in CH$_2$Cl$_2$ (6 ml). After stirring at ambient temperature for 1 h the reaction was filtered and solvent removed in vacuo. Purification using chromatography (silica gel, gradient 10 to 60% ethyl acetate/isohexane) gave 4-chloro-1-(2-iodoethyl)-3,5-diphenyl-1H-pyrazolo[3,4-c]pyridazine as a clear oil (202 mg) which was used as such in the subsequent step.

Step 2: 4-chloro-3,5-diphenyl-1-vinyl-1H-pyrazolo[3,4-c]pyridazine (Compound 82)

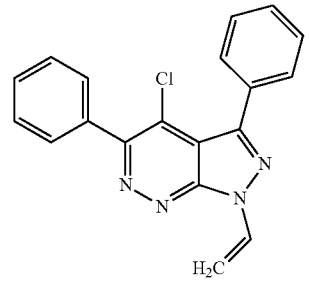 [SMILES: C=Cn1nc(-c2ccccc2)c2c(Cl)c(-c3ccccc3)nnc21]

A solution of 4-chloro-1-(2-iodoethyl)-3,5-diphenyl-1H-pyrazolo[3,4-c]pyridazine (53 mg, 0.11 mmol) in CH$_2$Cl$_2$ (1.5 ml) was added to trimethylethylene diamine (97 mg, 0.95 mmol) and the mixture stirred at ambient temperature for 3 days. The solvent was removed in vacuo and the crude purified by chromatography (silica gel, gradient 5 to 100% ethyl acetate/isohexane) to give Compound 82 as a yellow solid (12 mg).

LCMS (15 cm_Bicarb_GeminiNX_HPLC_CH3CN) Rt 11.63 min; m/z 333 [M+H] 95.16% purity.

Example 76: (R)-1-(2-(4-chloro-3,5-diphenyl-1H-pyrazolo[3,4-c]pyridazin-1-yl)ethyl)pyrrolidin-3-ol (Compound 83)

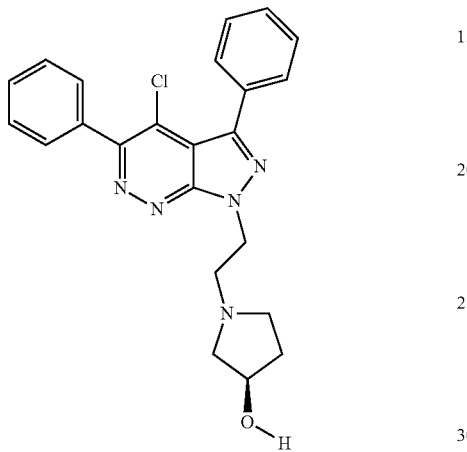

A solution of (R)-3-pyrrolidinol (166 mg, 1.9 mmol) in CH$_2$Cl$_2$ (1.5 ml) was added to 4-chloro-1-(2-iodoethyl)-3,5-diphenyl-1H-pyrazolo[3,4-c]pyridazine (example 74 step 1) (113 mg, 0.24 mmol) and the reaction stirred at ambient for 24 h. The resultant residue was purified using chromatography (silica gel, gradient 20 to 100% ethyl acetate/isohexane, then 0 to 100% ethyl acetate/acetone) followed by preparative HPLC to give Compound 83 as an orange solid (17 mg).

LCMS (15 cm_Bicarb_GeminiNX_HPLC_CH3CN) Rt 10.32 min; m/z 420 [M+H] 97.06% purity.

Example 77: 4-(2-(4-chloro-3,5-diphenyl-1H-pyrazolo[3,4-c]pyridazin-1-yl)ethyl)-1-methylpiperazin-2-one (Compound 84)

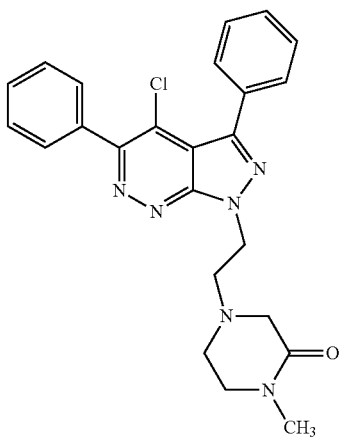 [SMILES: CN1CCN(CCn2nc(-c3ccccc3)c3c(Cl)c(-c4ccccc4)nnc32)CC1=O]

A solution of 4-chloro-1-(2-iodoethyl)-3,5-diphenyl-1H-pyrazolo[3,4-c]pyridazine (example 74 step 1 (Compound 81)) (100 mg, 0.21 mmol) in CH$_2$Cl$_2$ (1 ml) was added to piperazinone hydrochloride (160 mg, 1.05 mmol) and diisopropylethylamine (DIPEA) (220 µl, 12.6 mmol) in CH$_2$Cl$_2$ (0.5 ml) and the reaction stirred at ambient for 2 days. Further piperazinone hydrochloride (160 mg, 1.05 mmol) and diisopropylethylamine (DIPEA) (220 µl, 12.6 mmol) were added and the reaction stirred for a further 24 h. The resultant residue was purified using chromatography (silica gel, gradient 20 to 100% ethyl acetate/isohexane, then 0 to 100% ethyl acetate/acetone) followed by preparative HPLC to give Compound 84 as a yellow glass solid (17 mg).

LCMS (15 cm_Bicarb_GeminiNX_HPLC_CH3CN) Rt 10.21 min; m/z 447 [M+H] 97.76% purity.

Example 78: 1-(4-chloro-3,5-diphenyl-1H-pyrazolo[3,4-c]pyridazin-1-yl)-2-methylpropan-2-ol (Compound 85)

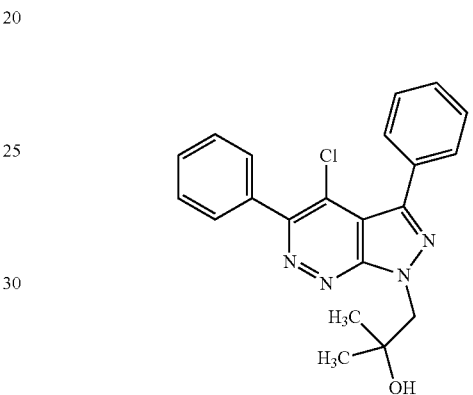

Step 1: N-(1-(2-hydroxy-2-methylpropyl)-3-phenyl-4-(phenylethynyl)-1H-pyrazol-5-yl)acetamide

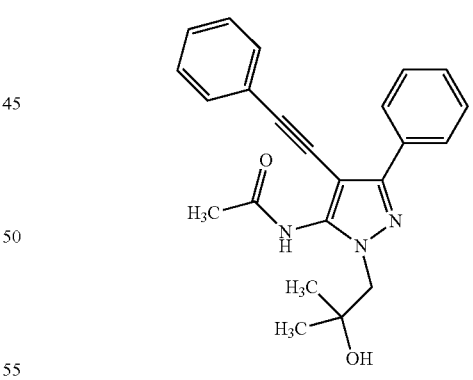

To a solution of ethyl 2-(5-acetamido-3-phenyl-4-(phenylethynyl)-1H-pyrazol-1-yl)acetate (1.0 g, 2.58 mmol) in tetrahydrofuran (THF, 26 mL) was added methyl magnesium chloride (3 M solution in THF, 3 mL, 9 mmol) at 0° C. The solution obtained was stirred at room temperature for 3.5 h then successively diluted with ethyl acetate and quenched by addition of 1 M hydrochloric acid. The aqueous phase was extracted with ethyl acetate, and the combined organic layers were dried over MgSO$_4$ and concentrated in vacuo. The resultant residue was purified using chromatography (silica gel, gradient 0 to 75% ethyl acetate/isohexane)

yielding N-(1-(2-hydroxy-2-methylpropyl)-3-phenyl-4-(phenylethynyl)-1H-pyrazol-5-yl)acetamide as a solid (529 mg).

Step 2: 1-(5-amino-3-phenyl-4-(phenylethynyl)-1H-pyrazol-1-yl)-2-methylpropan-2-ol

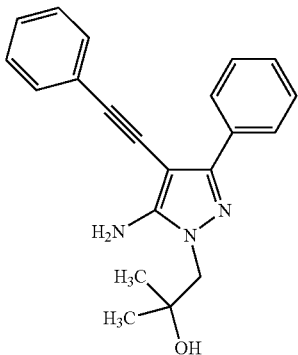 [SMILES: CC(C)(O)Cn1nc(-c2ccccc2)c(C#Cc2ccccc2)c1N]

1-(5-Amino-3-phenyl-4-(phenylethynyl)-1H-pyrazol-1-yl)-2-methylpropan-2-ol was synthesised following similar procedures outlined in Example 1 using N-(1-(2-hydroxy-2-methylpropyl)-3-phenyl-4-(phenylethynyl)-1H-pyrazol-5-yl)acetamide in step 5.

Step 3: 1-(4-chloro-3,5-diphenyl-1H-pyrazolo[3,4-c]pyridazin-1-yl)-2-methylpropan-2-ol

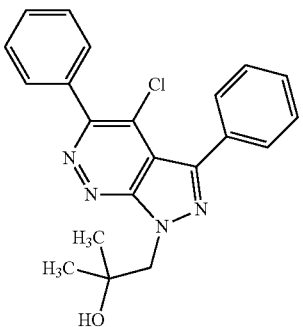 [SMILES: CC(C)(O)Cn1nc(-c2ccccc2)c2c(Cl)c(-c3ccccc3)nnc21]

To cooled (cooling bath −15° C.) conc. HCl (9 mL) was added sodium nitrite in one portion (121 mg, 1.75 mmol) and the suspension was left to stir for 10 min after which 1-(5-amino-3-phenyl-4-(phenylethynyl)-1H-pyrazol-1-yl)-2-methylpropan-2-ol (290 mg, 0.88 mmol) was added. After 5 min, the cooling bath was removed and the reaction mixture was stirred at room temperature for 3 h. The reaction was cooled again (0° C.) and DCM was added followed by water. The aqueous phase was extracted with DCM and the organic phases were combined, dried over MgSO$_4$, filtered and evaporated. Crude material was purified by column chromatography (silica gel, gradient 0 to 50% ethyl acetate/isohexane) yielding 1-(4-chloro-3,5-diphenyl-1H-pyrazolo[3,4-c]pyridazin-1-yl)-2-methylpropan-2-ol as an orange oil (56 mg). The material obtained was further purified by preparative HPLC, yielding 34 mg of Compound 85 as a solid.

LCMS (10 cm_ESCI_Formic_MeCN) Rt 4.49 min; m/z 379 [M+H] 99.71% purity.

Example 79: methyl 2-(4-chloro-3,5-diphenyl-1H-pyrazolo[3,4-c]pyridazin-1-yl)acetate (Compound 86)

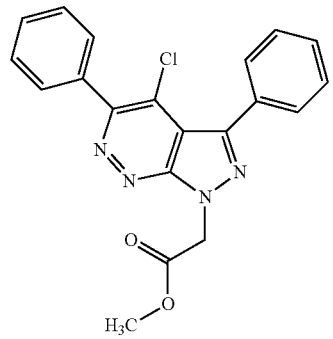 [SMILES: COC(=O)Cn1nc(-c2ccccc2)c2c(Cl)c(-c3ccccc3)nnc21]

A suspension of 2-(4-chloro-3,5-diphenyl-1H-pyrazolo[3,4-c]pyridazin-1-yl)acetic acid (528 mg, 1.45 mmol) in thionyl chloride (10 mL) was heated at 70° C. for one hour. The solvent was evaporated under reduced pressure and the residue was dissolved in anhydrous CH$_2$Cl$_2$. Anhydrous methanol (65 µL, 1.6 mmol) was added at 0° C. and the reaction mixture was allowed to slowly reach room temperature overnight. After removal of solvents under reduced pressure, the crude mixture was directly loaded onto a silica gel column and the product was eluted using mixtures of ethyl acetate/isohexane (gradient 0 to 40%). Half of the material obtained was further purified by preparative HPLC, yielding 13.4 mg of Compound 86.

LCMS (10 cm_ESCI_Bicarb_MeCN) Rt 10.9 min; m/z 379 [M+H] 94.66% purity.

Example 80: 1-(azetidin-1-yl)-2-(4-chloro-3,5-diphenyl-1H-pyrazolo[3,4-c]pyridazin-1-yl)ethanone (Compound 87)

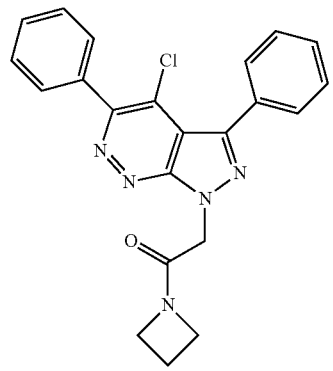 [SMILES: O=C(Cn1nc(-c2ccccc2)c2c(Cl)c(-c3ccccc3)nnc21)N1CCC1]

1-(Azetidin-1-yl)-2-(4-chloro-3,5-diphenyl-1H-pyrazolo[3,4-c] pyridazin-1-yl)ethanone was synthesised following similar procedures outlined in Example 39 using 2-(4-chloro-3,5-diphenyl-1H-pyrazolo[3,4-c]pyridazin-1-yl)acetic acid. Chromatography (silica gel, gradient 0 to 70% ethyl acetate/isohexane) followed by preparative HPLC purification yielded 17 mg of Compound 87.

LCMS (10 cm_ESCI_Formic) Rt 10.34 min; m/z 404 [M+H] 97.37% purity.

Example 81: (S)-2-(4-chloro-3,5-diphenyl-1H-pyrazolo[3,4-c]pyridazin-1-yl)-1-(3-fluoropyrrolidin-1-yl)ethanone (Compound 88)

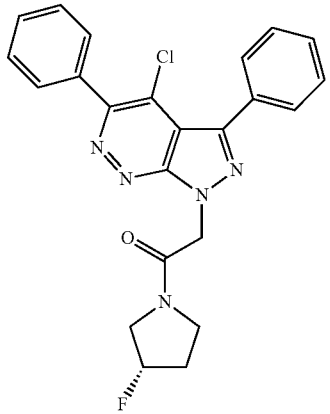 [SMILES: O=C(Cn1nc(-c2ccccc2)c2c(Cl)c(-c3ccccc3)nnc21)N1CC[C@H](F)C1]

A solution of 2-(4-chloro-3,5-diphenyl-1H-pyrazolo[3,4-c]pyridazin-1-yl)acetic acid (170 mg, 0.47 mmol) in thionyl chloride (4.7 mL) was heated at 60° C. for 1.5 h. The solvent was evaporated under reduced pressure and the residue was dissolved in anhydrous $CH_2Cl_2$ (4.7 mL). The reaction mixture was split into two tubes and (S)-fluoropyrrolidine hydrochloride (125 mg, 0.26 mmol), followed by triethylamine (72 µL, 0.52 mmol) was added to one of them. The reaction mixture was stirred at room temperature overnight, then concentrated under reduced pressure. The resultant residue was purified using chromatography (silica gel, gradient 0 to 25% diethyl ether/$CH_2Cl_2$) to yield 15 mg of Compound 88.

LCMS (10 cm_ESCI_Bicarb_MeCN) Rt 4.0 min; m/z 436 [M+H] 96.15% purity.

Example 82: (R)-2-(4-chloro-3,5-diphenyl-1H-pyrazolo[3,4-c]pyridazin-1-yl)-1-(3-fluoropyrrolidin-1-yl)ethanone (Compound 89)

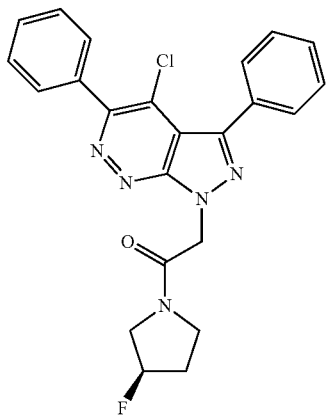 [SMILES: O=C(Cn1nc(-c2ccccc2)c2c(Cl)c(-c3ccccc3)nnc21)N1CC[C@@H](F)C1]

(R)-2-(4-chloro-3,5-diphenyl-1H-pyrazolo[3,4-c]pyridazin-1-yl)-1-(3-fluoropyrrolidin-1-yl)ethanone was synthesised following similar procedures outlined in Example 81 and purified by chromatography (silica gel, gradient 0 to 25% diethyl ether/$CH_2Cl_2$) to yield 17 mg of Compound 89.

LCMS (10 cm_ESCI_Bicarb_MeCN) Rt 3.97 min; m/z 436 [M+H] 96.09% purity.

Example 83: 2-(4-chloro-3,5-diphenyl-1H-pyrazolo[3,4-c]pyridazin-1-yl)-1-(3,3-difluoroazendin-1-yl)ethanone (Compound 90)

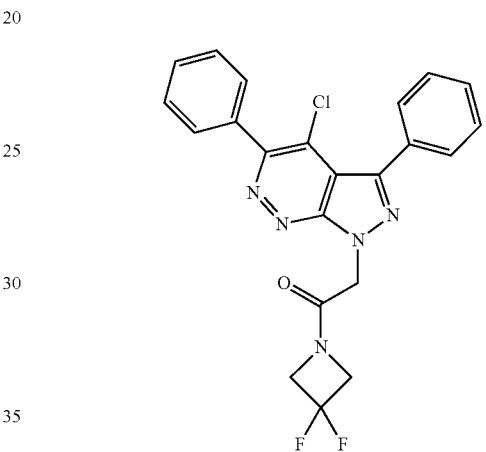

2-(4-chloro-3,5-diphenyl-1H-pyrazolo[3,4-c]pyridazin-1-yl)-1-(3,3-difluoroazetidin-1-yl)ethanone was synthesised following similar procedures outlined in Example 81 and purified by preparative HPLC, yielding 29 mg of Compound 90 as a white solid.

LCMS (10 cm_ESCI_Bicarb_MeCN) Rt 3.71 min; m/z 440 [M+H] 98.92% purity.

Example 84: 1-(4-chloro-3,5-diphenyl-1H-pyrazolo[3,4-c]pyridazin-1-yl)propan-2-ol (Compound 91)

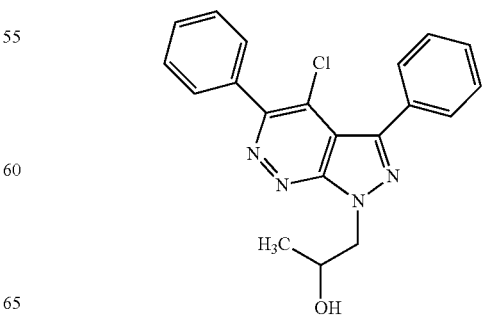

139

Step 1: 2-(4-chloro-3,5-diphenyl-1H-pyrazolo[3,4-c]pyridazin-1-yl)acetaldehyde

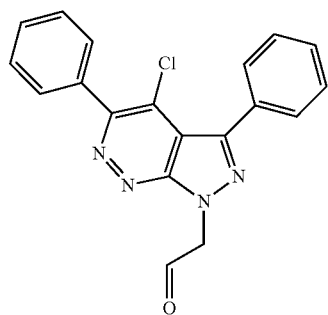 [SMILES: O=CCn1nc(-c2ccccc2)c2c(Cl)c(-c3ccccc3)nnc21]

To a solution of 2-(4-chloro-3,5-diphenyl-1H-pyrazolo[3,4-c]pyridazin-1-yl)ethanol (300 mg, 0.86 mmol) in CH$_2$Cl$_2$ (5.7 mL) was added Dess-Martin periodinane (DMP, 437 mg, 1.03 mmol) at room temperature. The mixture was stirred at room temperature for 35 min, then the solids were filtered off and the filtrate was stirred with aqueous NaHCO$_3$ and Na$_2$S$_2$O$_3$ for one hour. The aqueous phase was re-extracted with CH$_2$Cl$_2$ and the combined organic layers were passed over a phase separator and concentrated under reduced pressure. The crude aldehyde 2-(4-chloro-3,5-diphenyl-1H-pyrazolo[3,4-c]pyridazin-1-yl)acetaldehyde (384 mg) was used directly in the following step.

Step 2: 1-(4-chloro-3,5-diphenyl-1H-pyrazolo[3,4-c]pyridazin-1-yl)propan-2-ol (Compound 91)

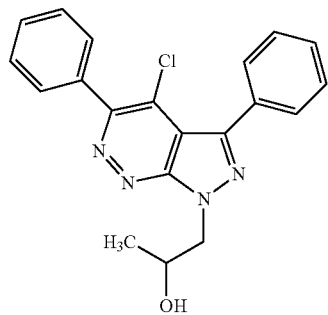 [SMILES: CC(O)Cn1nc(-c2ccccc2)c2c(Cl)c(-c3ccccc3)nnc21]

A solution of 2-(4-chloro-3,5-diphenyl-1H-pyrazolo[3,4-c]pyridazin-1-yl)acetaldehyde (128 mg, 0. 29 mmol) in THF (2.9 mL) was added dropwise over 30 min to a solution of methyl magnesium chloride (290 µL of 3 M solution diluted in 2.9 mL THF) at 0° C. The crude mixture was partitioned between CH$_2$Cl$_2$ and 2 M hydrochloric acid. The aqueous phase was extracted with CH$_2$Cl$_2$ and the combined organic layers were passed over a phase separator and concentrated under reduced pressure. The reaction was repeated with another 80 mg of starting 2-(4-chloro-3,5-diphenyl-1H-pyrazolo[3,4-c]pyridazin-1-yl)acetaldehyde and the combined crude mixtures were purified by column chromatography (silica gel, gradient 50 to 100% ethyl acetate/isohexane). Additional preparative HPLC purification yielded 7.2 mg of Compound 91.

LCMS (10 cm_ESCI_Bicarb_MeCN) Rt 10.57 min; m/z 365 [M+H] 96.2% purity.

140

Example 85: 1-(4-chloro-3,5-diphenyl-1H-pyrazolo[3,4-c]pyridazin-1-yl)propan-2-ol (Compound 92)

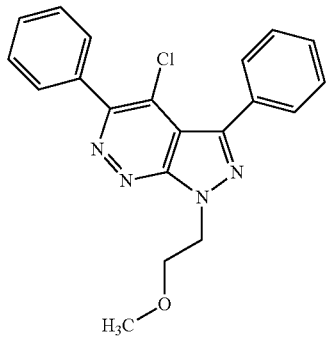 [SMILES: COCCn1nc(-c2ccccc2)c2c(Cl)c(-c3ccccc3)nnc21]

Step 1: 4-chloro-3,5-diphenyl-1H-pyrazolo[3,4-c]pyridazine

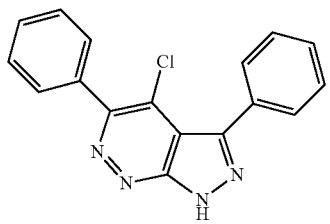 [SMILES: Clc1c(-c2ccccc2)nnc2[nH]nc(-c3ccccc3)c12]

To a solution of 4-chloro-3,5-diphenyl-1-vinyl-1H-pyrazolo[3,4-c]pyridazine (50 mg, 0.15 mmol) in acetone (5 mL) was added a 2% aqueous solution of potassium permanganate (71 mg, 0.45 mmol, 3.5 mL water) in one portion. The mixture was stirred at room temperature for 2 h, then another portion of potassium permanganate (12 mg, 0.075 mmol), was added and stirring continued for 15 min. The solids were filtered off and the filtrate was partitioned between water and CH$_2$Cl$_2$. The aqueous phase was re-extracted with CH$_2$Cl$_2$ and the combined organic layers were dried over MgSO$_4$ and concentrated under reduced pressure. The crude 4-chloro-3,5-diphenyl-1H-pyrazolo[3,4-c]pyridazine (64 mg) was used directly in the following step.

Step 2: 1-(4-chloro-3,5-diphenyl-1H-pyrazolo[3,4-c]pyridazin-1-yl)propan-2-ol (Compound 92)

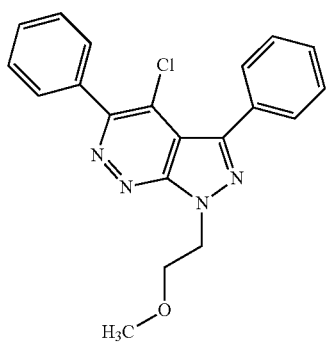 [SMILES: COCCn1nc(-c2ccccc2)c2c(Cl)c(-c3ccccc3)nnc21]

A solution of 4-chloro-3,5-diphenyl-1H-pyrazolo[3,4-c]pyridazine (45 mg, 0.15 mmol) in dimethylformamide (DMF, 1.5 mL) was successively treated with cesium carbonate (64 mg, 0.2 mmol) and 2-methoxyethyl bromide (31.3 mg, 0.23 mmol). The crude mixture was heated at 130° C. in the microwave for 30 min, then filtered off. The filtrate was evaporated down under reduced pressure and purified by preparative HPLC, yielding 27 mg of Compound 92.

LCMS (10 cm_ESCI_Bicarb_MeCN) Rt 11.16 min; m/z 365 [M+H] 97.33% purity.

Example 86: 4-chloro-1-(oxetan-3-yl)-3,5-diphenyl-1H-pyrazolo[3,4-c]pyridazine (Compound 93)

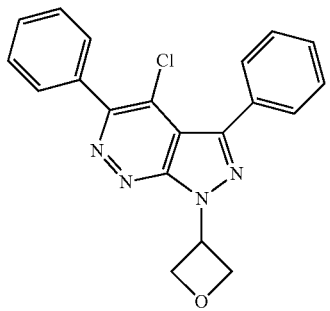 [SMILES: Clc1c(-c2ccccc2)nnc2c1c(-c1ccccc1)nn2C1COC1]

A solution of 4-chloro-3,5-diphenyl-1H-pyrazolo[3,4-c]pyridazine (50 mg, 0.16 mmol) in dioxane (0.5 mL) was treated with oxetan-3-ol (24 mg, 0.32 mmol), triphenylphosphine (84 mg, 0.32 mmol) and diethyl azodicarboxylate (DEAD, 56 mg, 0.32 mmol) and heated in the microwave at 85° C. for 30 min. The crude mixture evaporated down under reduced pressure and purified by preparative HPLC, and subsequently by column chromatography (silica gel, gradient 0 to 15% diethyl ether/CH₂Cl₂) to give 23 mg of Compound 93 as a white solid.

LCMS (10 cm_ESCI_Formic_MeCN) Rt 10.95 min; m/z 363 [M+H] 98.12% purity.

Example 87: 2-(4-chloro-3-(3-fluorophenyl)-5-phenyl-1H-pyrazolo[3,4-c]pyridazin-1-yl)ethanol (Compound 94)

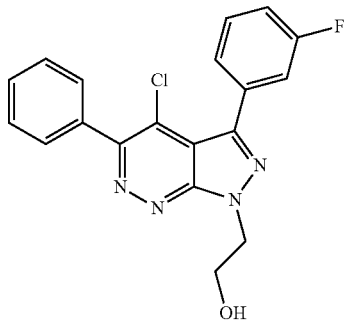 [SMILES: OCCn1nc(-c2cccc(F)c2)c2c(Cl)c(-c3ccccc3)nnc21]

Compound 94 was synthesised starting from ethyl 2-(5-acetamido-3-(3-fluorophenyl)-4-(phenylethynyl)-1H-pyrazol-1-yl)acetate. Ethyl 2-(5-acetamido-3-(3-fluorophenyl)-4-(phenylethynyl)-1H-pyrazol-1-yl)acetate was synthesised following a similar procedure outlined in Example 68 (steps 1 to 4), using 3-fluorobenzoylacetonitrile instead of 4-fluorobenzoylacetonitrile in step 1.

Step 1: 2-(5-amino-3-(3-fluorophenyl)-4-(phenylethynyl)-1H-pyrazol-1-yl)ethanol

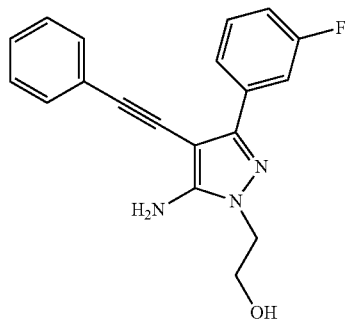 [SMILES: Nc1c(C#Cc2ccccc2)c(-c2cccc(F)c2)nn1CCO]

To a solution of ethyl 2-(5-acetamido-3-(3-fluorophenyl)-4-(phenylethynyl)-1H-pyrazol-1-yl)acetate (3.25 g, 8.02 mmol) in ethanol (90 mL) was added sodium borohydride (610 mg, 16.04 mmol) and the reaction stirred at room temperature for 36 h. Additional sodium borohydride was added (305 mg, 8.02 mmol) and the reaction stirred at room temperature for 36 h. 25% NaOH (0.9 mL) was added and the reaction mixture was stirred at 80° C. for 3.5 h. The reaction mixture was partitioned between ethyl acetate and water. The aqueous phase was washed with ethyl acetate twice and the organic phases combined, dried over MgSO₄, filtered and evaporated. The crude material was suspended in diethylether (30 mL) and the product was filtered and dried in vacuo to give 2-(5-amino-3-(3-fluorophenyl)-4-(phenylethynyl)-1H-pyrazol-1-yl)ethanol as a white solid (2.2 g), which was used as such in the subsequent step.

Step 2: 2-(4-chloro-3-(3-fluorophenyl)-5-phenyl-1H-pyrazolo[3,4-c]pyridazin-1-yl)ethanol

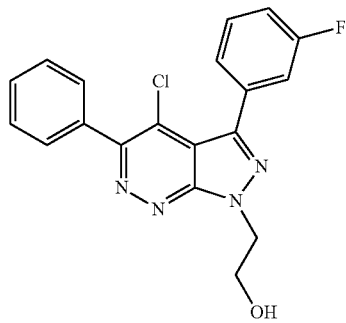 [SMILES: OCCn1nc(-c2cccc(F)c2)c2c(Cl)c(-c3ccccc3)nnc21]

Sodium nitrite (555 mg, 8.04 mmol) was added portionwise to a cooled (cooling bath −10° C.) stirred solution of conc. HCl (11.7 mL). After 15 minutes, 2-(5-amino-3-(3-fluorophenyl)-4-(phenylethynyl)-1H-pyrazol-1-yl)ethanol (860 mg, 2.68 mmol) was added portionwise and the reaction mixture was allowed to warm to room temperature over 90 min. Water and CH₂Cl₂ were added to the reaction mixture. The aqueous phase was extracted with CH₂Cl₂ (×4) and the organic phases combined, dried over MgSO₄, filtered and evaporated the crude material was purified using chromatography (silica gel, gradient 0 to 50% ethyl acetate/ isohexane) followed by preparative HPLC yielding Compound 94 as a white solid (40 mg).

LCMS (15 cm_Bicarb_GeminiNX_HPLC_CH3CN) Rt 10.39 min; m/z 369 [M+H] 96.26% purity.

Example 88: 2-(4-chloro-3-(3,5-difluorophenyl)-5-phenyl-1H-pyrazolo[3,4-c]pyridazin-1-yl)ethanol (Compound 95)

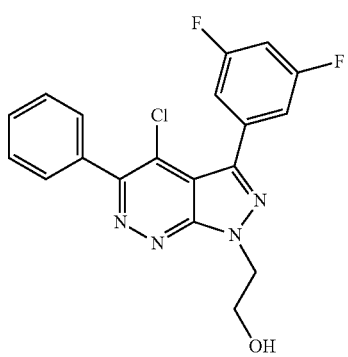 [SMILES: OCCn1nc(-c2cc(F)cc(F)c2)c2c(Cl)c(-c3ccccc3)nnc21]

Compound 95 was synthesised following a similar procedure outlined in Example 70, using 3-(3,5-difluorophenyl)-3-oxopropanenitrile instead of 4-fluorobenzoylacetonitrile in step 1.

Synthesis of 3-(3,5-difluorophenyl)-3-oxopropanenitrile

Diisopropylamine (10.6 mL, 76 mmol) was dissolved in dry THF (10 mL) and the solution cooled to −20° C. A solution of n-butyllithium (2.5N in hexanes, 30.5 mL, 76 mmol) was added slowly at such a rate as to keep the internal temperature below 0° C. After stirring for 5 min, the solution was cooled to −20° C. and added to a solution of acetonitrile (2.37 mL, 45.3 mmol) and ethyl 3,5-difluorobenzoate (6.23 g, 36.2 mmol) in dry THF (18 mL) at such a rate as to keep the temperature below −40° C. A further 10 mL of dry THF was used to transfer the remaining lithium diisopropylamide to the reaction. The reaction was allowed to warm to ambient over 2 h before being quenched with saturated aqueous ammonium chloride solution. The reaction was extracted with ethyl acetate (×2) and the extracts discarded. The aqueous was acidified with 2N HCl and extracted with ethyl acetate. The organic extract was washed with 2N HCl and brine before being dried over MgSO4, filtered and evaporated. Purification using chromatography (silica gel, gradient 5 to 100% ethyl acetate/isohexane) gave 3-(3,5-difluorophenyl)-3-oxopropanenitrile as a yellow solid (2.82 g).

Compound 95 was synthesised following a similar procedure outlined in Example 70, using 3-(3,5-difluorophenyl)-3-oxopropanenitrile instead of 4-fluorobenzoylacetonitrile in step 1. Compound 95 was obtained as a tan solid (30.6 mg).

LCMS (10 cm_Formic_ACE 3 C18 AR_HPLC_CH3CN) Rt 11.89 min; m/z 387 [M+H] 95.85% purity.

Example 89: 2-(4-chloro-3,5-diphenyl-1H-pyrazolo[3,4-c]pyridazin-1-yl)propan-1-ol (Compound 96)

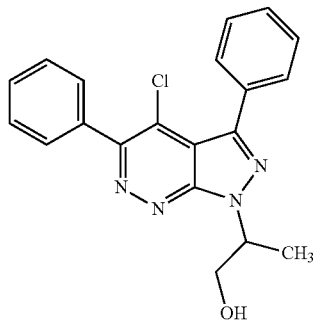 [SMILES: CC(CO)n1nc(-c2ccccc2)c2c(Cl)c(-c3ccccc3)nnc21]

Step 1: Ethyl 2-(4-chloro-3,5-diphenyl-1H-pyrazolo[3,4-c]pyridazin-1-yl)propanoate

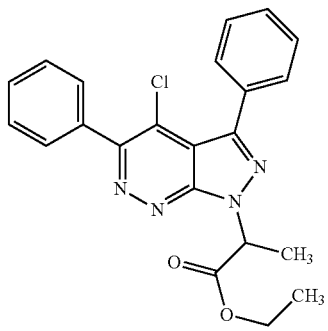 [SMILES: CCOC(=O)C(C)n1nc(-c2ccccc2)c2c(Cl)c(-c3ccccc3)nnc21]

Ethyl 2-(4-chloro-3,5-diphenyl-1H-pyrazolo[3,4-c]pyridazin-1-yl)propanoate was synthesised following a similar procedure outlined in Example 85, using ethyl 2-bromopropionate instead of 2-methoxyethyl bromide in step 2.

Step 2: 2-(4-chloro-3,5-diphenyl-1H-pyrazolo[3,4-c]pyridazin-1-yl)propan-1-ol (Compound 96)

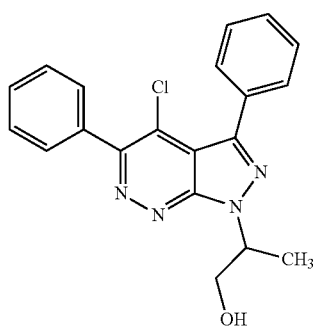 [SMILES: CC(CO)n1nc(-c2ccccc2)c2c(Cl)c(-c3ccccc3)nnc21]

To a cooled (0° C.) stirred solution of ethyl 2-(4-chloro-3,5-diphenyl-1H-pyrazolo[3,4-c]pyridazin-1-yl)propanoate (72 mg, 0.177 mmol) in THF (0.5 mL) was added dropwise a 1.1 M solution of diisobutylaluminium hydride in cyclohexane (1 mL, 1.1 mmol). After 15 minutes, a saturated solution of ammonium chloride and $CH_2Cl_2$ were added at 0° C. to the reaction mixture. The aqueous phase was extracted with $CH_2Cl_2$ and the organic phases combined, dried over $MgSO_4$, filtered and evaporated. Purification using preparative HPLC gave Compound 96 as an off-white solid (28 mg).

LCMS (10 cm_ESCI_Formic_MeCN) Rt 4.32 min; m/z 365 [M+H] 99.30% purity.

Example 90: 4-chloro-3,5-diphenyl-1-(tetrahydrofuran-3-yl)-1H-pyrazolo[3,4-c]pyridazine (Compound 97)

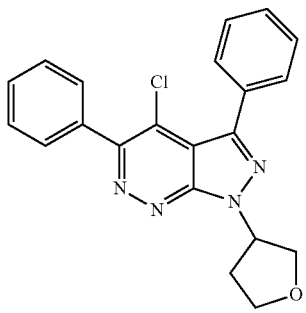 [SMILES: Clc1c(-c2ccccc2)nnc2c1c(-c1ccccc1)nn2C1CCOC1]

Compound 97 was synthesised from 4-chloro-3,5-diphenyl-1H-pyrazolo[3,4-c]pyridazine (50 mg, 0.16 mmol) following a similar procedure outlined in Example 86, using 3-hydroxytetrahydrofuran (28 mg, 0.32 mmol) instead of oxetan-3-ol. Compound 97 was purified using preparative HPLC followed by chromatography (silica gel, gradient $CH_2Cl_2$), yielding Compound 97 as an off-white solid (21 mg).

LCMS (10 cm_ESCI_Formic_MeCN) Rt 4.64 min; m/z 377 [M+H] 99.42% purity.

Example 91: Liquid Chromatography-Mass Spectrometry (LC-MS)

LC-MS Conditions for the Pyrazolopyridizines Compounds of the Invention.

(a) Standard Acidic LC-MS Conditions: (10 cm_ESI_Formic or 10 cm_ESCI_Formic)

A Phenomenex Luna 5 μm C18 (2), 100×4.6 mm (plus guard cartridge) column using an acetonitrile (Far UV grade) with 0.1% (V/V) formic acid: water (high purity via PureLab Option unit) with 0.1% formic acid gradient was used. The flow rate was 2 mL/min. UV detection was done using a Waters diode array detector (start Range 210 nm, end range 400 nm, range interval 4 nm). Mass detection was performed via a single quadrapole LC-MS instrument. Ionisation is either ESI or APCI dependent on compound types. The gradient used ran from 95% of aqueous solvent at time 0.00 min to 5% of aqueous solvent at 3.50 min. This percentage was then held for a further 2 min.

(b) Standard Basic LC-MS Conditions: (10 cm_ESCI_Bicarb or 10 cm_ESI_Bicarb):

A Waters Xterra MS 5 μm C18, 100×4.6 mm (plus guard cartridge) using an acetonitrile (Far UV grade): water (high purity via PureLab Option unit) with 10 mM ammonium bicarbonate (ammonium hydrogen carbonate) gradient was used. The flow rate was 2 mL/min. UV detection was performed using a Waters diode array detector (start Range 210 nm, end range 400 nm, range interval 4 nm). Mass detection was performed via a single quadrapole LC-MS instrument. Ionisation is either ESI or APCI dependent on compound types. The gradient used ran from 95% of aqueous solvent at time 0.00 min to 5% of aqueous solvent at 4.0 min. This percentage was then held for a further 1.5 min.

(c) Standard Acidic HPLC Conditions: (15 cm_Formic_ASCENTIS_HPLC)

A Supelco Ascentis® Express C18 or Hichrom Halo C18, 2.7 m C18, 150×4.6 mm column using an acetonitrile (Far UV grade) with 0.1% (V/V) formic acid: water (high purity via PureLab Option unit) with 0.1% formic acid gradient was used. The flow rate was 1 mL/min. UV detection was done using an Agilent diode array detector (300 nm, band width 200 nm; ref 450 nm, band width 100 nm). The gradient used ran from 96% of aqueous solvent at time 0.00 min to 0% of aqueous solvent at 9.00 min. This percentage was then held for a further 4.5 min.

(d) Standard Basic HPLC Conditions: (15 cm_Bicarb_GeminiNX_HPLC)

A Phenomenex Gemini NX, 3 μm C18, 150×4.6 mm column using an acetonitrile (Far UV grade): water (high purity via PureLab Option unit) with 10 mM ammonium bicarbonate gradient was used. The flow rate was 1 mL/min. UV detection was done using an Agilent diode array detector (300 nm, band width 200 nm; ref 450 nm, band width 100 nm). The gradient used ran from 95.5% of aqueous solvent at time 0.00 min to 0% of aqueous solvent at 9.00 min. This percentage was then held for a further 4.5 min.

(e) Standard Acidic HPLC Conditions: (10 cm_Formic_ACE 3 C18 AR_HPLC_CH3CN)

A Hichrom ACE 3 C18-AR mixed mode 100×4.6 mm column using an acetonitrile (Far UV grade) with 0.1% (V/V) formic acid: water (high purity via PureLab Option unit) with 0.1% formic acid gradient was used. The flow rate was 1 mL/min. UV detection was done using an Agilent diode array detector (300 nm, band width 200 nm; ref 450 nm, band width 100 nm). The gradient used ran from 98% of aqueous solvent from time 0.00 min to 3.00 min, to 100% of aqueous solvent at 12.00 min. This percentage was then held for a further 2.4 min.

Example 92: Assay Method Showing Activity of Compounds of the Invention that Restore Expression of N48K Clarin-1

Clarin-1 is the protein encoded by the gene mutated in Usher III Syndrome (Adato et al., 2002). The most prevalent mutation in Clarin-1 in North America is N48K, which is reported to cause loss of glycosylation and a trafficking defect (Tian et al., 2009). As a consequence, the N48K protein does not reach the plasma membrane and is degraded by the proteasome. Thus it is believed that restoring the trafficking of N48K Clarin-1 to the cell surface would provide an avenue of intervention for Usher III Sydrome.

A useful cellular model to demonstrate the utility of compounds of the invention that restore expression of N48K Clarin-1 is the HEK293-Clarin-1 N48K-HA D9 cell line (Tian et al., 2009). In a typical experiment, these cells are seeded on collagen-coated 96-well plates at a cell density of 20,000 cells per well in Dulbecco's Modified Eagle Medium (DMEM) contain 10% fetal bovine serum in a humidified incubator at 37° C., 5% $CO_2$. After an overnight incubation, compounds are added for a 24 hr incubation in DMEM medium contain 10% fetal bovine serum in a humidified incubator at 37° C., 5% $CO_2$. As a negative control, DMSO is used at 0.25% final concentrations. Compounds are typically tested in triplicate fashion. After the 24 hr incubation with compounds, the cells are fixed by the addition of 10% buffered formalin to the wells to achieve a final concentration of 4% formalin. After a 20 min fixation at room temperature, wells are washed three times with phosphate-buffered saline (PBS) containing Triton X-100 (0.02 phosphate, 150 mM NaCl, 0.1% Triton X-100).

The HA-tagged N48K Clarin-1 is detected with an antibody against the HA tag (HA.11 Clone 16B12 Monoclonal antibody, Covance #MMS-101P) at a dilution of 1:1000 in PBS containing Triton X-100. After a 90 min incubation, wells are washed three times with PBS containing Triton X-100, and a secondary antibody (Goat anti-mouse IgG-Cy3 (1.5 mg/ml), Jackson IR Europe #115165003) is added to the wells at a dilution of 1:250 in PBS containing Triton X-100 for 45 min. Wells are subsequently washed three times with PBS containing Triton X-100, and a final staining for nuclei is performed by the addition of DAPI (4',6-diamidino-2-phenylindole) at a dilution of 1:10,000. The imaging of the stained cells is performed for instance on an InCell 1000 High Content Imager (GE Healthcare), reading out the Cy3 channel for N48K Clarin-1 and the DAPI channel for nuclei. The images are analyzed and quantitated using a specific algorithm. This algorithm measures the HA-Clarin-1 staining for each cell based on the additional nuclear segmentation of the DAPI signal (FIG. 1). This algorithm is preferred as it measures the intensity per cell, and thus it is less sensitive for variation in cell number. Per well, approximately 2,000 cells are measured to achieve an average density per cell measurement.

Example 93: $IC_{50}$ Data for Illustrative Compounds of the Invention $IC_{50}$ values for activity of illustrative Pyrazolopyrimidine compounds of the invention were obtained according to the assay method of Example 92. $IC_{50}$ values for Compounds 1-35, 37-39, 42, 44, 45, and 47-97, are less than or equal to 10 micromolar. $IC_{50}$ values for compounds 1-9, 10, 11 13-34, 37-39, 44, 45, 47-97 are all less than or equal to 5 micromolar. $IC_{50}$ values for compounds 1, 2, 4-9, 13, 14, 17, 19, 28, 32, 38, 39, 45, 48-61, 63-74, 76, 77, 79, 81, 83, 85-97 are all less than or equal to 1 micromolar.

Example 94: Assay Method for Identifying One or More Proteins that Bind the Pyrazolopyrimidine Moiety of Compound 44

Compound 44, which includes a pyrazolopyrimidine moiety and biotin group, is useful as a probe for identifying proteins that bind to its pyrazolopyrimidine moiety. The proteins are identified as follows: HEK293-Clarin-1 N48K-HA D9 cells are seeded on collagen-coated 96-well plates at a cell density of 20,000 cells per well in Dulbecco's Modified Eagle Medium (DMEM) containing 10% fetal bovine serum in a humidified incubator at 37° C., 5% $CO_2$. After an overnight incubation, Compound 44 is added to each well at a concentration of less than or equal to 10 micromolar for a 24 hr incubation. The incubation is optionally performed in triplicate. After the 24 hr incubation with Compound 44, the cells are washed three times with phosphate-buffered saline (PBS) and converted to a cell lysate. The protein bound to Compound 44 is then separated and identified using any suitable method known in the art. For example, the cell lysate is applied to streptavidin-coated beads, and the beads are washed with a buffer containing a detergent, such as sodium dodecylsulfate (SDS), to remove any non-specific binding protein. The bound protein is then eluted off the beads with, for example, using 8M guanidine.HCl, pH 1.5, by boiling the beads in SDS-PAGE (-polyacrylamide gel electrophoresis) buffer, or by a tryptic digest of the beads. The mass of the released peptides can then be measured with a mass spectrometer such as Matrix Assisted Laser Desorption Ionization-Time-of-flight (MALDI-TOF) or Electrospray ionization-Time-of-flight (ESI-TOF). These masses are then compared to those of a database containing known protein sequences in order to identify the proteins. The peptide fragments which are bound to Compound 44 are also identified, since the molecular weight of the peptide fragment increases by the molecular weight of Compound 44.

Each reference disclosed in this application is incorporated by reference herein in its entirety.

What is claimed is:

1. A composition comprising an effective amount of

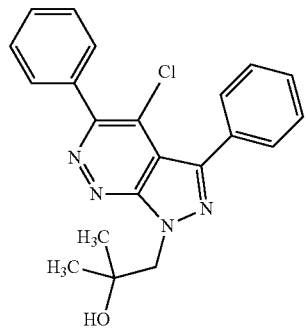 [SMILES: Cc1c(-c2ccccc2)nnc2c1c(-c1ccccc1)nn2CC(C)(C)O ; Cl]

or a pharmaceutically acceptable salt thereof, and a pharmaceutically acceptable carrier or vehicle.

2. A composition comprising an effective amount of

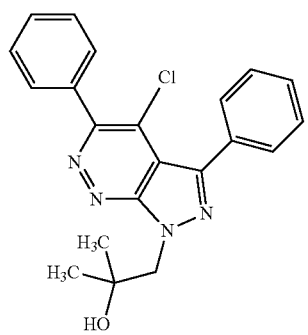 [SMILES: Cc1c(-c2ccccc2)nnc2c1c(-c1ccccc1)nn2CC(C)(C)O ; Cl]

and a pharmaceutically acceptable carrier or vehicle.

* * * * *